US012806359B2

(12) United States Patent
Leng et al.

(10) Patent No.: US 12,806,359 B2
(45) Date of Patent: Nov. 24, 2026

(54) SYSTEMS AND METHODS FOR MANUFACTURE OF A PATIENT INTERFACE AND COMPONENTS THEREOF

(71) Applicant: RESMED ASIA PTE. LTD., Singapore (SG)

(72) Inventors: Wai Hoong Leng, Singapore (SG); Angelene Marie Ozolins, Sydney (AU)

(73) Assignee: Resmed Asia Pte. Ltd., Singapore (SG)

( * ) Notice: Subject to any disclaimer, the term of this patent is extended or adjusted under 35 U.S.C. 154(b) by 1214 days.

(21) Appl. No.: 17/640,731

(22) PCT Filed: Sep. 4, 2020

(86) PCT No.: PCT/SG2020/050514
§ 371 (c)(1),
(2) Date: Mar. 4, 2022

(87) PCT Pub. No.: WO2021/045688
PCT Pub. Date: Mar. 11, 2021

(65) Prior Publication Data
US 2022/0323706 A1 Oct. 13, 2022

(30) Foreign Application Priority Data
Sep. 6, 2019 (AU) ................................ 2019903290

(51) Int. Cl.
*A61M 16/06* (2006.01)

(52) U.S. Cl.
CPC ........ *A61M 16/0683* (2013.01); *A61M 16/06* (2013.01); *A61M 16/0666* (2013.01); *A61M 2210/0618* (2013.01)

(58) Field of Classification Search
CPC ............. A61M 16/0683; A61M 16/06; A61M 16/0666; B33Y 80/00; D04B 1/102;
(Continued)

(56) References Cited

U.S. PATENT DOCUMENTS

| | | | |
|---|---|---|---|
| 3,099,987 | A | 8/1963 | Bartlett, Jr. |
| 4,782,832 | A | 11/1988 | Trimble et al. |

(Continued)

FOREIGN PATENT DOCUMENTS

| | | | |
|---|---|---|---|
| CN | 106714885 | A | 5/2017 |
| JP | 2012-514512 | | 6/2012 |

(Continued)

OTHER PUBLICATIONS

"*Respiratory Physiology*", by John B. West, Lippincott Williams & Wilkins, 9$^{th}$ edition published 2012 (8 pages).

(Continued)

*Primary Examiner* — Kenneth M Lo
*Assistant Examiner* — Zachary Andrew Cain
(74) *Attorney, Agent, or Firm* — Nixon & Vanderhye P.C.

(57) ABSTRACT

Systems and methods producing a customised patient respiratory interface are disclosed. Data representative of one or more landmark features of a head of a human is obtained. One or more landmark feature locations of the landmark features are identified based on the data. A set of manufacturing specifications for production of the patient respiratory interface component is determined based on the one or more landmark feature locations. The patient respiratory interface component is produced based on the set of manufacturing specifications.

62 Claims, 39 Drawing Sheets

(58) Field of Classification Search
CPC ........ D04B 1/12; D04B 37/02; G06V 40/171; G16H 20/40; G16H 30/40
See application file for complete search history.

(56) References Cited

U.S. PATENT DOCUMENTS

| | | | | |
|---|---|---|---|---|
| 4,944,310 | A | 7/1990 | Sullivan | |
| 6,532,959 | B1 | 3/2003 | Berthon-Jones | |
| 6,581,594 | B1 | 6/2003 | Drew et al. | |
| 7,827,038 | B2 | 11/2010 | Richard et al. | |
| 7,866,944 | B2 | 1/2011 | Kenyon et al. | |
| 8,254,637 | B2 | 8/2012 | Abourizk et al. | |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 10,157,477 | B2 | 12/2018 | Chen | |
| 2004/0133604 | A1* | 7/2004 | Lordo | G16H 10/60 |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2011/0197341 | A1* | 8/2011 | Formica | B32B 5/024 2/209.3 |
| 2013/0133646 | A1 | 5/2013 | Rose et al. | |
| 2014/0209098 | A1* | 7/2014 | Dunn | A61M 16/06 112/475.11 |
| 2015/0265794 | A1 | 9/2015 | De Kruyff et al. | |
| 2016/0271354 | A1 | 9/2016 | Grashow et al. | |
| 2017/0173289 | A1* | 6/2017 | Lucey | A61B 5/1079 |
| 2017/0274167 | A1 | 9/2017 | Huddart et al. | |
| 2017/0304577 | A1 | 10/2017 | Bearne et al. | |
| 2017/0326320 | A1 | 11/2017 | Baigent et al. | |
| 2018/0117272 | A1 | 5/2018 | Fu et al. | |
| 2018/0207385 | A1 | 7/2018 | Freestone et al. | |
| 2019/0160247 | A1* | 5/2019 | Kimmel | G06T 19/00 |
| 2019/0167934 | A1 | 6/2019 | Lucey et al. | |
| 2019/0258749 | A1* | 8/2019 | Ho | G06F 30/00 |

FOREIGN PATENT DOCUMENTS

| | | | | |
|---|---|---|---|---|
| JP | 2017523827 | A * | 8/2017 | A61B 5/1077 |
| WO | WO 98/004310 | A1 | 2/1998 | |
| WO | WO 98/034665 | A1 | 8/1998 | |
| WO | WO 2000/078381 | A1 | 12/2000 | |
| WO | WO 2004/073778 | A1 | 9/2004 | |
| WO | WO 2005/063328 | A1 | 7/2005 | |
| WO | WO 2006/074513 | A1 | 7/2006 | |
| WO | WO 2006/130903 | A1 | 12/2006 | |
| WO | WO 2009/052560 | A1 | 4/2009 | |
| WO | WO 2010/135785 | A1 | 12/2010 | |
| WO | WO 2012/171072 | A1 | 12/2012 | |
| WO | WO 2013/020167 | A1 | 2/2013 | |
| WO | WO 2013/026091 | A1 | 2/2013 | |
| WO | WO 2013/068950 | A1 | 5/2013 | |
| WO | 2017/000031 | | 1/2017 | |
| WO | WO 2018/002169 | A1 | 1/2018 | |

OTHER PUBLICATIONS

International Search Report mailed Nov. 11, 2020 issued in International Application No. PCT/SG2020/050514 (3 pages).
Written Opinion of the ISA mailed Nov. 11, 2020 issued in International Application No. PCT/SG2020/050514 (6 pages).
Third Office Action with English Translation for Application No. CN 202080074601.0, 25 pages, dated Dec. 22, 2025.
Notice of Reasons for Refusal with English translation for Application No. JP 2022-514777, 47 pages, dated Oct. 14, 2025.

* cited by examiner

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2015 ResMed Limited

Copyright 2015 ResMed Limited

Copyright 2015 ResMed Limited

Copyright 2015 ResMed Limited

SYSTEMS AND METHODS FOR MANUFACTURE OF A PATIENT INTERFACE AND COMPONENTS THEREOF

1 CROSS-REFERENCE TO RELATED APPLICATIONS

This application is the U.S. national phase of International Application No. PCT/SG2020/050514 filed Sep. 4, 2020 which designated the U.S. and claims priority to AU Provisional Application No. 2019903290 filed Sep. 6, 2019, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.1.3 Patient Interface Sizing and Customisation

Patient interfaces, as described above, may be provided to a patient in various forms, such as a nasal mask or full-face mask/oro-nasal mask (FFM) or nasal pillows mask, for example Such patient interfaces are manufactured with various dimensions to accommodate a specific patient's anatomical features in order to facilitate a comfortable interface that is functional to provide, for example, positive pressure therapy. This is particularly significant where a seal with the patient's face is necessary for providing an effective respiratory treatment, such as in the application of positive pressure therapy. Moreover, comfort increases patient compliance with therapy.

A patient interface customized to a particular user is expected to improve user compliance with therapy or provision of the most effective therapy. However, the user may need to schedule an appointment with and travel to a facility that has the equipment and personnel to make such an assessment. Such scheduling and travel may be inconvenient for the user, and may dissuade the user from obtaining a patient interface suited to them.

The above drawbacks have been described in the specific context of customized patient interfaces and masks, for instance for an individual suffering from a respiratory condition. However similar drawbacks and challenges may apply to designing and manufacturing any article, apparatus or other apparel that may be worn on a person's head or face. For instance, if a user wishes to order custom-fit sunglasses, goggles, a face mask, or costume, the user may be inconvenienced to have to pay and/or travel in order to be assessed.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

Another aspect of one form of the present technology is a patient interface that is moulded or otherwise constructed with a perimeter shape which is complementary to that of an intended wearer.

An aspect of one form of the present technology is a method of manufacturing system and apparatus.

Another form of the present technology comprises an apparatus or device for treating a respiratory disorder, or component thereof, customised to an intended user.

Another form of the present technology comprises a patient interface, or component thereof, customised to an intended wearer.

Another form of the present technology comprises a method for production of patient interface, or component thereof, customised to an intended wearer.

An aspect of one form of the present technology is a processor-implemented method for producing a customised patient respiratory interface component, the method comprising:

- receiving, using communication circuitry, data representative of one or more landmark features of a head of a human;
- identifying, using at least one processor, one or more landmark feature locations of the landmark features based on the data;
- determining, using the at least one processor, a set of manufacturing specifications for production of the patient respiratory interface component based on the one or more landmark feature locations; and
- controlling one or more manufacturing machines to produce the patient respiratory interface component based on the set of manufacturing specifications.

An aspect of one form of the present technology is a processor-implemented method for producing a customised patient respiratory interface component, the method comprising:

- receiving, using communication circuitry, data representative of one or more landmark features of a head of a human;
- identifying, using at least one processor, one or more landmark feature locations of the landmark features based on the data;
- determining, using the at least one processor, a set of manufacturing specifications for production of the patient respiratory interface component based on the one or more landmark feature locations; and
- causing one or more manufacturing machines to produce the patient respiratory interface component based on the set of manufacturing specifications.

In examples: (a) the data is representative of one or more landmark features of a head of an intended user of the patient interface; (b) the data comprises image data; (c) at least a portion of the image data is captured by an image sensor (d) the method comprises the step of capturing at least a portion of the image data with an image sensor; (e) the data comprises two-dimensional image data; and/or (f) the data comprises three-dimensional image data.

In an example, causing one or more manufacturing machines to produce the patient respiratory interface component includes, controlling the one or more manufacturing machines to produce the patient respiratory interface component based on the set of manufacturing specifications.

In an example, the method is performed by a manufacturing system including the at least one processor and the communication circuitry.

In examples the method comprises; (a) the step of capturing at least a portion of the data with an image sensor; and/or (b) the step of identifying at least one relationship between two or more of the landmark feature locations, wherein determining the set of manufacturing specifications is based at least in part on the at least one relationship between the two or more of the landmark feature locations.

In examples identifying the at least one relationship between the two or more of the landmark feature locations comprises determining distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion.

In examples identifying the at least one relationship between the two or more of the landmark feature locations comprises: (a) determining a distance in the sagittal plane between the subnasale and the tragion; (b) determining a vertical distance in the sagittal plane between the subnasale and the sellion; (c) determining a distance between the subnasale and the coronal plane aligned with the tragion, the distance being normal to said coronal plane; (d) determining a distance between the lateral-most point of the orbital margin and the coronal plane aligned with the tragion, the distance being normal to said coronal plane; (e) determining a vertical distance between the subnasale and the superior-most point of the head; (f) determining a vertical distance between the superior-most point of the head and the Frankfort horizontal plane; and/or (g) determining a distance between the rearmost point of the head and a coronal plane aligned with the tragion, the distance being normal to said coronal plane.

In examples: (a) the method comprises the step of determining at least one performance requirement for the patient respiratory interface component based on the one or more landmark feature locations; (b) the at least one performance requirement comprises one or more of: a force to be applied by or to the component, elasticity, dimensions, tactile feel, breathability, and positioning on the head; (c) the patient respiratory interface component comprises a plurality of regions, and at least one performance requirement is determined for each region; (d) the at least one performance requirement is determined based at least in part on properties of another component of the patient interface intended for use with the customised patient respiratory interface component; and/or (e) determining the set of manufacturing specifications is based at least in part on the at least one performance requirement.

In examples the set of manufacturing specifications comprises: (a) at least one material specification; (b) at least one construction technique specification; and/or (c) at least one dimension specification.

In examples, determining the set of manufacturing specifications comprises: (a) selecting the set of manufacturing specifications from a plurality of pre-existing sets of manufacturing specifications; (b) selecting the set of pre-existing manufacturing specifications is based on a comparison between the one or more landmark feature locations determined for the human, and one or more landmark feature locations associated with the set of pre-existing manufacturing specifications; and/or (c) selecting a plurality of manufacturing specifications to form the set of manufacturing specifications from a plurality of pre-existing manufacturing specifications.

In examples, the method comprises producing manufacturing machine programming instructions for production of the patient interface or component thereof based on the set of manufacturing specifications. In examples, producing the patient respiratory interface component comprises programming at least one manufacturing machine with the manufacturing machine programming instructions, and operating the at least one manufacturing machine according to the manufacturing machine programming instructions.

In examples: (a) producing the manufacturing machine programming instructions comprises generating a map representing the set of manufacturing specifications, and generating the manufacturing machine programming instructions based on the map; and/or (b) producing the manufacturing machine programming instructions comprises generating a model of the patient respiratory interface component based on the set of manufacturing specifications, and generating the manufacturing machine programming instructions based on the model.

In examples, producing the patient respiratory interface component comprises (a) mechanical manipulation of yarn to produce the component; (b) knitting the component; (c) flat knitting the component; (d) circular knitting the component; (e) forming the component from textiles; (e) additive manufacturing of the component; (f) three-dimensional printing of the component; and/or (g) laser cutting of the component, and/or generating instructions for one or more manufacturing apparatuses configured to produce the component and controlling the one or more manufacturing apparatuses to produce the component based on the generated instructions.

In examples, the patient respiratory interface component comprises a headgear strap of a positioning and stabilising structure for a patient interface. In examples, the set of manufacturing specifications comprises: (a) headgear strap dimensions; (b) at least one dimension of a posterior strap portion for the headgear strap, the posterior strap portion configured to lie against at least posterior surfaces of the head in use; (c) a length of each one of a pair of upper strap portions for the headgear strap, each upper strap portion being configured to lie on a respective side of the head in use; (d) an upper strap location on a posterior strap portion for the headgear strap from which each one of a pair of upper strap portions for the headgear strap extends; (e) an upper strap direction in which one of a pair of upper strap portions for the headgear strap extends from a posterior strap portion for the headgear strap; (f) a length of each one of a pair of lower strap portions for the headgear strap, each lower strap portion being configured to lie on a respective side of the head in use; (g) a lower strap location on a posterior strap portion for the headgear strap from which each one of a pair of lower strap portions extends; and/or (h) a length of a ring strap portion for the headgear strap, the ring strap portion having a superior portion configured to overlay the parietal bones of the head in use and having an inferior portion configured to overlay or lie inferior to the occipital bone of the head in use.

In examples, the set of manufacturing specifications is determined such that, when the patient interface is donned by the human in use, the headgear strap applies a predetermined force to a seal-forming structure of the patient interface. In examples, the predetermined force is: (a) between 3N and 5N; (b) about 4N.

In examples the patient respiratory interface component comprises a frame of the patient interface. In examples the set of manufacturing specifications comprises: (a) frame dimensions; (b) a length of each one of a pair of upper arms of the frame, each upper arm being configured to connect with a respective upper strap portion of a positioning and stabilising structure in use; (c) a direction at which each one of a pair of upper arms of the frame extends from a central portion of the frame; (d) a length of each one of a pair of lower arms of the frame, each lower arm being configured to connect with a respective lower strap portion of a positioning and stabilising structure in use; and/or (e) a direction at which each one of a pair of lower arms of the frame extends from a central portion of the frame.

In examples the patent respiratory interface component comprises: (a) a plenum chamber of the patient interface; (b) a seal-forming structure of the patient interface; and/or (c) a cushion of the patient interface.

In examples the set of manufacturing specifications identify specifications for a headgear strap of a positioning and stabilising structure for a patient interface and include at least one of knit structure, material composition, yarn denier, and/or machine gauge for producing the headgear strap, wherein the one or more of manufacturing specifications define a stretch characteristic of the positioning and stabilising structure.

An aspect of one form of the present technology is a system for producing a customised patient respiratory interface component, the system comprising:

one or more processors for receiving data representative of one or more landmark features of a human;

the one or more processors further configured to identify one or more landmark feature locations of the landmark features based on the data;

the one or more processors further configured to determine a set of manufacturing specifications for production of the patient respiratory interface component based on the one or more landmark feature locations; and at least one manufacturing machine configured to produce the patient respiratory interface component based on the set of manufacturing specifications.

An aspect of one form of the present technology is a processor-implemented method performed by a processing system including at least one processor and communication circuitry for production of a patient respiratory interface component, the method comprising:

receiving, using the communication circuitry, data representative of one or more landmark features of a head of a human;

identifying, using the processing system, one or more landmark feature locations of the landmark features based on the data;

determining, using the processing system, a set of manufacturing specifications for production of the patient respiratory interface component based on the one or more landmark feature locations; and communicating, using the communication circuitry, the set of manufacturing specifications to a manufacturing system comprising at least one manufacturing machine configured to produce the patient respiratory interface component based on the set of manufacturing specifications.

An aspect of one form of the present technology is a system for producing a customised patient respiratory interface component, the system comprising:

one or more processors for receiving data representative of one or more landmark features of a head of a human;

the one or more processors further configured to identify one or more landmark feature locations of the landmark features based on the data;

the one or more processors further configured to determine a set of manufacturing specifications for production of the patient respiratory interface component based on the one or more landmark feature locations; and the one or more processors further configured to communicate the set of manufacturing specifications to a manufacturing system comprising at least one manufacturing machine configured to produce the patient respiratory interface component based on the set of manufacturing specifications.

An aspect of one form of the present technology is a processor-implemented method performed by a processing system including at least one processor and communication circuitry for production of a patient respiratory interface component, the method comprising:

receiving, using the communication circuitry, data representative of one or more landmark feature locations of landmark features of a head of a human;

determining, using the processing system, a set of manufacturing specifications for production of the patient respiratory interface component based on the one or more landmark feature locations; and communicating, using the communication circuitry, the set of manufacturing specifications to a manufacturing system comprising at least one manufacturing machine configured to produce the patient respiratory interface component based on the set of manufacturing specifications.

An aspect of one form of the present technology is a system for producing a customised patient respiratory interface component, the system comprising:

one or more processors for receiving one or more landmark feature locations of landmark features of a head of a human, the one or more landmark feature locations identified from data representative of the one or more landmark features of the head;

the one or more processors further configured to determine a set of manufacturing specifications for production of the patient respiratory interface component based on the one or more landmark feature locations; and the one or more processors further configured to communicate the set of manufacturing specifications to a manufacturing system comprising at least one manufacturing machine configured to produce the patient respiratory interface component based on the set of manufacturing specifications.

An aspect of one form of the present technology is a processor-implemented method for production of a patient respiratory interface component, the method comprising:

receiving, using communication circuitry, a set of manufacturing specifications for production of the patient respiratory interface component, wherein the set of manufacturing specifications are determined based on one or more landmark feature locations identified from data representative of one or more landmark features of a head of a human; and controlling one or more manufacturing machines to produce the patient respiratory interface component using based on the set of manufacturing specifications.

An aspect of one form of the present technology is a processor-implemented method for production of a patient respiratory interface component, the method comprising:

receiving, using communication circuitry, a set of manufacturing specifications for production of the patient respiratory interface component, wherein the set of manufacturing specifications are determined based on one or more landmark feature locations identified from data representative of one or more landmark features of a head of a human; and causing one or more manufacturing machines to produce the patient respiratory interface component using based on the set of manufacturing specifications.

In one example, causing one or more manufacturing machines to produce the patient respiratory interface component includes controlling the one or more manufacturing machines to produce the patient respiratory interface component.

An aspect of one form of the present technology is a system for producing a customised patient respiratory interface component, the system comprising:

one or more processors for receiving a set of manufacturing specifications for production of the patient respiratory interface component, wherein the set of manufacturing specifications are determined based on one or more landmark feature locations identified from data representative of one or more landmark features of a head of a human; and at least one manufacturing machine configured to produce the patient respiratory interface component based on the set of manufacturing specifications.

An aspect of one form of the present technology is a processor-implemented method for production of a patient respiratory interface component, the method comprising:

obtaining, based on data received from a device using communication circuitry, information representative of one or more landmark feature locations for a human head;

determining, using at least one processor, a set of manufacturing specifications for production of the patient respiratory interface component based on the one or more landmark feature locations; and causing one or more manufacturing machines to produce the patient respiratory interface component based on the set of manufacturing specifications.

An aspect of one form of the present technology is a system for producing a patient respiratory interface component, the system comprising:

one or more processors for obtaining information representative of one or more landmark feature locations for a human head;

the one or more processors further configured to determine a set of manufacturing specifications for production of the patient respiratory interface component based on the one or more landmark feature locations; and the one or more processors further configured to produce the patient respiratory interface component based on the set of manufacturing specifications.

An aspect of one form of the present technology is an apparatus for producing a patient respiratory interface component, the apparatus comprising:

means for obtaining information representative of one or more landmark feature locations for a human's head;

means for determining a set of manufacturing specifications for production of the patient respiratory interface component based on the one or more landmark feature locations; and means for producing the patient respiratory interface component based on the set of manufacturing specifications.

In examples, the component comprises: (a) a sensor produced based on the set of manufacturing specifications; (b) a feature configured to receive and/or locate a sensor relative to the component; (c) a sensor element configured to interface with a sensing device.

Another form of the present technology comprises a positioning and stabilising structure for a patient interface produced by any one of the above methods and/or systems.

Another form of the present technology comprises a positioning and stabilising structure for a patient interface, the positioning and stabilising structure being formed from flat knitting based on instructions generated based on identification of facial landmarks and/or distances between said landmarks.

One form of the present technology comprises a positioning and stabilising structure for a patient interface, the positioning and stabilising structure comprising an integrally formed strap that is formed by knitting. The strap may connect to a frame or plenum chamber of the patient interface via four connection points.

Another form of the present technology comprises a positioning and stabilising structure for a patient interface, the positioning and stabilising structure comprising an integrally formed knitted strap that comprises multiple knitting structures, each knitting structure comprising different mechanical properties. The strap may be formed by knitting.

Another form of the present technology comprises a positioning and stabilising structure for a patient interface, the positioning and stabilising structure comprising an integrally formed knitted strap comprising at least a first portion and a second portion, the first portion having a different elasticity to the second portion. The first portion may comprise a ring strap portion configured to lie against posterior and superior surfaces of the patient's head. The second portion may comprise upper strap portions configured to lie alongside the patient's face in use and connect between the ring strap portion and a plenum chamber of the patient interface. The strap may be formed by knitting.

Another form of the present technology comprises a positioning and stabilising structure for a patient interface, the positioning and stabilising structure comprising an integrally formed knitted strap having a plurality of ventilation portions forming regions of increased breathability. The ventilation portions may comprise a first knitting structure and other portions of the strap may comprise a second knitting structure different from the first knitting structure. The ventilation portions may be formed with a pique mesh knitting structure while other portions of the strap may be formed with a single jersey or double jersey knitting structure. The strap may be formed by knitting.

Another form of the present technology comprises a positioning and stabilising structure for a patient interface, the positioning and stabilising structure comprising a strap comprising a ring strap portion configured to lie against posterior and superior surfaces of a patient's head and define a loop having an inside periphery, the ring strap portion comprising a rigidised portion at or proximate the inside periphery of the loop. The rigidised portion may comprise a first knitting structure and other portions of the ring strap portion may comprise a second knitting structure. The rigidised portion may comprise a pique knitting structure while other portions of the strap may comprise a single jersey or double jersey knitting structure. The strap may be formed by knitting.

Another form of the present technology comprises a positioning and stabilising structure for a patient interface, the positioning and stabilising structure comprising a strap comprising a fastening portion configured to be looped back and secured to itself to secure the strap to a frame or plenum chamber of the patient interface, the strap comprising a blind guide configured to provide a tactile indication of the location of the fastening portion of the strap. The strap may be an integrally formed with the blind guide. The strap may be formed by knitting.

Another form of the present technology comprises a patient interface comprising:

a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient, said vent structure being sized and shaped to maintain the therapeutic pressure in the plenum chamber in use;

wherein the patient interface is configured to allow the patient to breath from ambient through their mouth in the absence of a flow of pressurised air through the plenum chamber inlet port, or the patient interface is configured to leave the patient's mouth uncovered;

wherein the positioning and stabilising structure comprises:

a ring strap portion having a superior portion configured to overlay the parietal bones of the patient's head in use and having an inferior portion configured to overlay or lie inferior to the occipital bone of the patient's head in use, the ring strap portion defining a loop;

a pair of upper strap portions, each configured to connect between the ring strap portion and the plenum chamber in use on a respective side of the patient's head superior to an otobasion superior;

wherein the ring strap portion comprises a rigidised portion provided along a length of the loop defined by the ring strap portion.

In examples: a) the rigidised portion is provided substantially along the entire length of the loop defined by the ring strap portion; b) the rigidised portion is provided to the ring strap portion proximate an inside periphery of the ring strap portion; c) the rigidised portion defines at least a portion of the inside periphery of the ring strap portion; d) the rigidised portion forms substantially the entire inside periphery of the ring strap portion; e) the rigidised portion is provided substantially centrally between an inside periphery of the ring strap portion and an outside periphery of the ring strap portion; f) the upper strap portions are stretchable; g) the rigidised portion is substantially non-stretchable; h) the ring strap portion comprises rounded edges; i) the rigidised portion comprises an increased material thickness relative to adjacent portions of the ring strap portion; j) a patient-contacting side of the ring strap portion is substantially flat and the increased material thickness is provided to a non-patient-contacting side of the ring strap portion; k) the ring strap portion comprises a thickness of 4 mm in the rigidised portion; l) the ring strap portion comprises a thickness of 2.5 mm in regions of the ring strap portion other than the rigidised portion; m) the rigidised portion is larger in regions of the ring strap portion proximate the upper strap portions than in other regions of the ring strap portion; and/or n) the rigidised portion is wider proximate the upper strap portions than in other regions of the ring strap portion.

In further examples: a) the ring strap portion comprises at least one ventilation portion structured and/or arranged to provide increased breathability through the ring strap portion at the ventilation portion; b) the ventilation portion comprises a knitted fabric having a pique mesh knitting structure; c) the ventilation portion is less stretchable than other portions of the ring strap portion; d) the rigidised portion surrounds the ventilation portion; e) the ring strap portion comprises a pair of superior ventilation portions, each provided proximate a respective upper strap portion; f) the rigidised portion surrounds each of the superior ventilation portions; g) the rigidised portion comprises a higher material thickness on a posterior side of each of the superior ventilation portions than on an anterior side of each of the superior ventilation portions; h) the positioning and stabilising structure comprises a pair of lower strap portions, each lower strap portion configured to connect between the ring strap portion and the plenum chamber in use on a respective side of the patient's head inferior to the otobasion superior; i) the ring strap portion comprises an inferior ventilation portion provided between the pair of lower strap portions; j) the inferior ventilation portion comprises an inferior edge spaced from an inferior edge of the ring strap portion; k) the inferior edge of the inferior ventilation portion comprises a greater curvature than the inferior edge of the ring strap portion to create a maximum spacing between the inferior edge of the inferior ventilation portion and the inferior edge of the ring strap portion at or proximate the sagittal plane of the patient's head in use; l) the lower strap portions are stretchable; m) the ring strap portion comprises a knitted fabric structure; n) the ring strap portion is formed by flat knitting; o) the ring strap portion comprises a single jersey knitting structure; p) the ring strap portion comprises a double jersey loop formation knitting structure; q) the rigidised portion comprises a pique knitting structure; r) the superior portion of the ring strap portion comprises a pair of overhead strap portions adjustably connected to each other proximate the sagittal plane of the patient's head; s) the overhead strap portions are adjustably connected with a buckle; t) the overhead strap portions comprise hook and loop fastening material to allow each of the overhead strap portions to be passed through a portion of the buckle and secured back onto itself; u) the positioning and stabilising structure comprises a frame coupled to the plenum chamber, the upper strap portions being configured to connect to the frame; and/or v) the positioning and stabilising structure further comprises lower strap portions configured to connect to the frame.

Another form of the present technology comprises a patient interface comprising:

a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient, said vent structure being sized and shaped to maintain the therapeutic pressure in the plenum chamber in use;

wherein the patient interface is configured to allow the patient to breath from ambient through their mouth in the absence of a flow of pressurised air through the plenum chamber inlet port, or the patient interface is configured to leave the patient's mouth uncovered;

wherein the positioning and stabilising structure comprises at least one strap configured to connect to the plenum chamber, the strap being formed from a knitted fabric and comprising a fastening portion proximate an end of the strap, the fastening portion being structured and/or arranged to allow the strap to be looped back and fastened onto itself to connect to the plenum chamber; and wherein the strap comprises at least one blind guide formed by the knitted fabric and configured to provide a tactile indication of the location of the fastening portion on the strap.

In examples: a) the strap is formed by flat knitting; b) the strap comprises a non-patient-contacting surface and the at least one blind guide comprises at least one of a raised portion and a recessed portion being raised and/or recessed (as the case may be) with respect to the non-patient-contacting surface; c) the raised/recessed portion surrounds at least part of the fastening portion of the strap; d) the raised portion comprises an elongate raised profile on the non-patient-contacting surface of the strap; e) the elongate raised profile is provided at one or more edges of the fastening portion; f) the elongate raised profile is provided at edges of the fastening portion which in use are superior, posterior and inferior edges; g) the elongate raised profile comprises a rounded raised surface; h) the raised/recessed portion is formed by an increased/decreased thickness of the strap in comparison to adjacent regions of the strap; i) the fastening portion of the strap comprises a hook-and-loop fastening material; j) the fastening portion comprises an end portion comprising one of a hook material and a loop material provided to the non-patient-contacting surface and an intermediate portion comprising the other of the hook material and the loop material provided to the non-patient-contacting surface; k) the intermediate portion is longer than the end portion. The intermediate portion may be several times longer than the end portion; l) the strap and the blind guide are formed during a single knitting process; m) the blind guide comprises a pique knitting structure; n) the strap comprises a single jersey knitting structure; o) the strap comprises a double jersey loop formation; p) the strap connects to the plenum chamber via a frame of the patient interface; q) the strap comprises: a ring strap portion having a superior portion configured to lie against the patient's head over the parietal bones of the patient's head in use and having an inferior portion configured to lie against the patient's head over or inferior to the occipital bones of the patient's head in use; and a pair of upper strap portions, each configured to connect between the ring strap portion and the plenum chamber in use on a respective side of the patient's head superior to an otobasion superior; r) the strap comprises a pair of lower strap portions, each lower strap portion being configured to connect between the ring strap portion and the plenum chamber in use on a respective side of the patient's head inferior to the otobasion superior; and/or s) the strap and the blind guide are integrally formed.

Another form of the present technology comprises a patient interface comprising:

a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient, said vent structure being sized and shaped to maintain the therapeutic pressure in the plenum chamber in use;

wherein the patient interface is configured to allow the patient to breath from ambient through their mouth in the absence of a flow of pressurised air through the plenum chamber inlet port, or the patient interface is configured to leave the patient's mouth uncovered;

wherein the positioning and stabilising structure comprises:

a pair of headgear conduits to receive the flow of air from a connection port on top of the patient's head and to deliver the flow of air to the entrance of the patient's airways via the seal-forming structure, each headgear conduit constructed and arranged to contact, in use, at least a region of the patient's head superior to an otobasion superior of the patient's head on a respective side of the patient's head;

a strap integrally formed by flat knitting, the headgear strap comprising:

a neck strap portion configured to overlay the occipital bone of the patient's head and/or lie against the patient's neck in use;

a pair of upper strap portions, each configured to connect between the neck strap portion and a respective headgear conduit on a respective side of the patient's head; and a pair of lower strap portions, each configured to connect between the neck strap portion and a respective headgear conduit.

In examples: a) the strap is formed by a single flat knitting process; b) the strap comprises a rigidised portion; c) the rigidised portion comprises a pique knitting structure; d) the neck strap portion comprises the rigidised portion; e) the neck strap portion comprises one or more stretchable portions; f) the neck strap portion comprises a superior stretchable portion and an inferior stretchable portion; g) the superior stretchable portion is provided along a superior edge of the neck strap portion; h) the inferior stretchable portion is provided along an inferior edge of the neck strap portion; i) the strap comprises a ventilation portion structured and/or arranged to provide increased breathability through the strap at the ventilation portion; j) the ventilation portion is located in the neck strap portion; k) the ventilation portion comprises a knitted fabric having a pique mesh knitting structure; l) the ventilation portion is less stretchable than other portions of the ring strap portion; and/or m) the rigidised portion surrounds the ventilation portion.

In further examples: a) the strap comprises a fastening portion proximate an end of the strap, the fastening portion being structured and/or arranged to allow the strap to be looped back and fastened onto itself to connect to the plenum chamber, the strap comprising at least one blind guide formed by knitted fabric forming the integrally formed strap and configured to provide a tactile indication of the location of the fastening portion on the strap; b) the strap comprises a non-patient-contacting surface and the at least one blind guide comprises a raised portion, the raised portion being raised with respect to the non-patient-contacting surface; c) the raised portion comprises an elongate raised profile on the non-patient-contacting surface of the strap; d) the fastening portion of the strap comprises a hook-and-loop fastening material; and/or e) each of the upper strap portions and lower strap portions comprises a respective blind guide.

An aspect of one form of the present technology is a processor-implemented method for producing a customised component of an apparatus or device for treatment of a respiratory disorder, the method comprising:

receiving, using communication circuitry, data representative of one or more functional requirements;

determining, using at least one processor, a set of manufacturing specifications for production of the component based on the one or more functional requirements; and causing one or more manufacturing apparatuses to produce the component based on the set of manufacturing specifications.

In examples: (a) the data representative of functional requirements comprises at least one physiological characteristic of an intended user of the apparatus; (b) the data representative of the at least one physiological characteristic is obtained using at least one sensor; (c) the physiological characteristic is a characteristic of breathing; (d) the physiological characteristic is at least one of: carbon dioxide ($CO_2$) saturation, and moisture content; (e) the functional requirement comprises one or more of: a characteristic of a heat and moisture exchanger relating to absorption of heat and/or moisture from a volume of air of expired flow during patient exhalation; vent performance; heat dissipation, tactile feel (e.g. softness and/or smoothness); (f) causing one or more manufacturing apparatuses to produce the component includes controlling the one or more manufacturing apparatuses to produce the component based on the set of manufacturing specifications; and/or (g) the method is performed by a manufacturing system including the at least one processor and the communication circuitry.

The methods, systems, devices and apparatus described may be implemented so as to improved comfort, cost, efficacy, ease of use and manufacturability of customized patient interface and/or component thereof.

The methods, systems, devices and apparatus described may be implemented so as to improve the functionality of a processor, such as a processor of a specific purpose computer used to identify landmark features and/or their locations, identifying relationships between the landmark features, determining functional requirements (e.g., for a patient interface and/or one or more components thereof, determining manufacturing specifications, and/or producing or generating manufacturing machine programmable instructions. Moreover, the described methods, systems, devices and apparatus can provide improvements in the technological field of automated generation of machine programming instructions for producing a customized patient interface and/or component thereof. Moreover, the described methods systems, devices and apparatus provide increased flexibility in producing customized patient interface and/or component thereof that will properly fit a user and provide the most comfort, and/or faster production of the customized patient interface and/or component thereof. Examples of the present technology provide customized patient interface and/or component thereof faster than conventional methods (e.g., from the time they are requested) and/or with accuracy that cannot be provided by conventional methods, at least because a patient, clinician and/or manufacturer cannot accurately consider and implement all of the factors that go into providing a customized patient interface and/or component thereof with accuracy, improved comfort and/or without significant cost and/or time.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
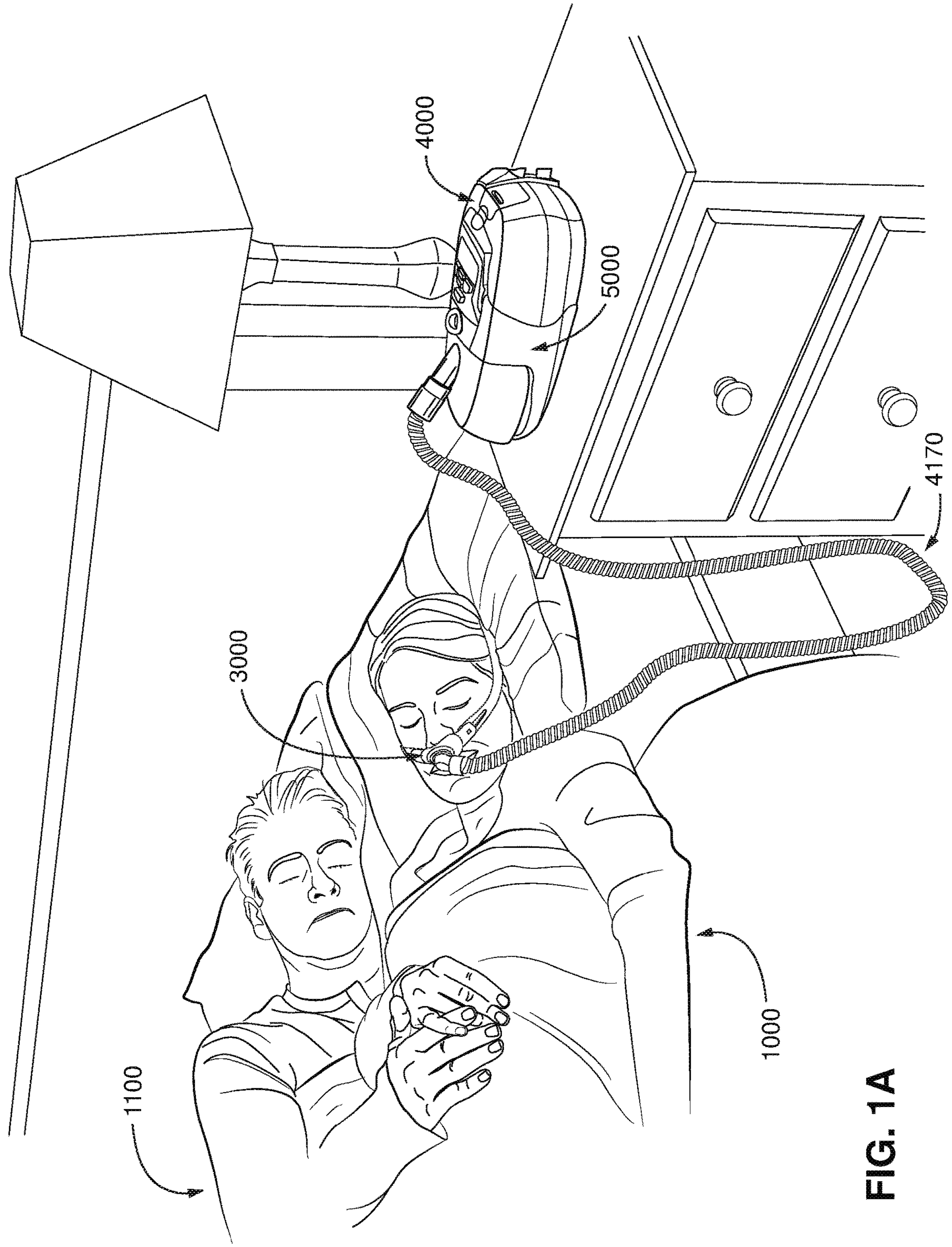
Figure 1B:
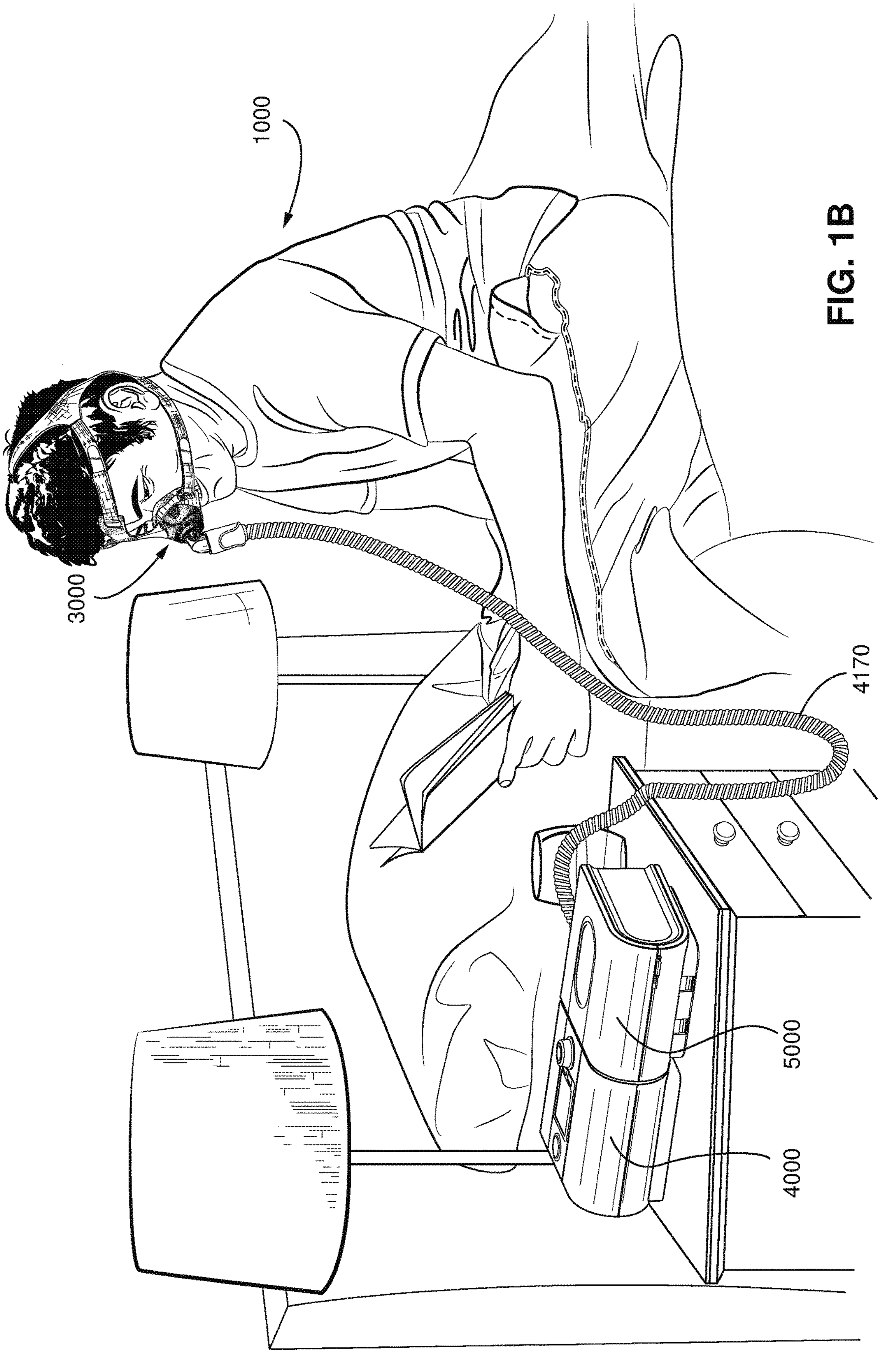
Figure 1C:
Figure 2A:
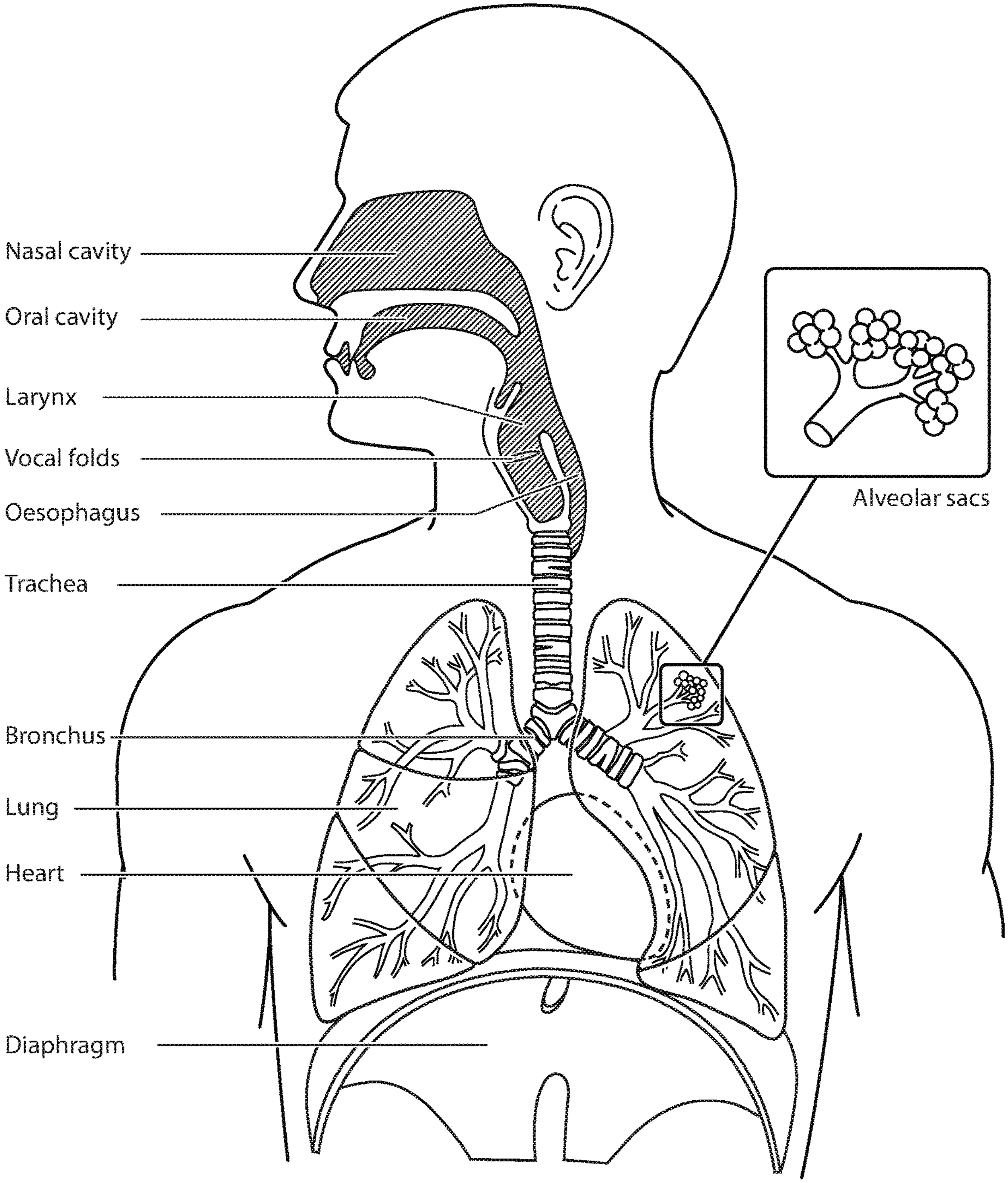
FIG. 2A shows an overview of a human respiratory system including the nasal and oral cavities, the larynx, vocal folds, oesophagus, trachea, bronchus, lung, alveolar sacs, heart and diaphragm.
Figure 2B:
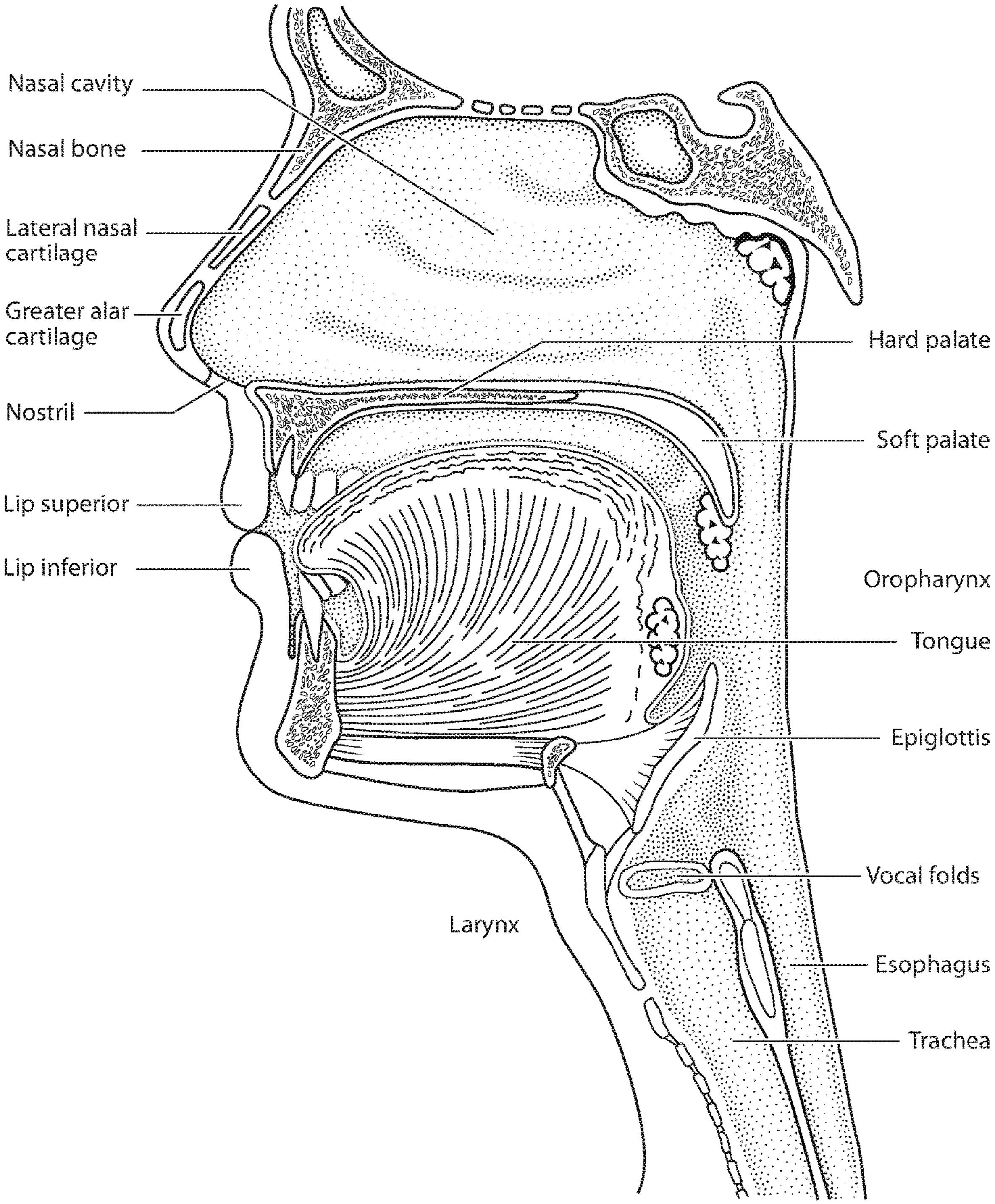
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
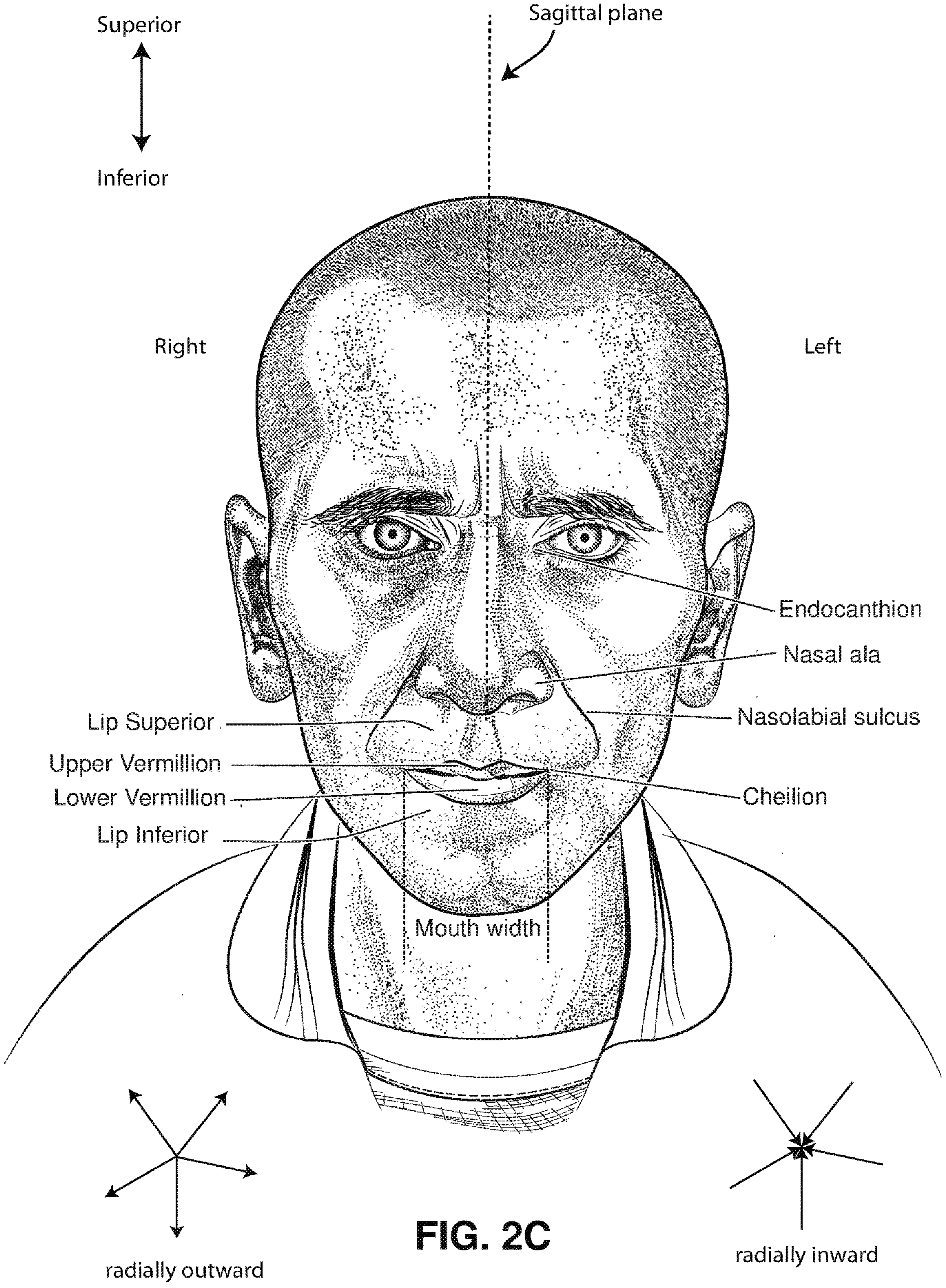
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
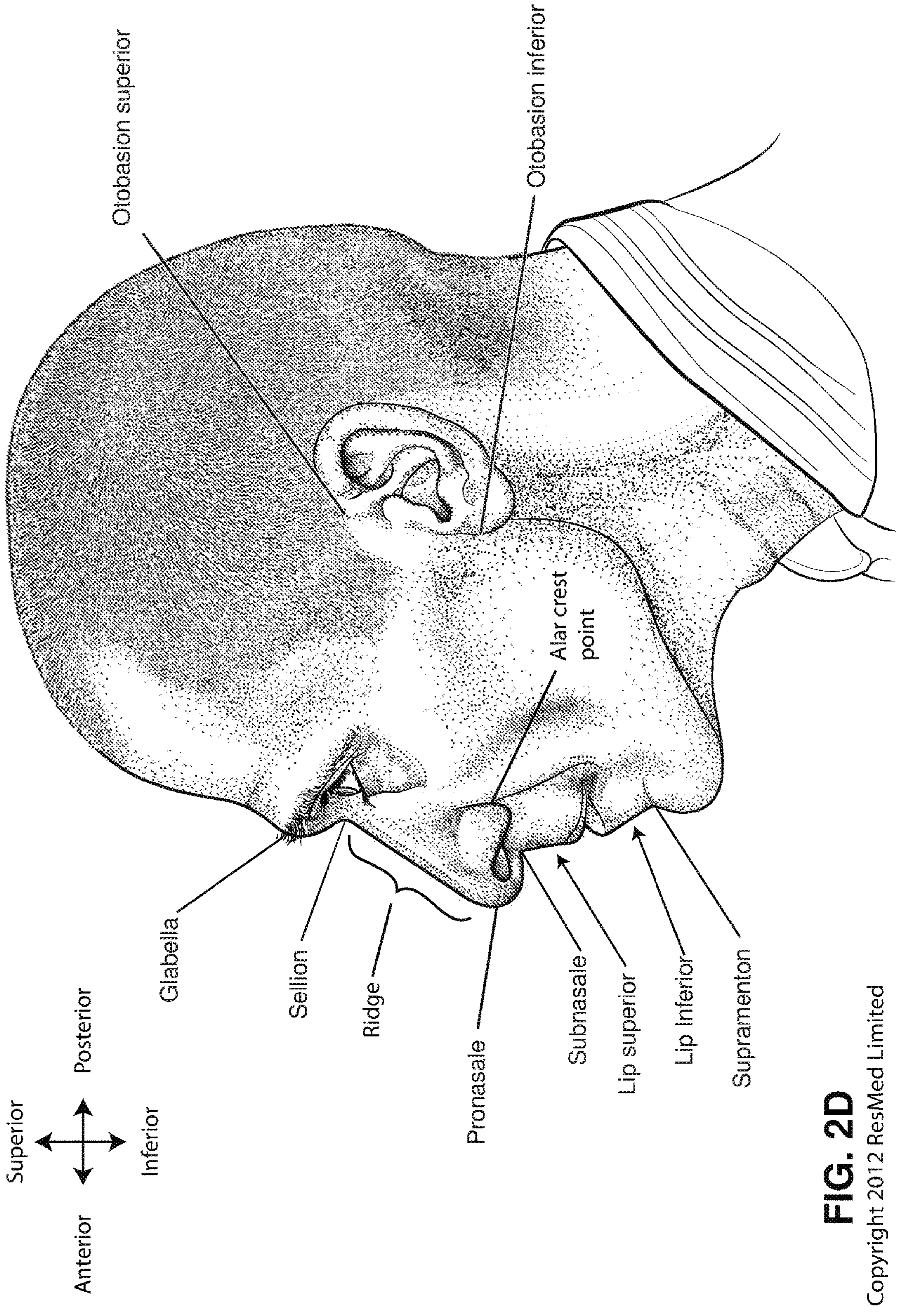
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
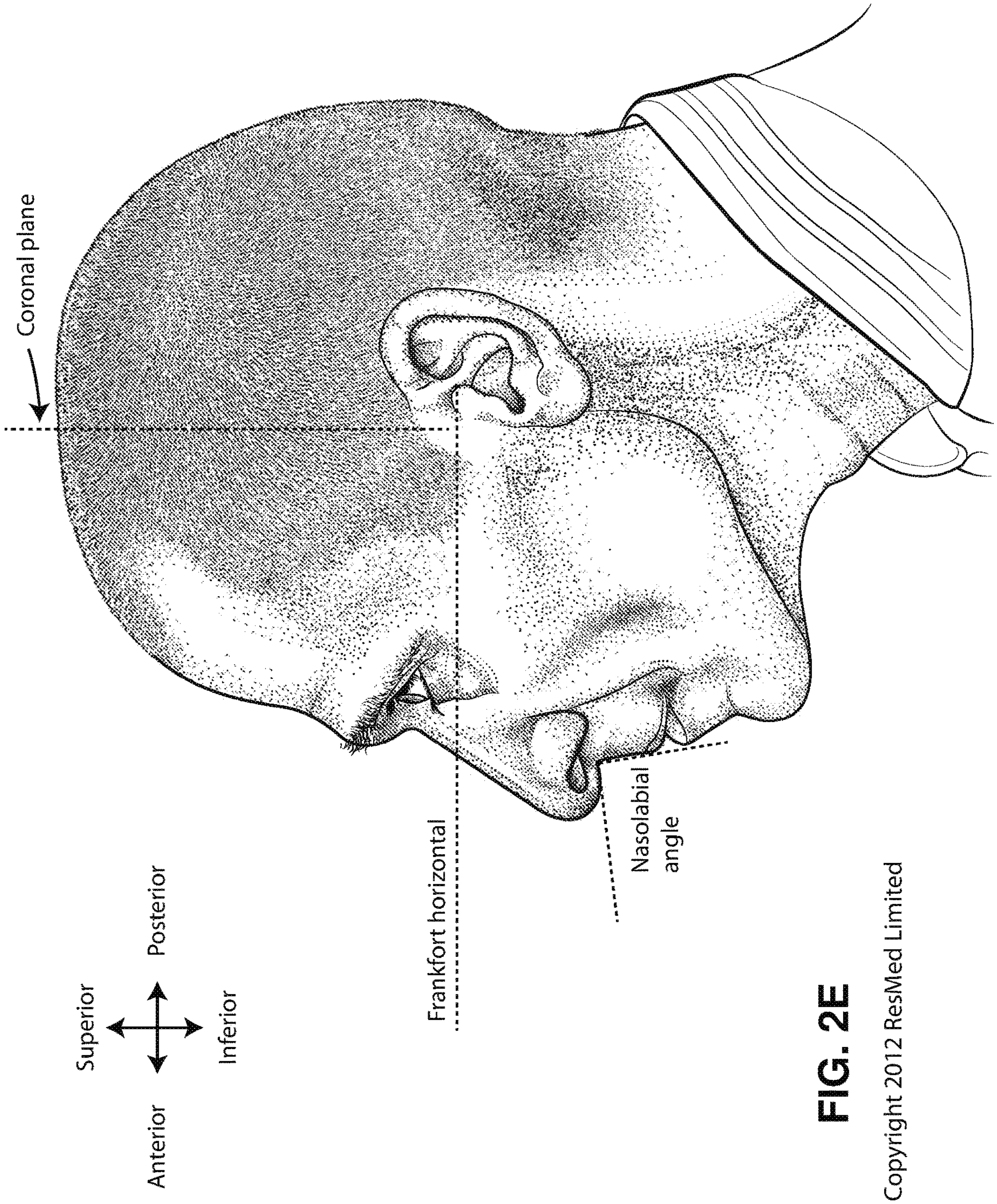

FIG. 2E is a further side view of a head. The approximate locations of the Frankfort horizontal and nasolabial angle are indicated. The coronal plane is also indicated.

Figure 2F:
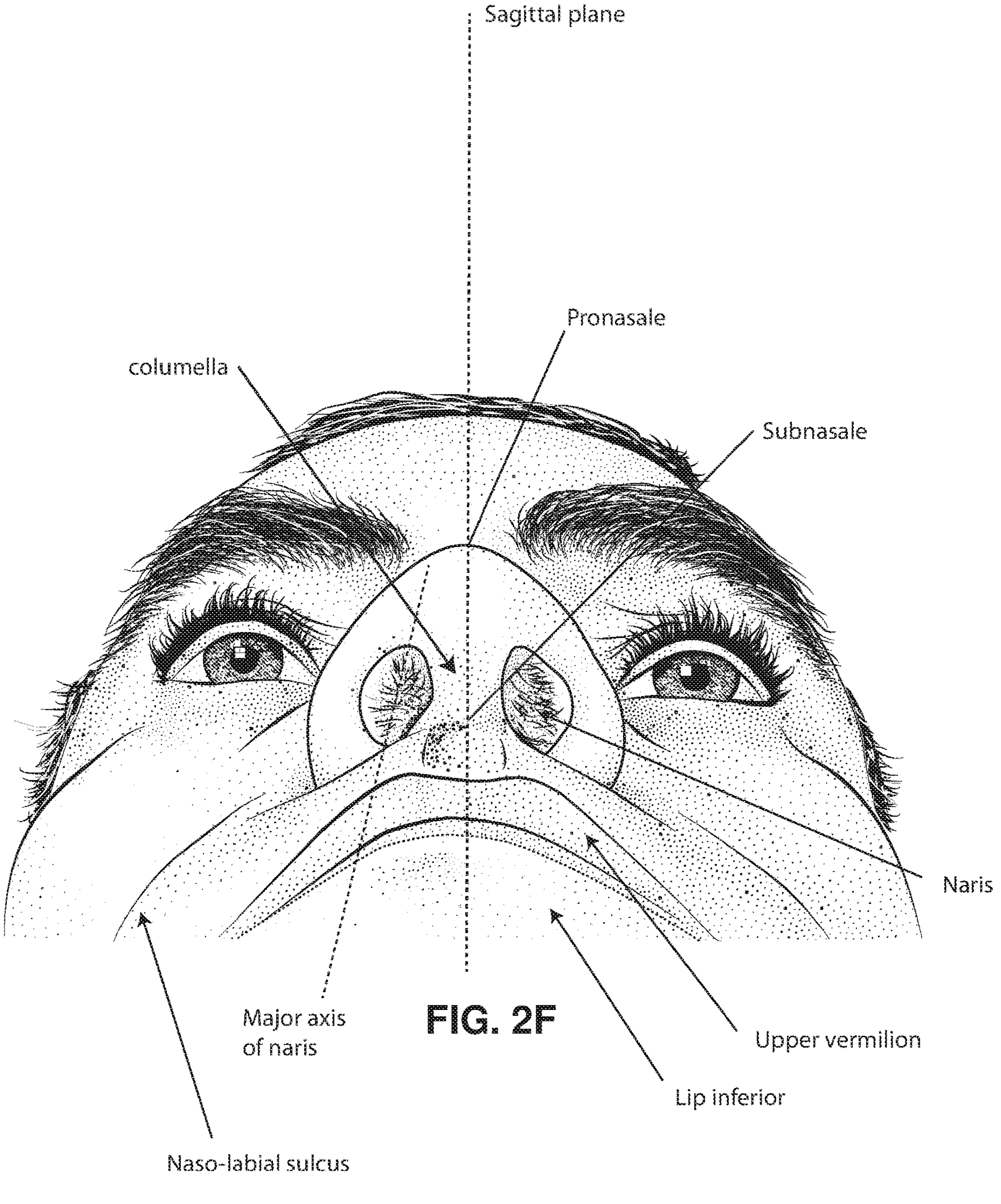

FIG. 2F shows a base view of a nose with several features identified including naso-labial sulcus, lip inferior, upper Vermilion, naris, subnasale, columella, pronasale, the major axis of a naris and the midsagittal plane.

Figure 2I:
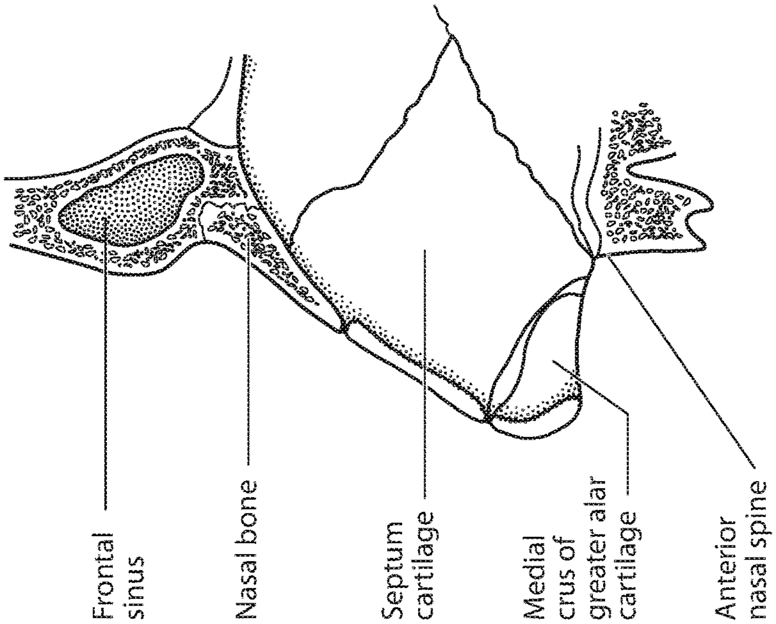
Figure 2H:
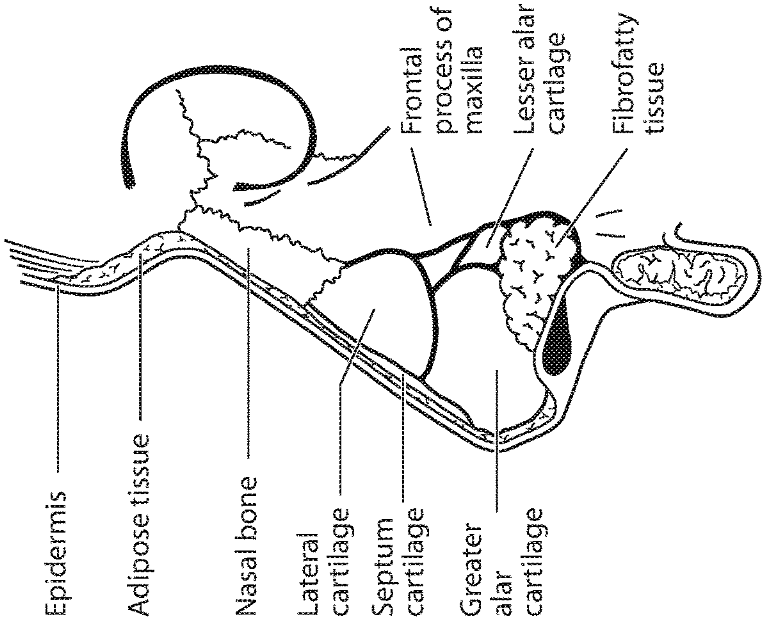
Figure 2G:

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
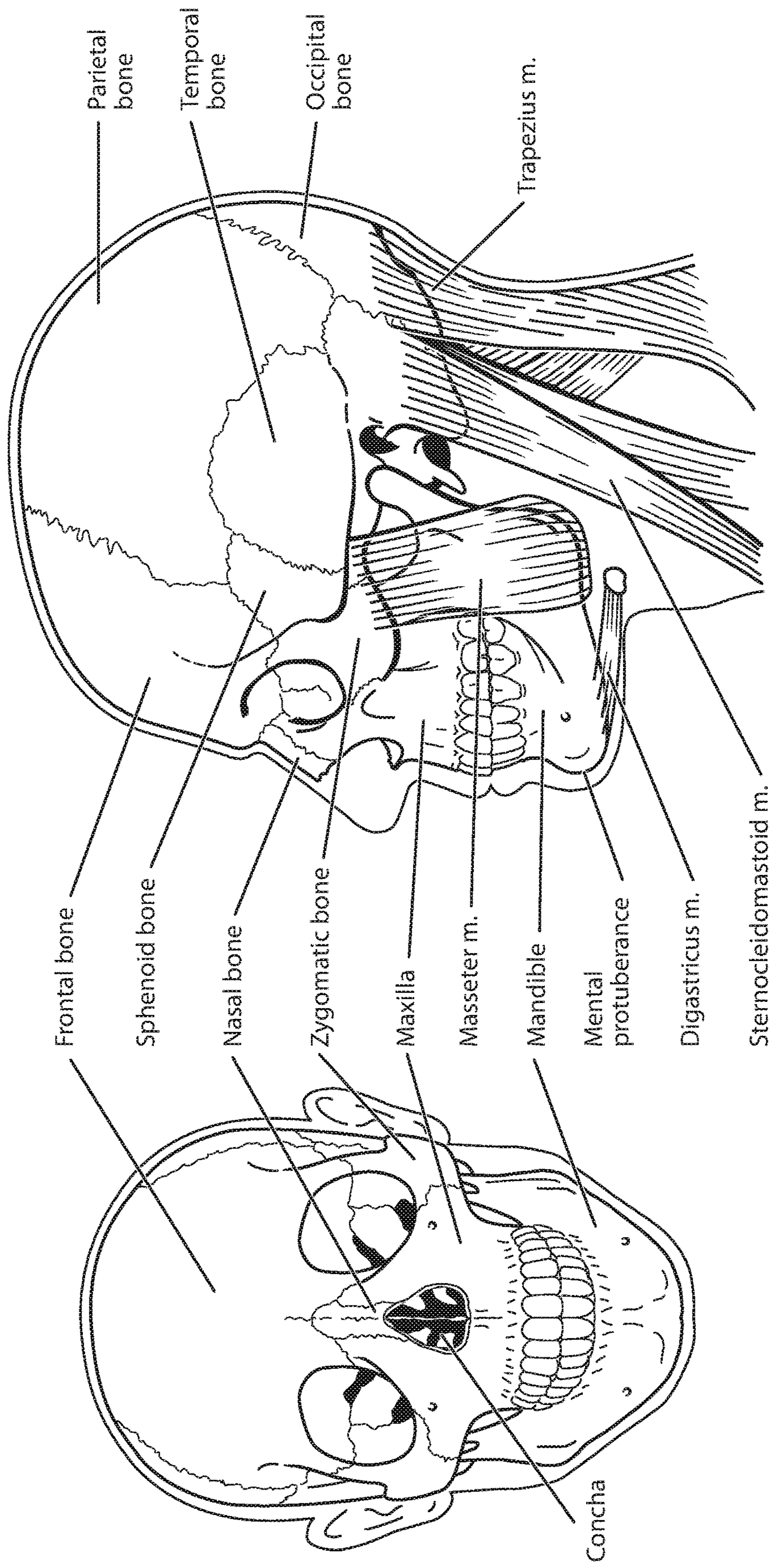

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
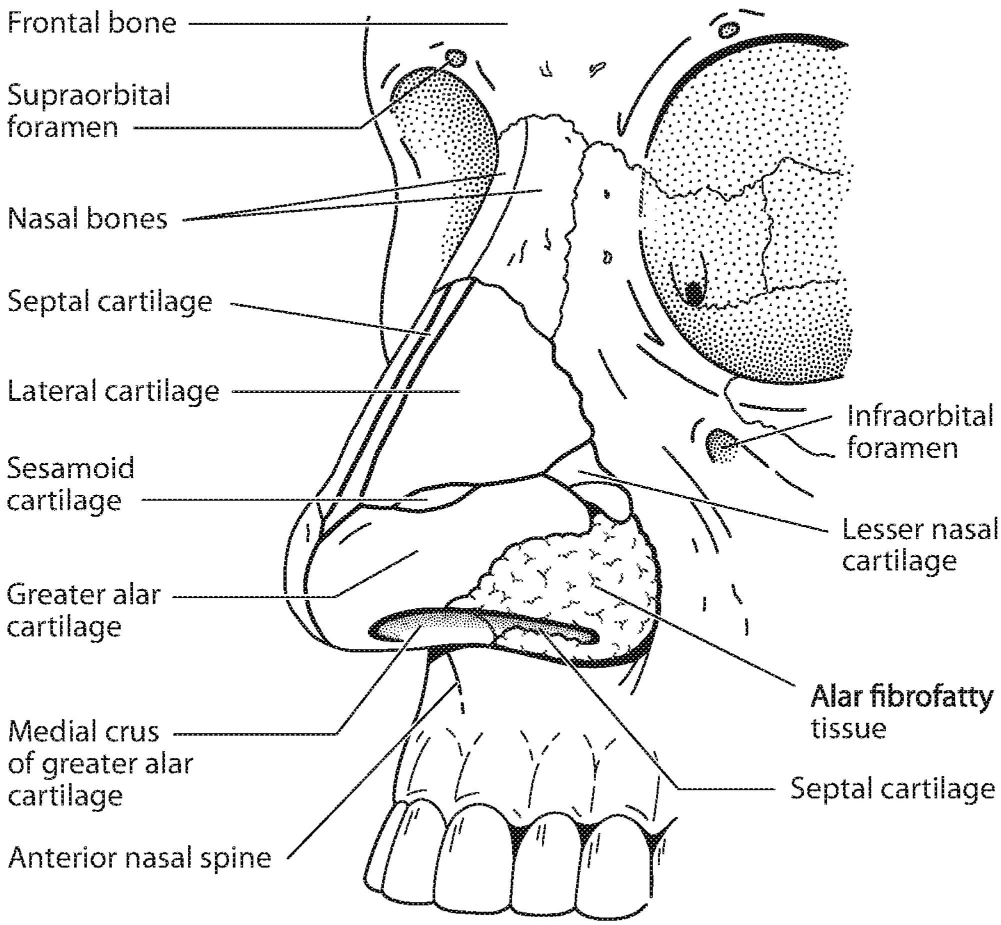

FIG. 2L shows an anterolateral view of a nose.

4.3 Patient Interface

Figure 3A:
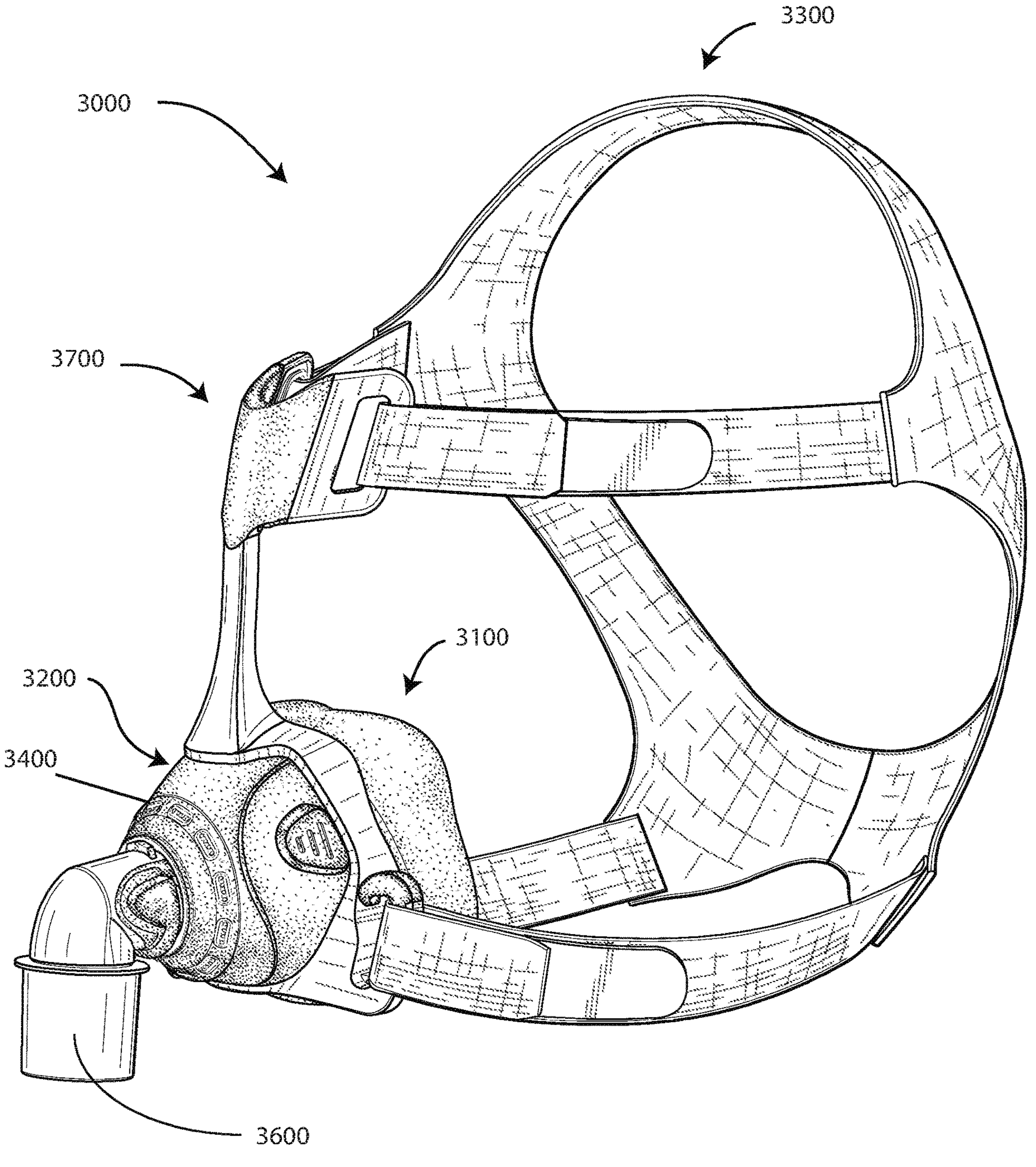

FIG. 3A shows a patient interface in the form of a nasal mask in accordance with one form of the present technology.

Figure 3B:
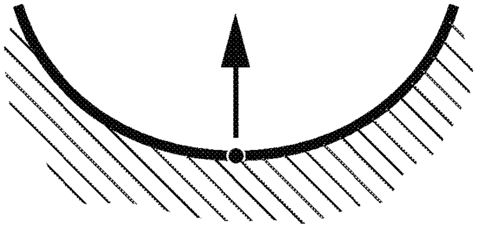

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
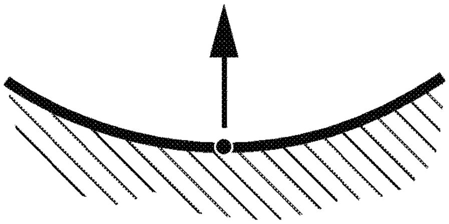

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
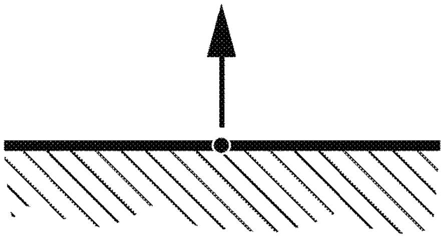

FIG. 3D shows a schematic of a cross-section through a structure at a point. An outward normal at the point is indicated. The curvature at the point has a value of zero.

Figure 3E:
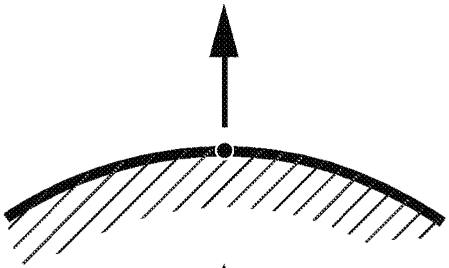

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
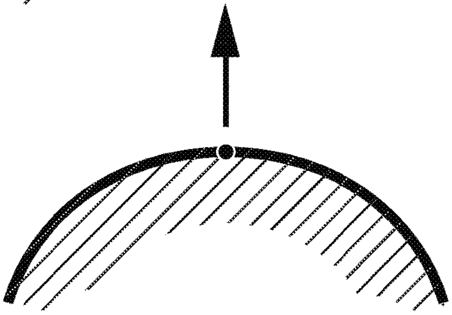

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
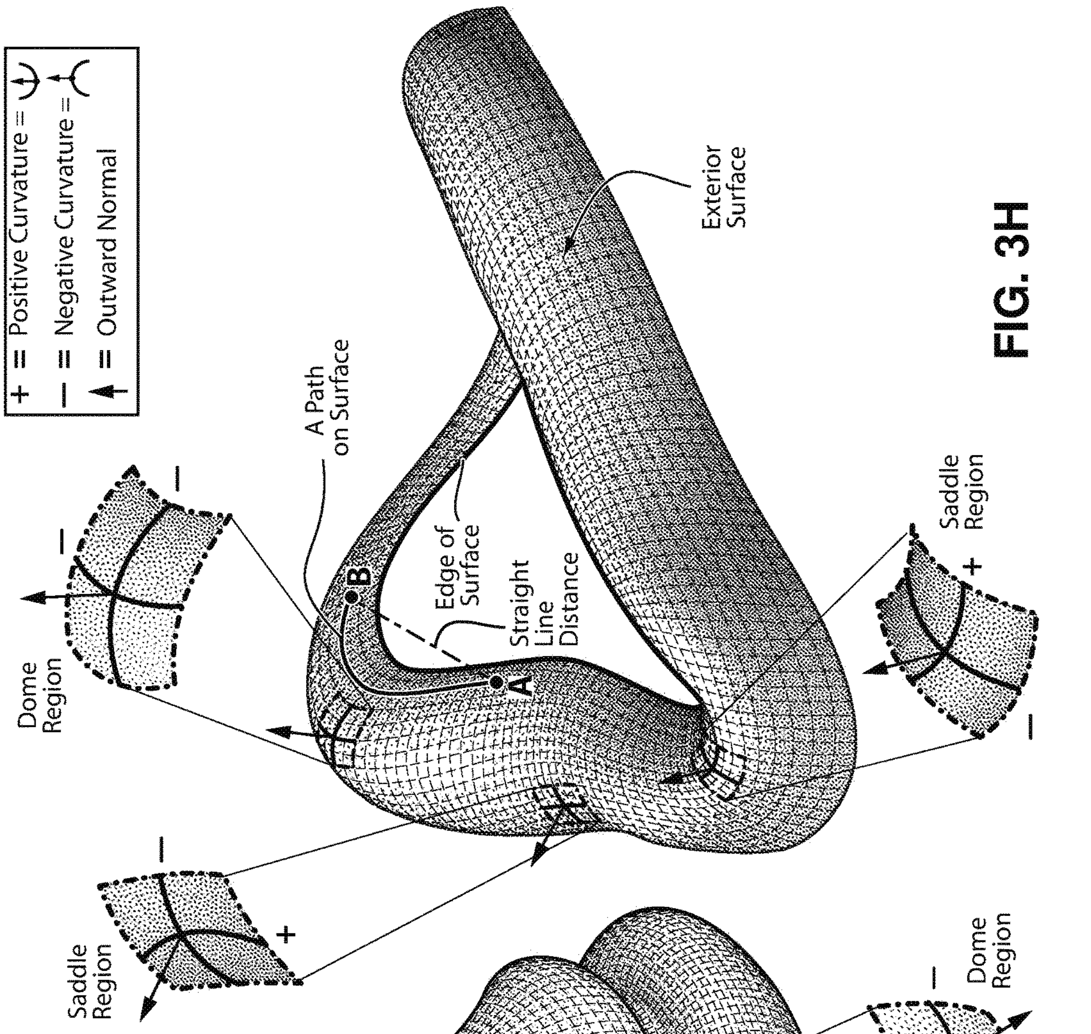
Figure 3G:
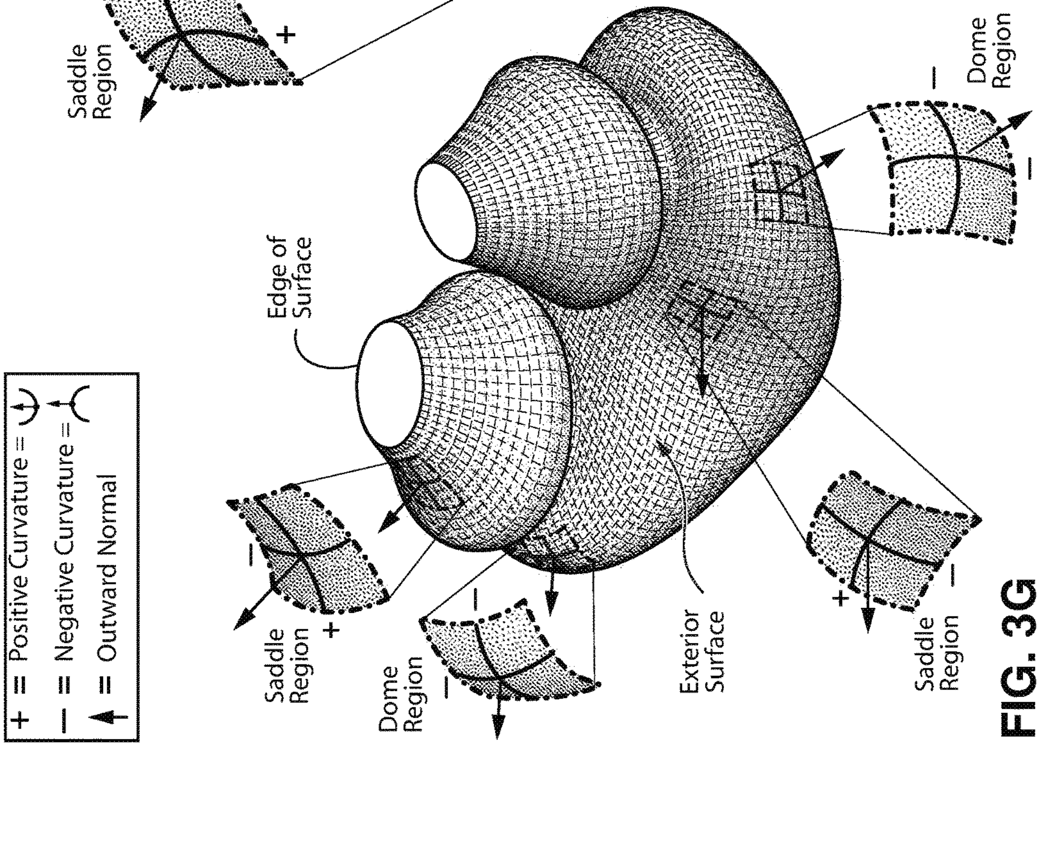

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
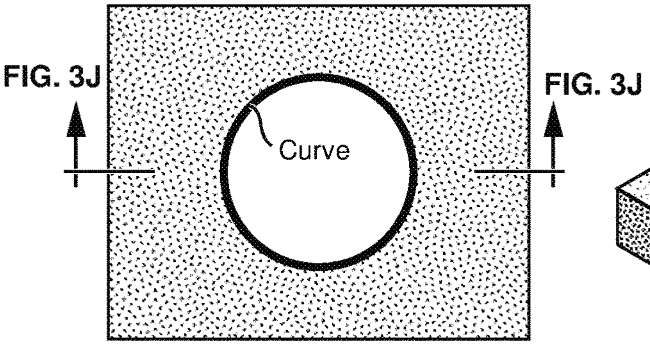

FIG. 3I shows the surface of a structure, with a one dimensional hole in the surface. The illustrated plane curve forms the boundary of a one dimensional hole.

Figure 3K:
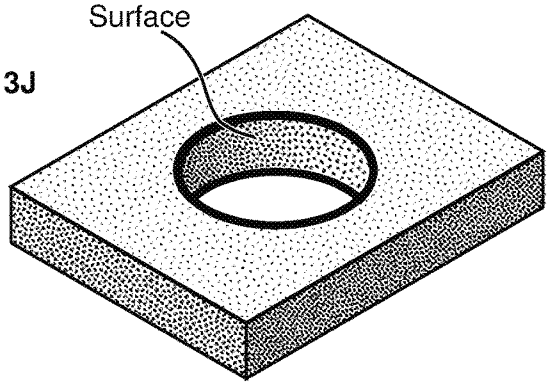
Figure 3J:
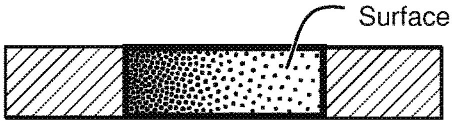

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
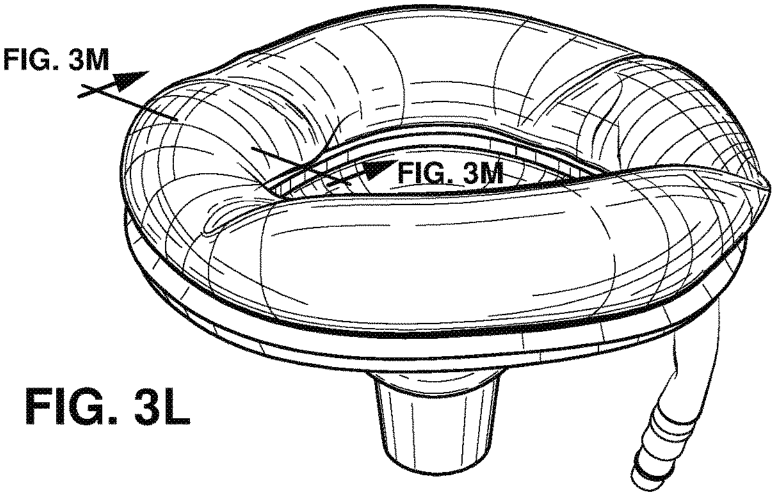

FIG. 3L shows a mask having an inflatable bladder as a cushion.

Figure 3M:
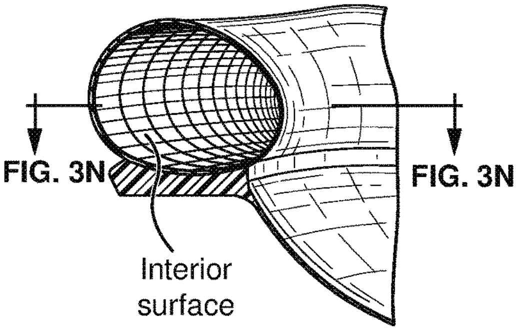

FIG. 3M shows a cross-section through the mask of FIG. 3L, and shows the interior surface of the bladder. The interior surface bounds the two dimensional hole in the mask.

Figure 3N:
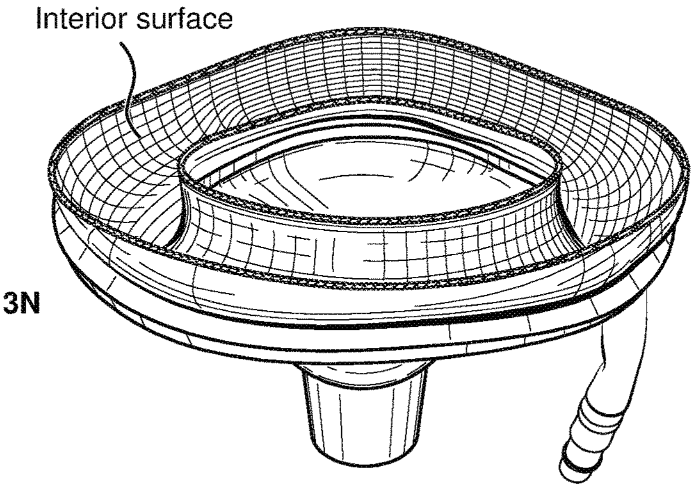

FIG. 3N shows a further cross-section through the mask of FIG. 3L. The interior surface is also indicated.

Figure 3O:
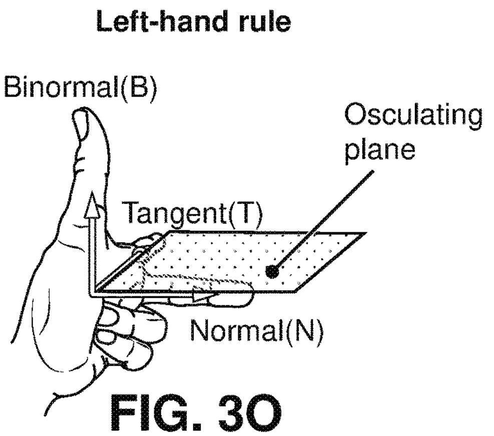

FIG. 3O illustrates a left-hand rule.

Figure 3P:
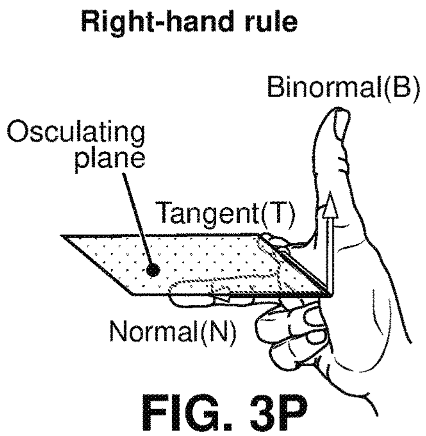

FIG. 3P illustrates a right-hand rule.

Figure 3Q:
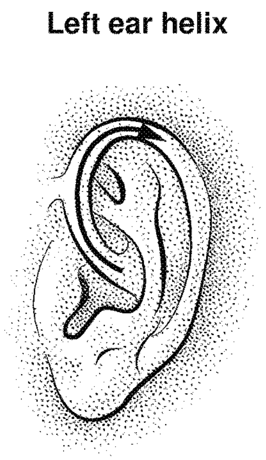

FIG. 3Q shows a left ear, including the left ear helix.

Figure 3S:
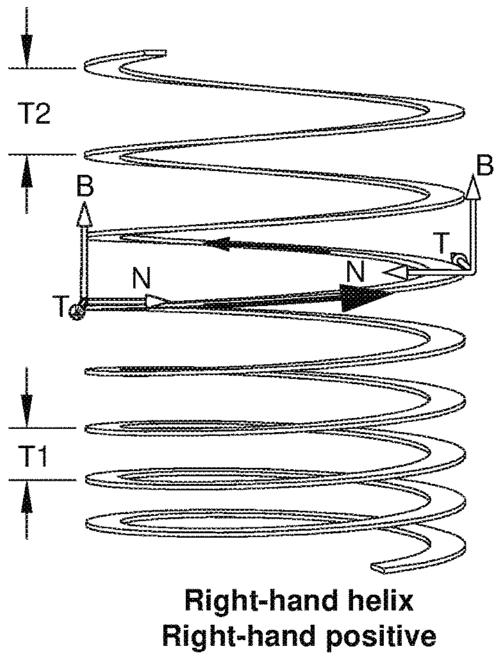
Figure 3R:
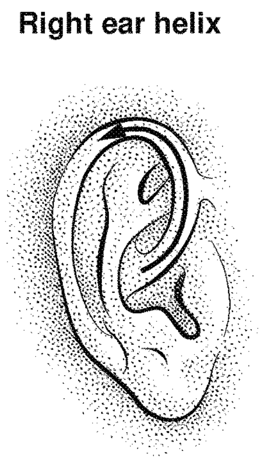

FIG. 3R shows a right ear, including the right ear helix.

FIG. 3S shows a right-hand helix.

Figure 3T:
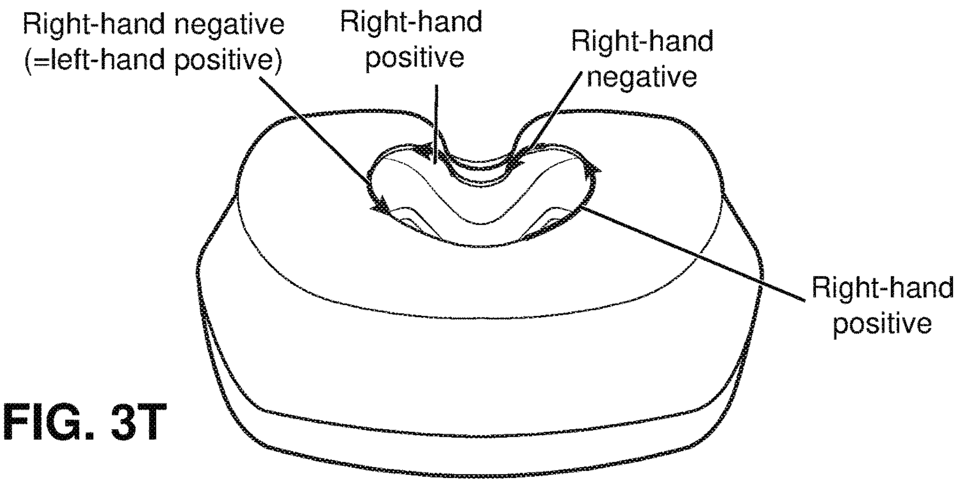

FIG. 3T shows a view of a mask, including the sign of the torsion of the space curve defined by the edge of the sealing membrane in different regions of the mask.

Figure 3U:
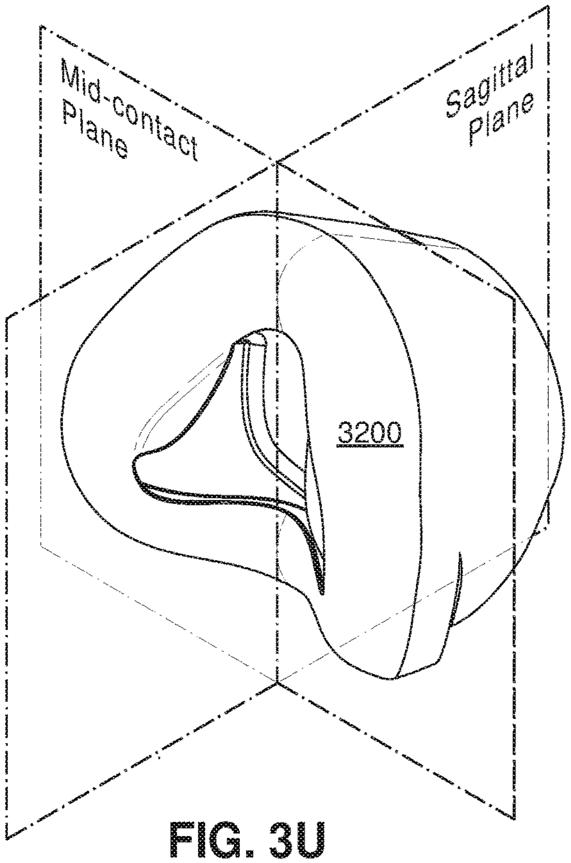

FIG. 3U shows a view of a plenum chamber 3200 showing a sagittal plane and a mid-contact plane.

Figure 3V:
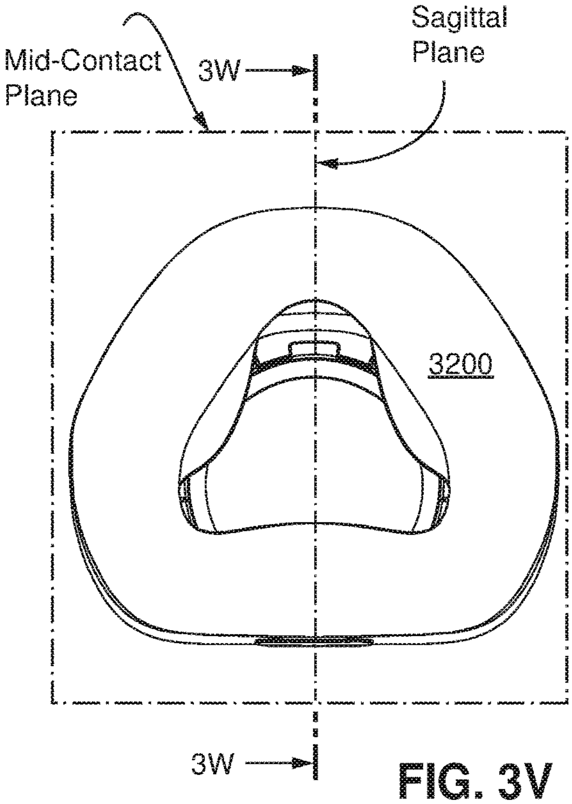

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
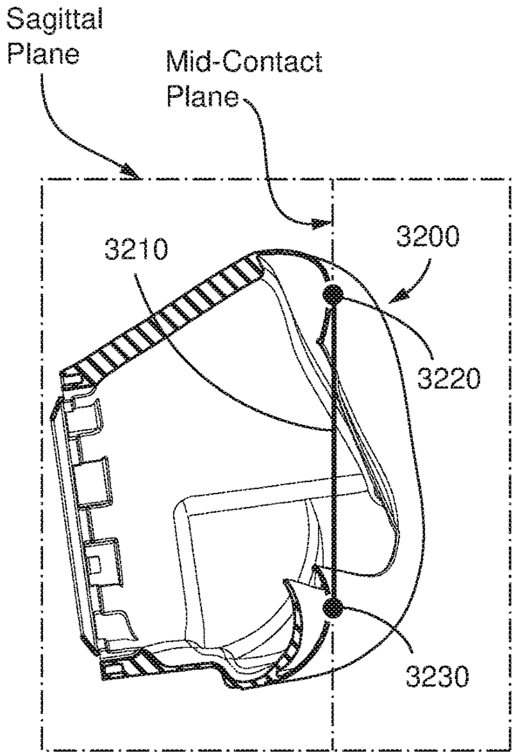

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
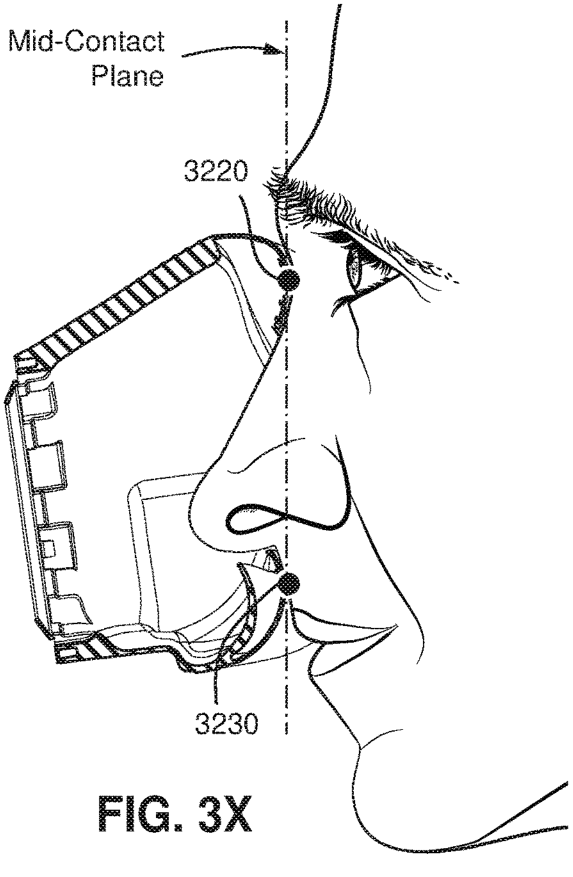

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
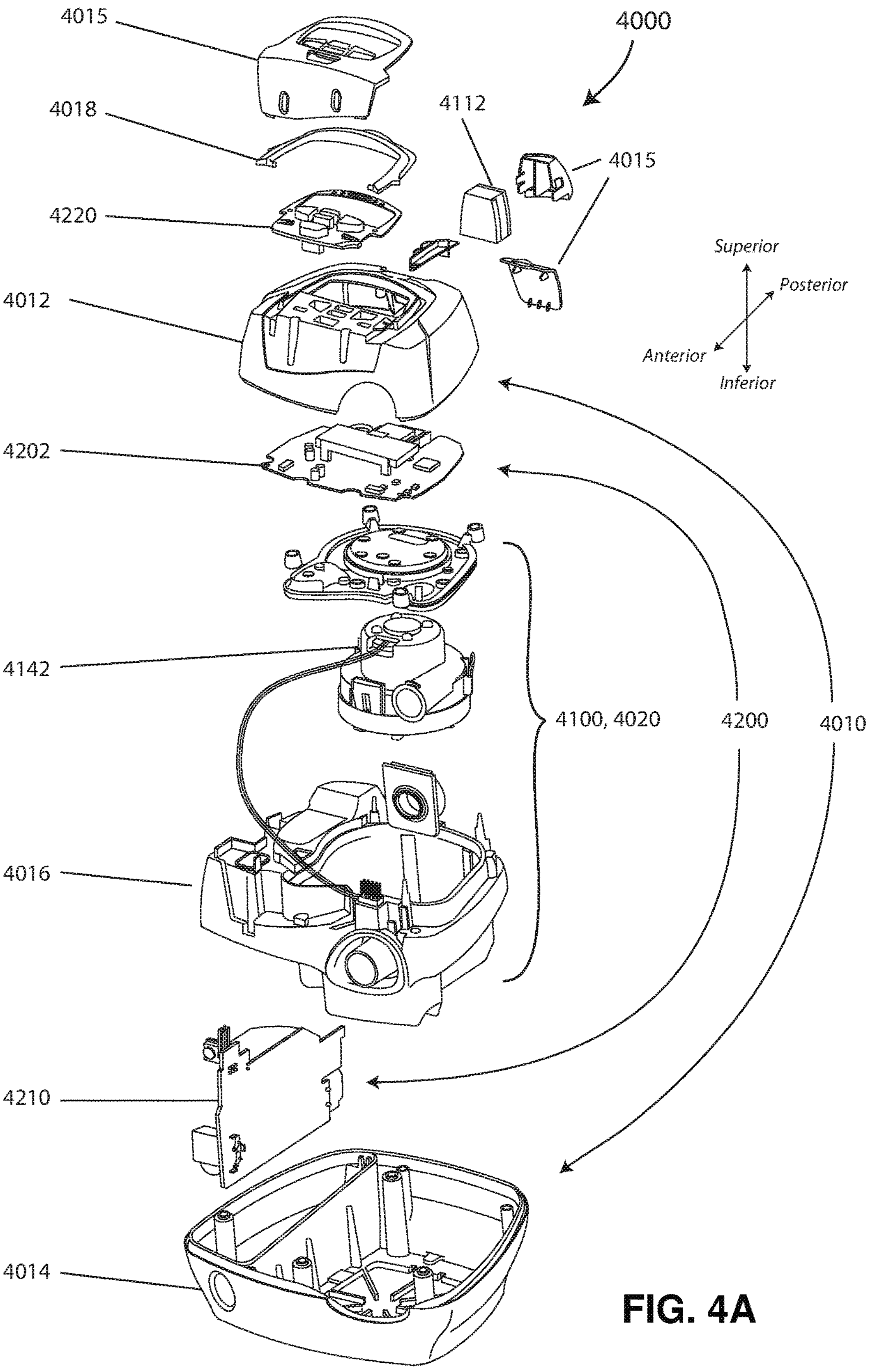

FIG. 4A shows an RPT device in accordance with one form of the present technology.

Figure 4B:
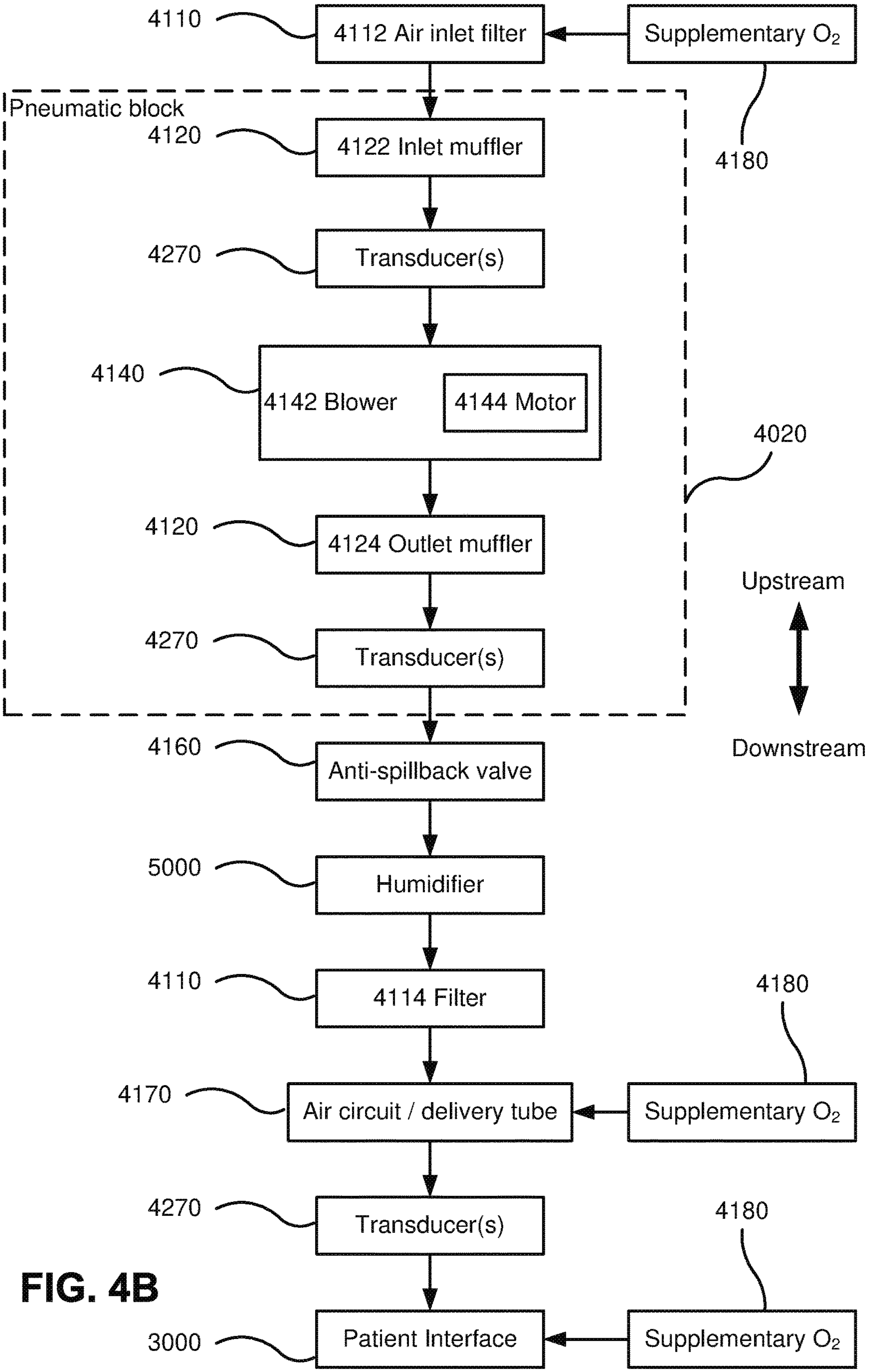

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
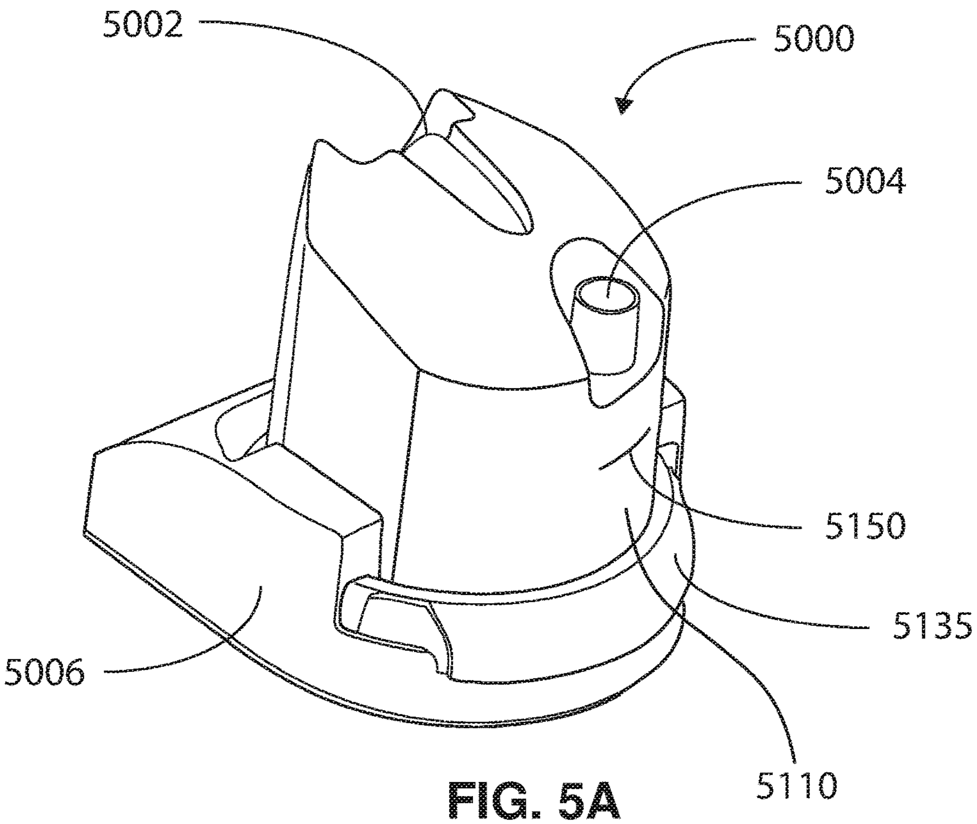

FIG. 5A shows an isometric view of a humidifier in accordance with one form of the present technology.

Figure 5B:
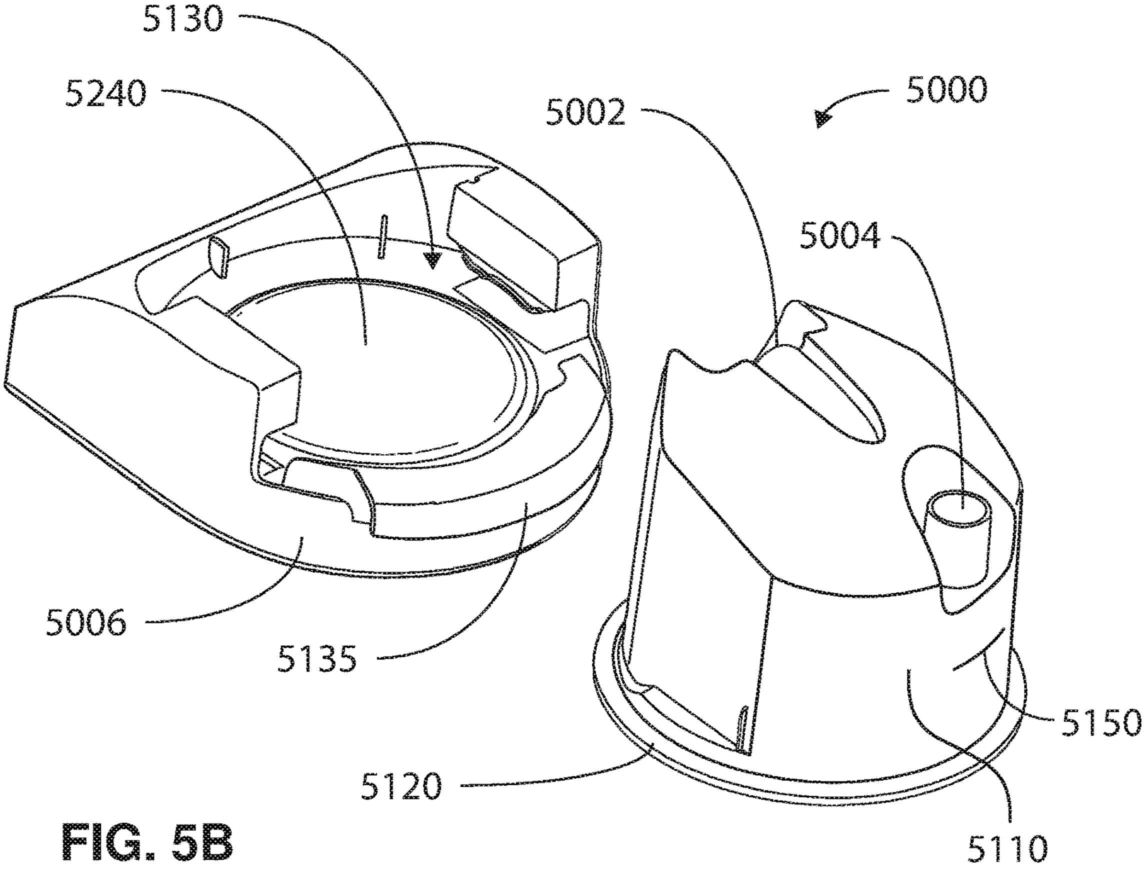

FIG. 5B shows an isometric view of a humidifier in accordance with one form of the present technology, showing a humidifier reservoir 5110 removed from the humidifier reservoir dock 5130.

4.6 Breathing Waveforms

Figure 6:
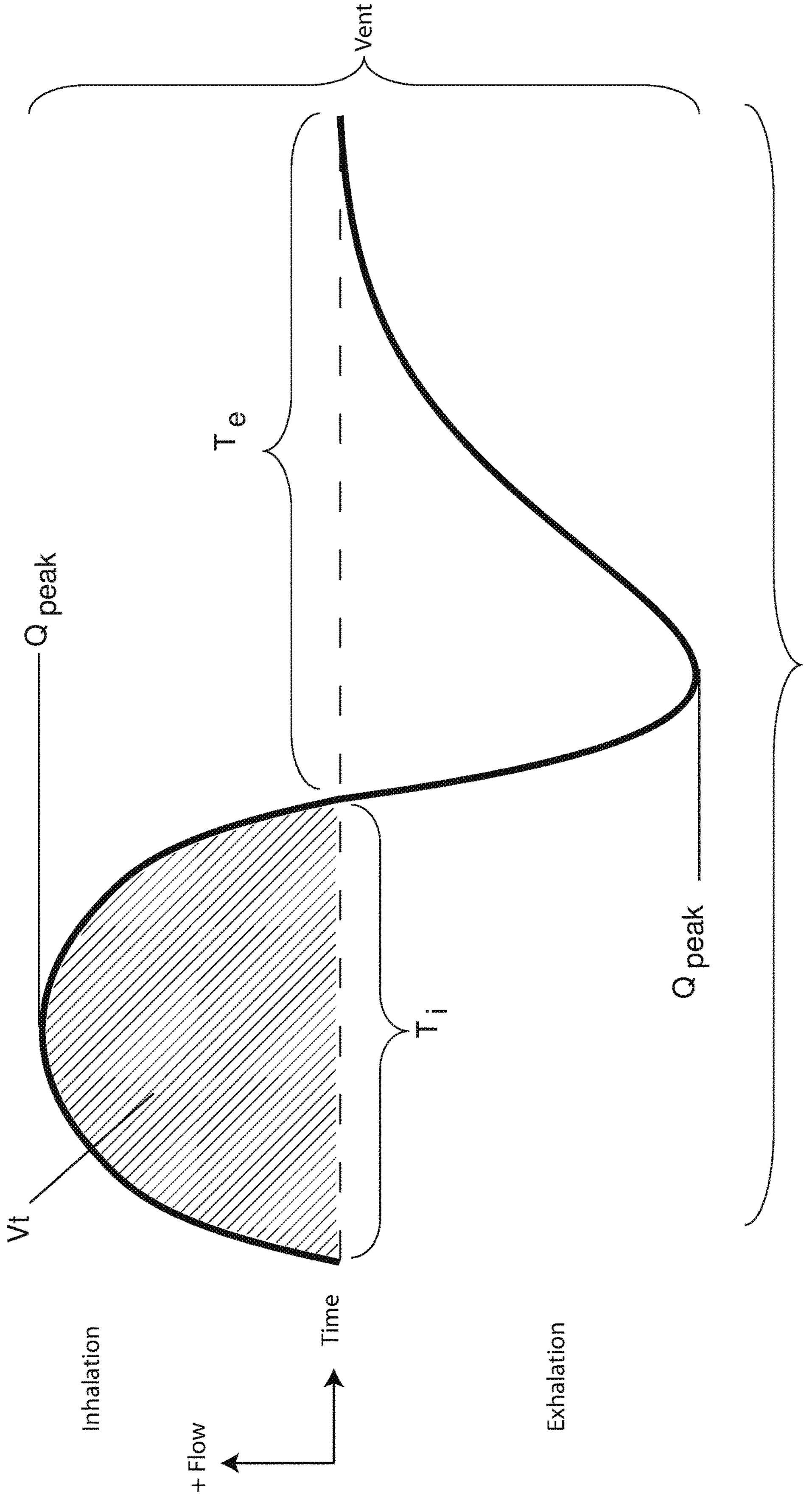

FIG. 6 shows a model typical breath waveform of a person while sleeping.

4.7 Particular Examples of the Present Technology

Figure 7:
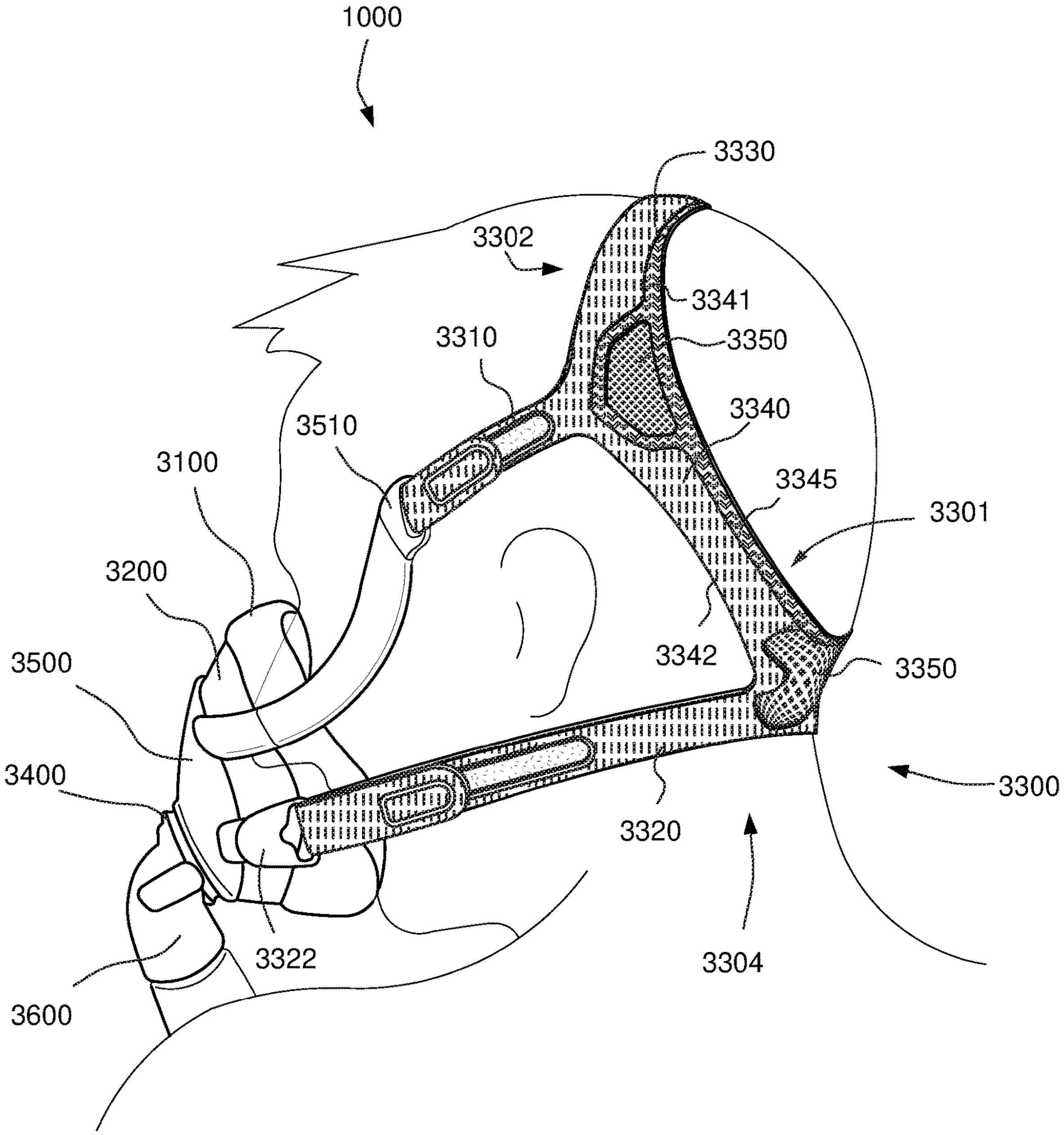

FIG. 7 shows a perspective view of a positioning and stabilising structure 3300 according to one example of the present technology, while donned by a patient 1000.

Figure 8:
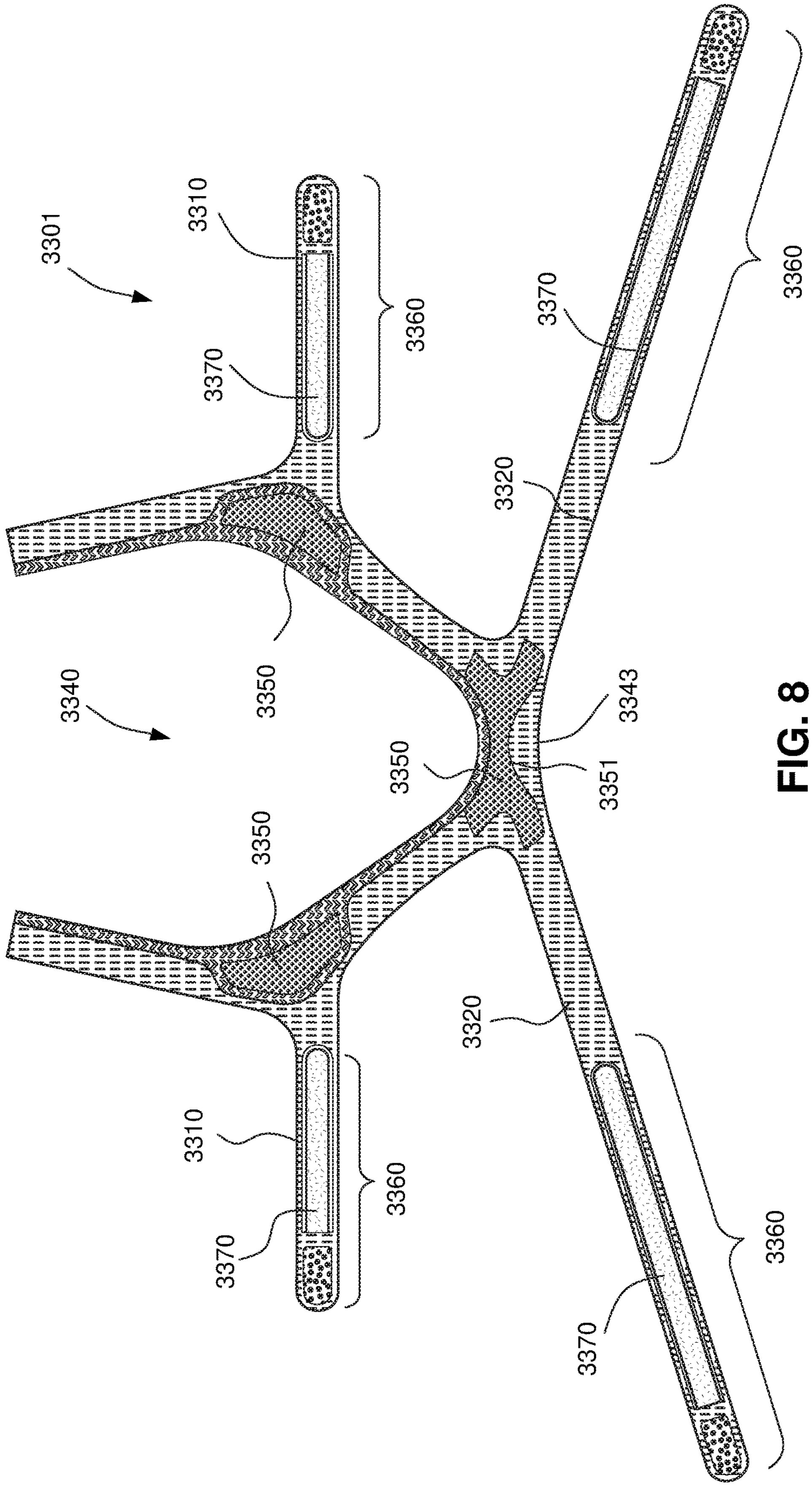

FIG. 8 shows a non-patient-contacting side view of strap portions of the positioning and stabilising structure 3300 of FIG. 7 in a flattened state.

Figure 9:
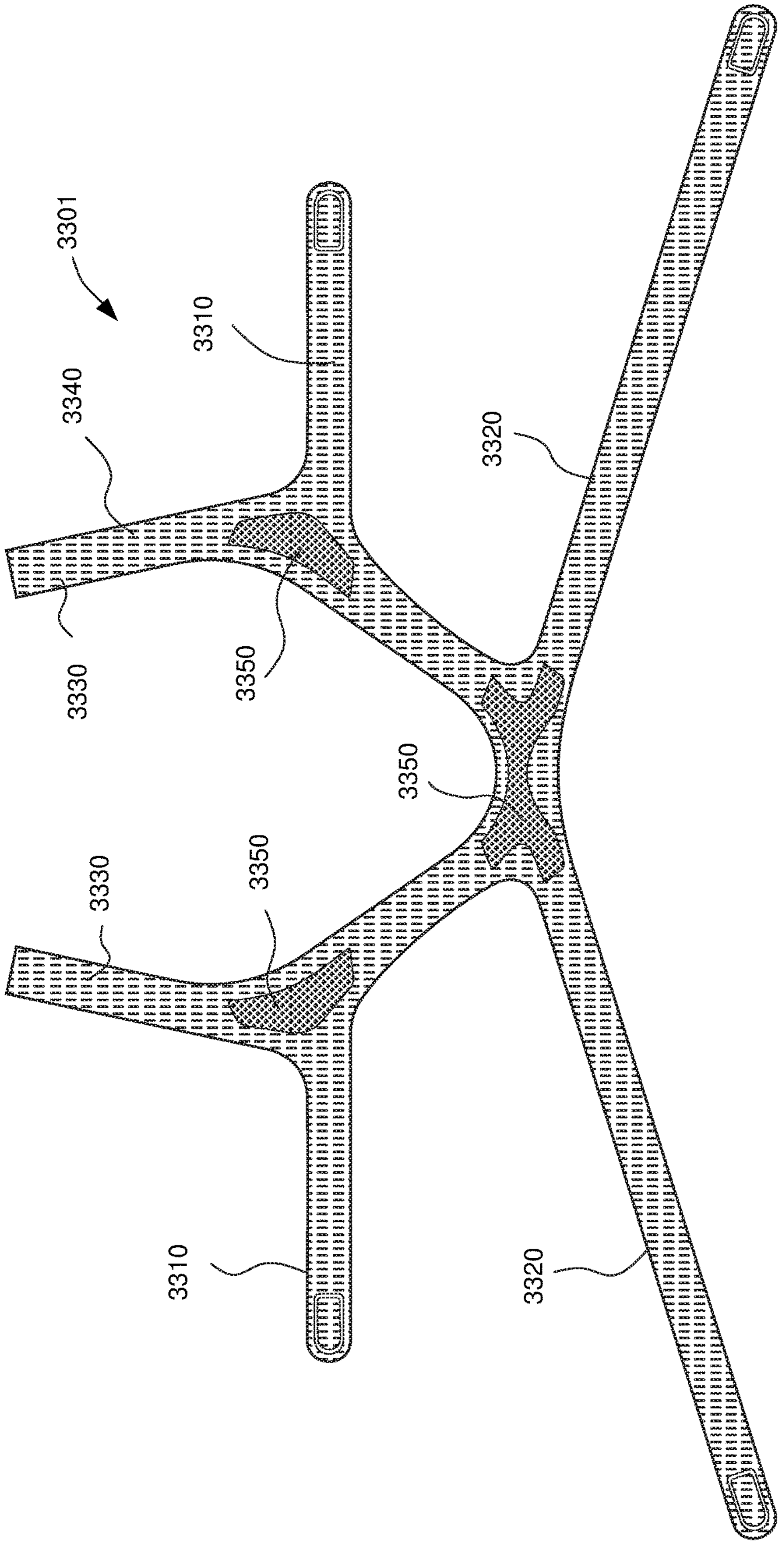

FIG. 9 shows a patient-contacting side view of strap portions of the positioning and stabilising structure 3300 of FIG. 7 in a flattened state.

Figure 10:
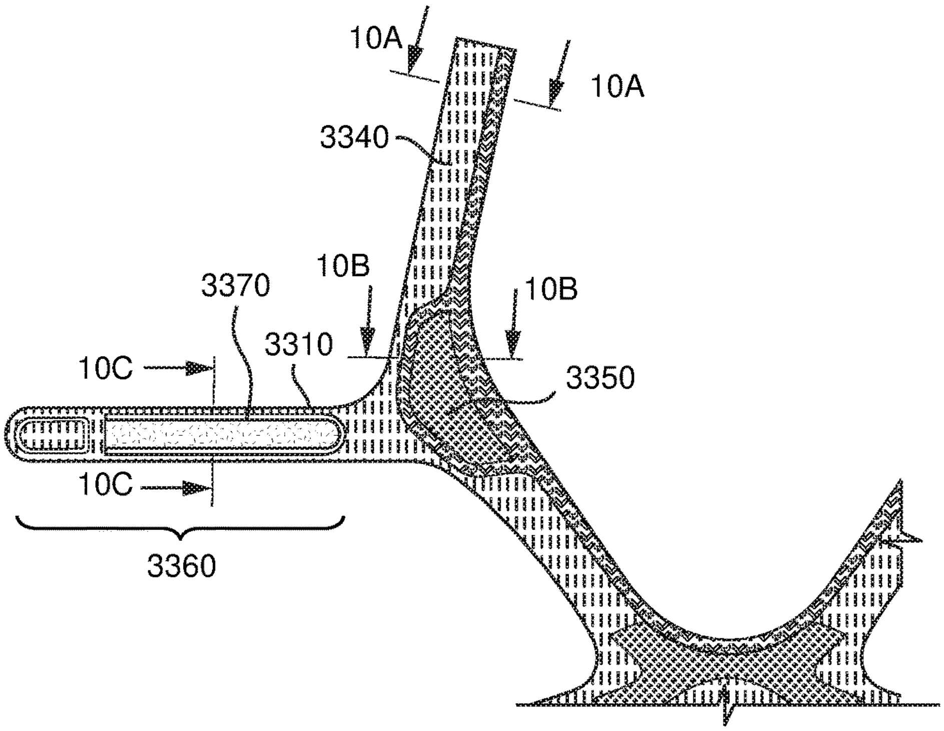
Figure 10A:
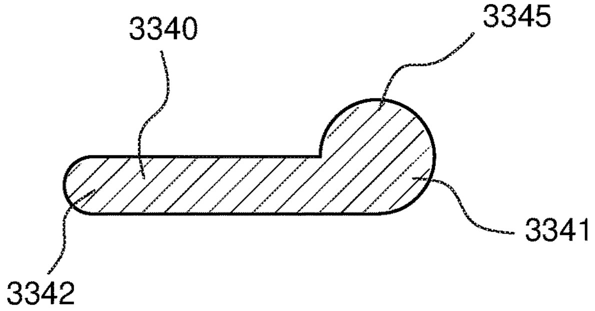
Figure 10B:
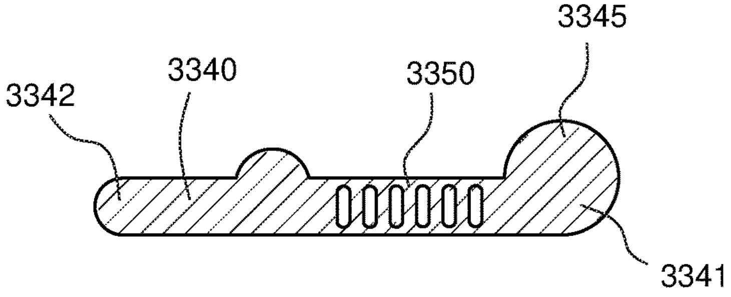
Figure 10C:
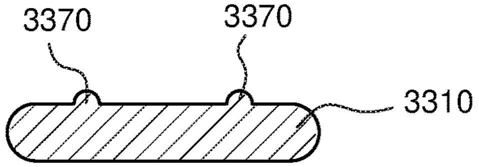

FIG. 10 shows a non-patient-contacting side view of a portion of the positioning and stabilising structure 3300 of FIG. 7 in a flattened state and with cross sections illustrated.

Figure 11:
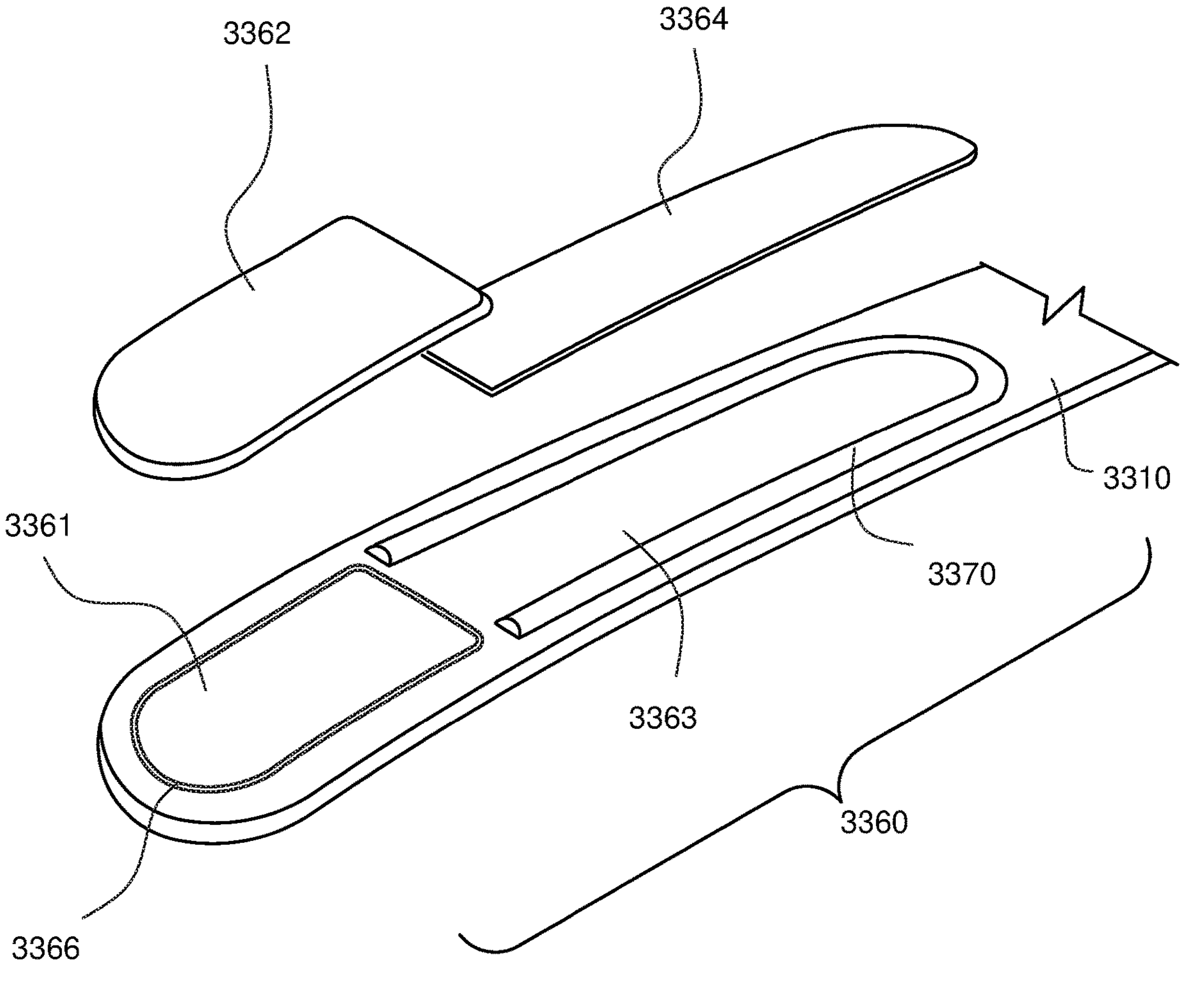

FIG. 11 shows an exploded view of a fastening portion of a strap of the positioning and stabilising structure 3300 of FIG. 7.

Figure 12:
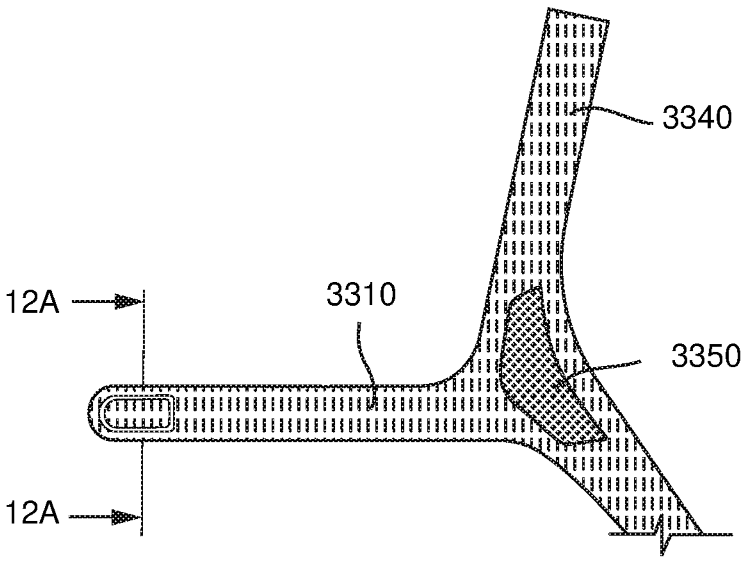
Figure 12A:
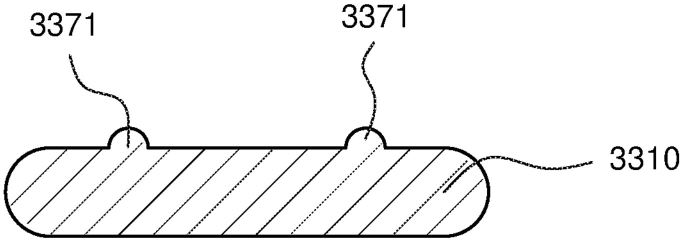

FIG. 12 shows a patient-contacting side view of a portion of the positioning and stabilising structure 3300 of FIG. 7 in a flattened state and with a cross section illustrated.

Figure 13:
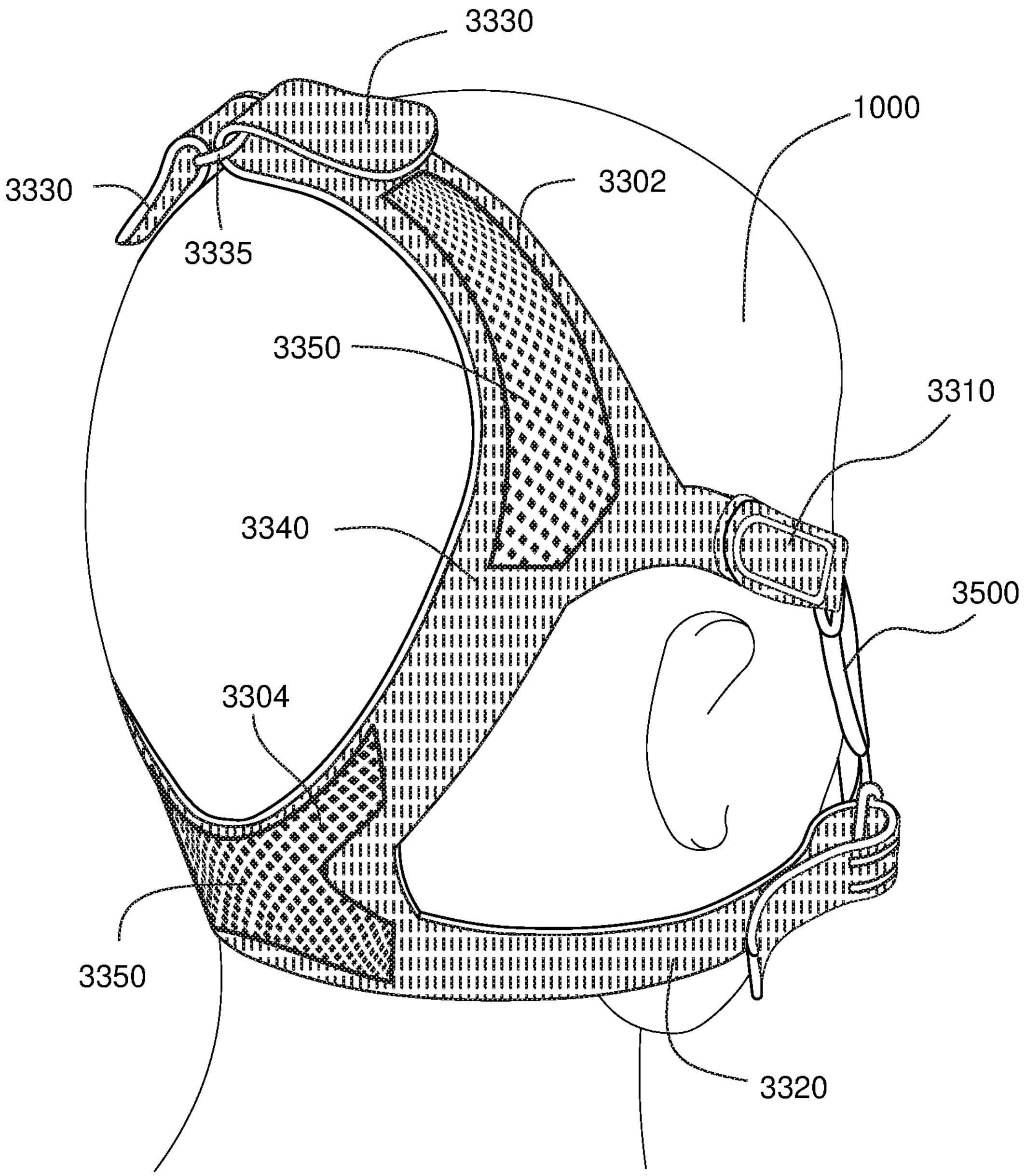

FIG. 13 shows a portion of a positioning and stabilising portion 3300 according to another example of the present technology, while donned by a patient 1000.

Figure 14:
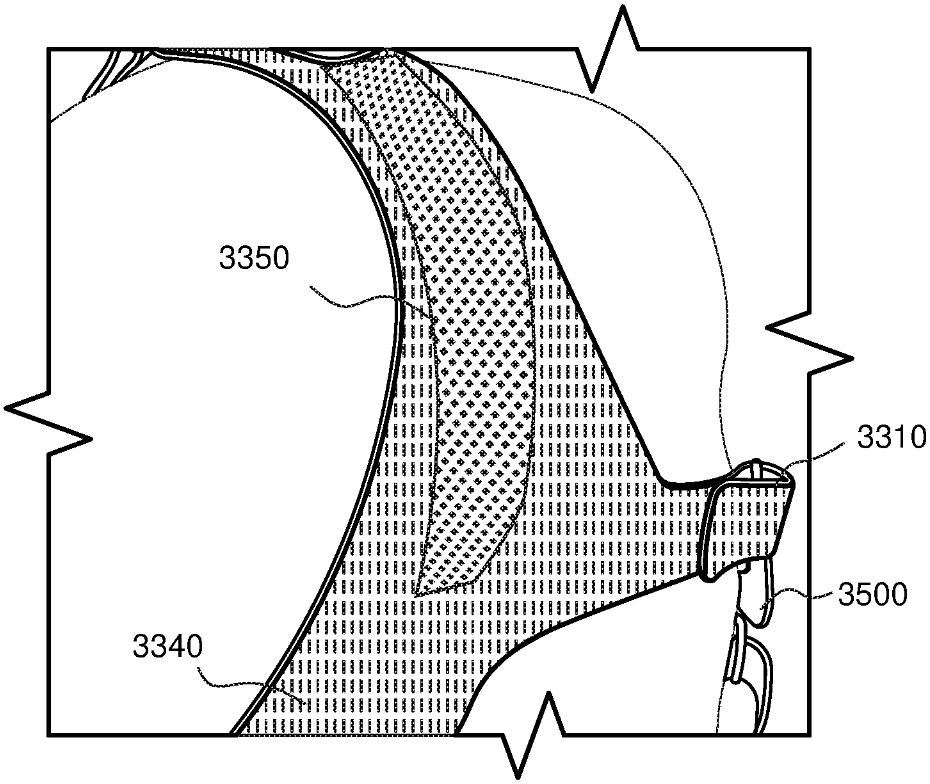

FIG. 14 shows a superior ventilation portion of the positioning and stabilising structure of FIG. 13, while donned by a patient 1000.

Figure 15:
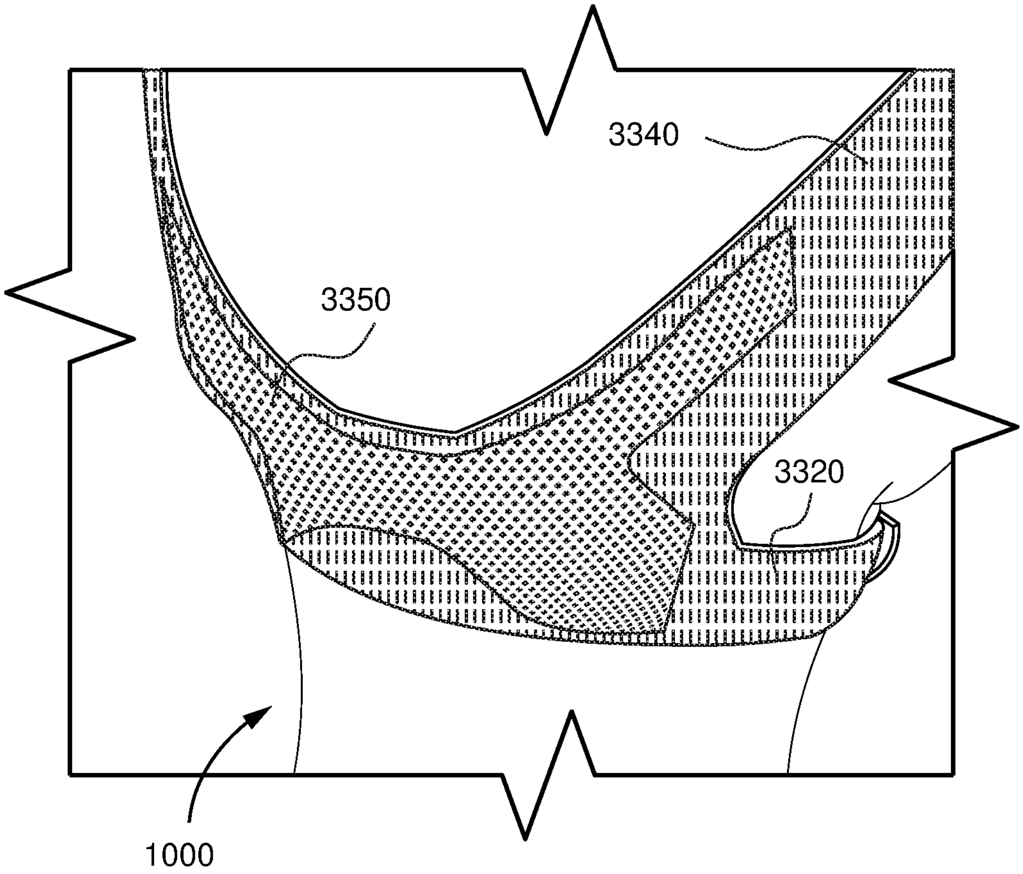

FIG. 15 shows an inferior ventilation portion of the positioning and stabilising structure of FIG. 13 while donned by a patient 1000.

Figure 16:
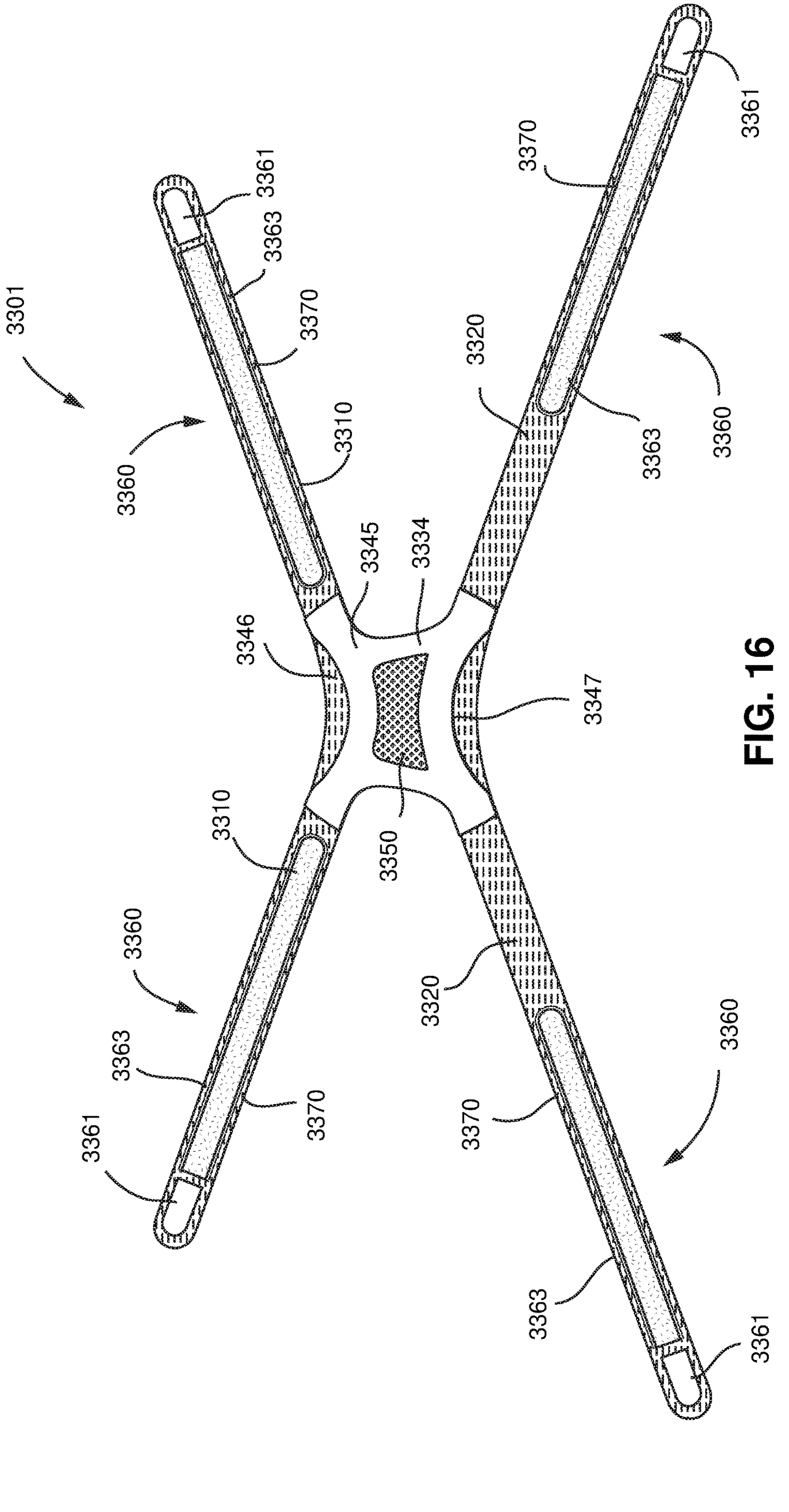

FIG. 16 shows a non-patient-contacting side view of a headgear strap 3301 of a positioning and stabilising structure according to another example of the present technology.

Figure 17:
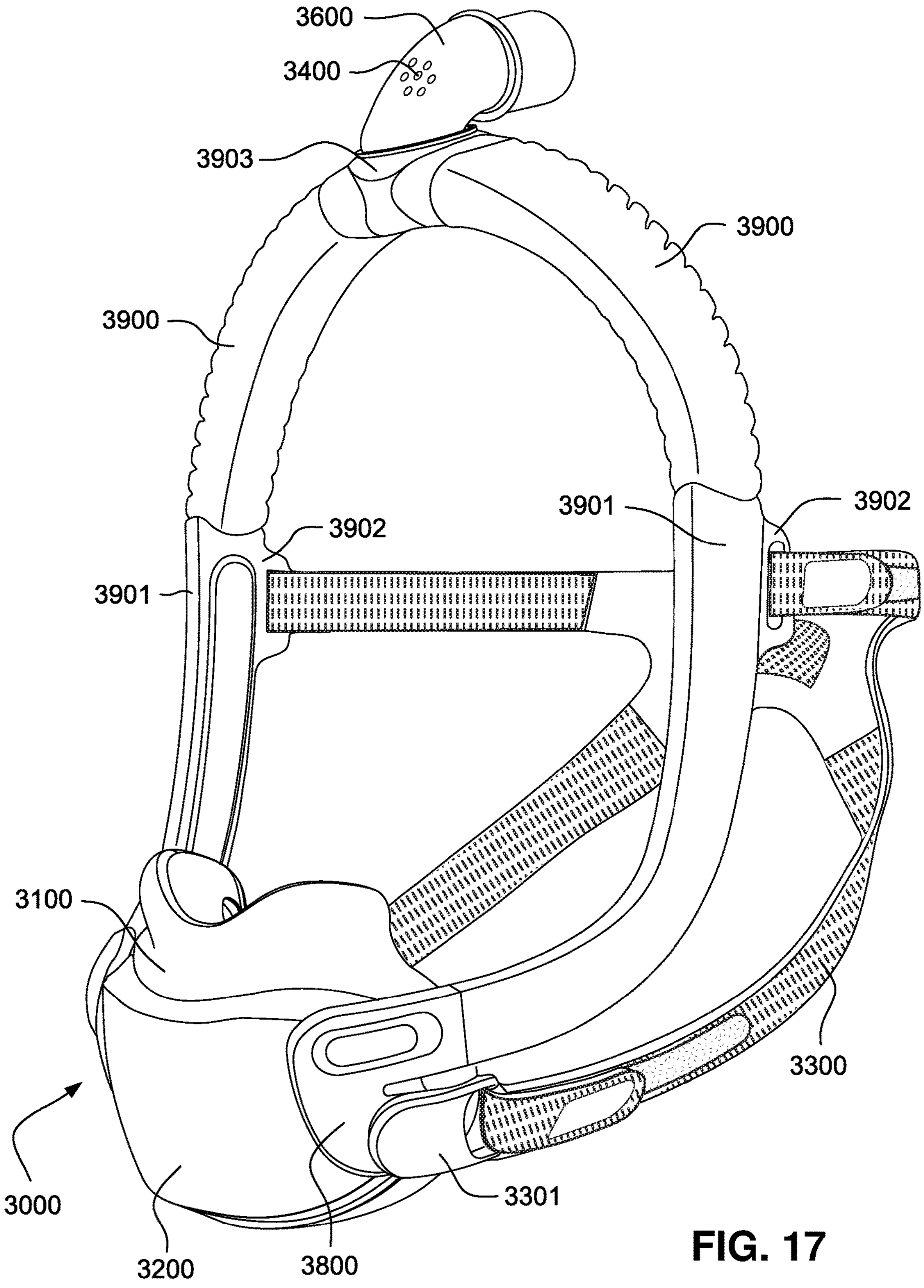

FIG. 17 shows a perspective view of a patient interface 3000 according to another example of the present technology, comprising the headgear strap 3301 of FIG. 16.

Figure 18:
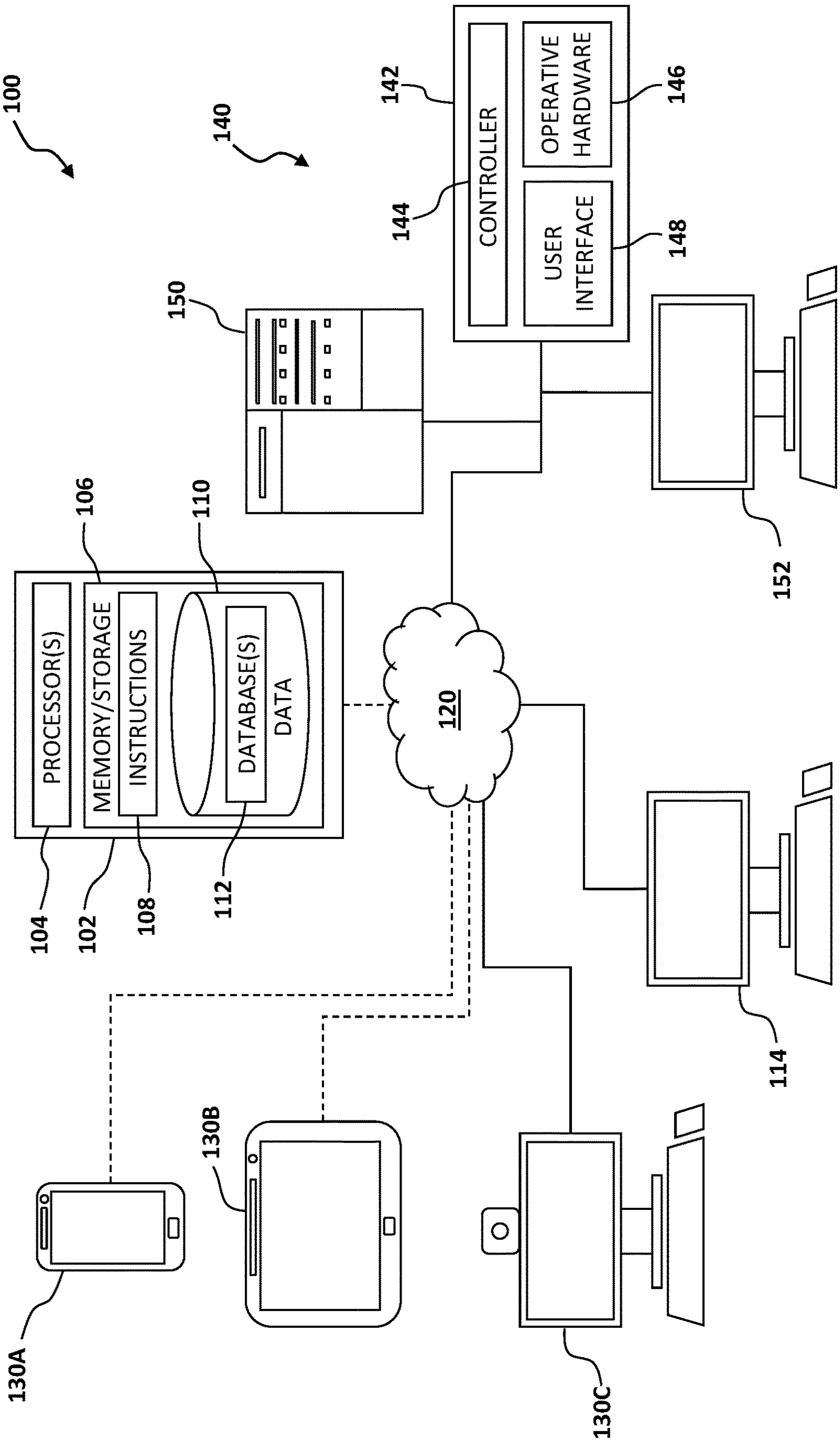

FIG. 18 shows a schematic view of a system 300 according to another example of the present technology.

FIG. 19A to 19F show flow charts of a method 7000 and aspects thereof according to another example of the present technology.

Figure 20:
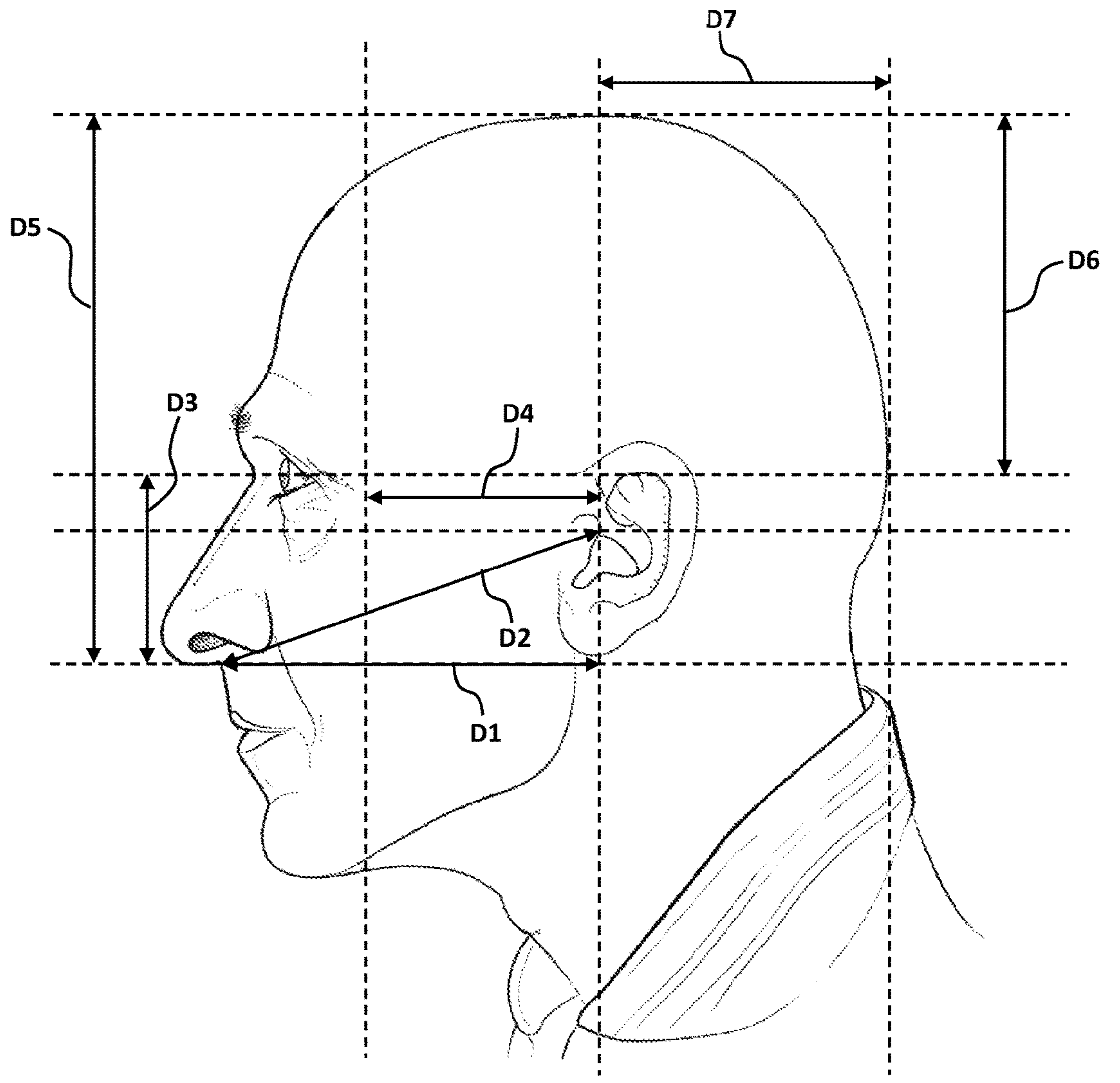

FIG. 20 shows a side view of a patient's head having a number of distances identified, relevant to the method 7000.

Figure 21:
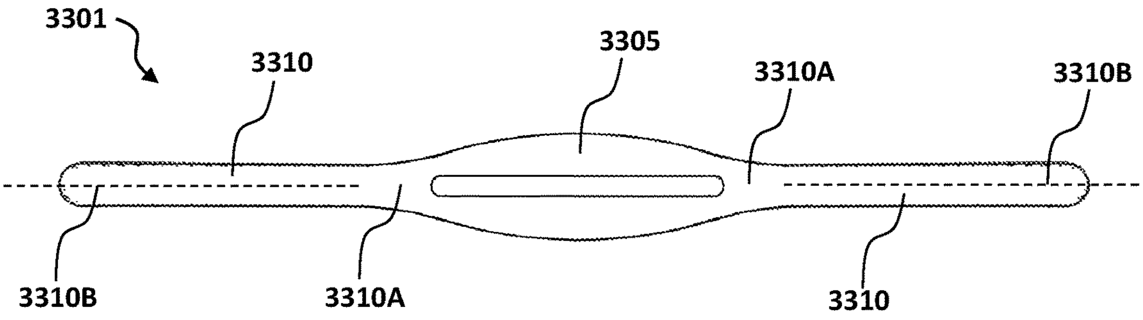

FIG. 21 shows a plan view of a headgear strap 3301 in a flattened state, according to another example of the present technology.

Figure 22:
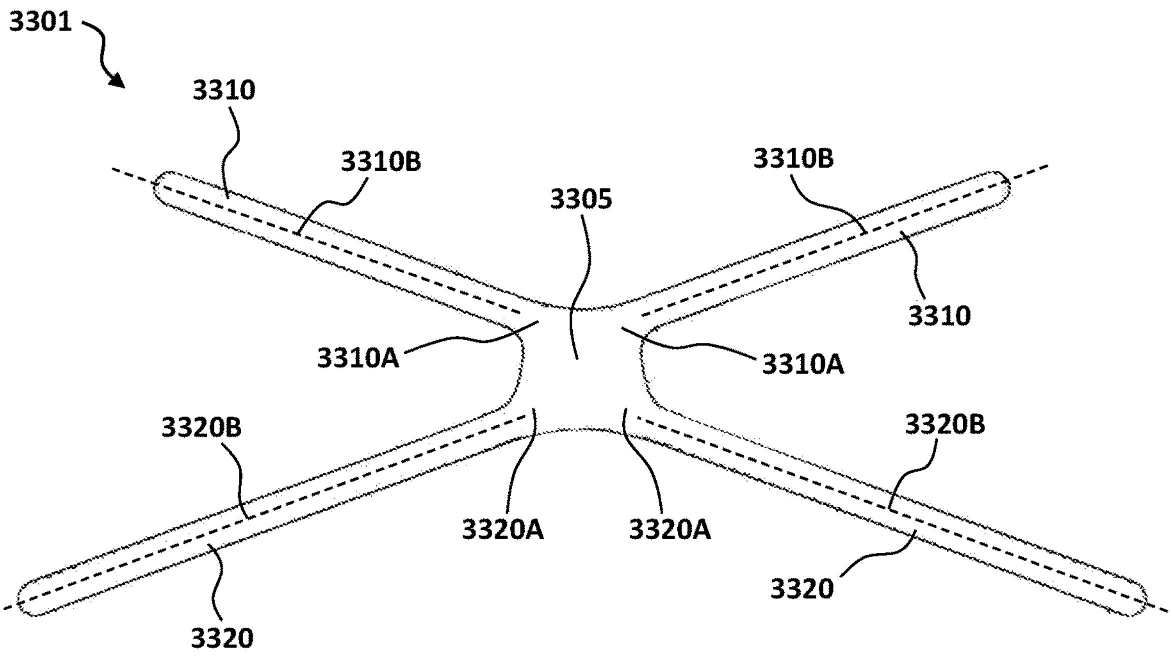

FIG. 22 shows a plan view of a headgear strap 3301 in a flattened state, according to another example of the present technology.

Figure 23:
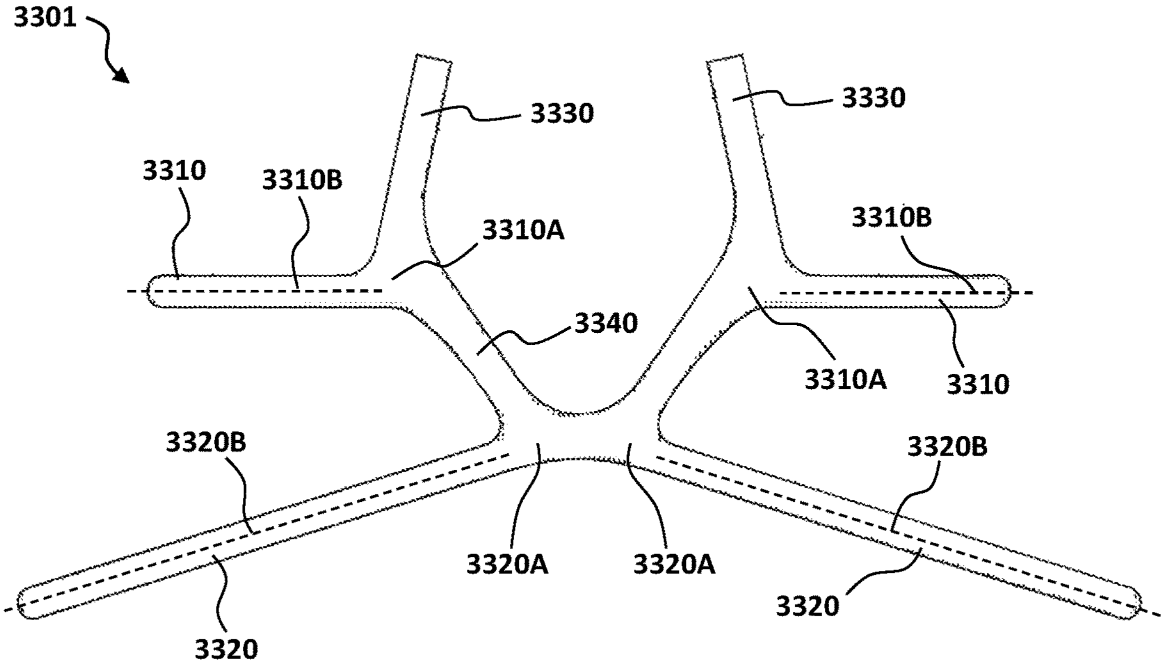

FIG. 23 shows a plan view of a headgear strap 3301 in a flattened state, according to another example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent structure 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap.

In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another suitable for a small sized head, but not a large sized head.

FIG. 7 shows a patient 1000 having donned a patient interface 3000 according to an example of the present technology. Patient interface 3000 comprises a plenum chamber 3200 pressurisable to a therapeutic pressure of at least 6 $cmH_2O$ above ambient air pressure. The plenum chamber including a plenum chamber inlet port sized and structured to receive a flow of air at the therapeutic pressure for breathing by the patient 1000. The patient interface 3000 in this example includes a connection port 3600, connected to an air supply conduit, which supplies air to the plenum chamber 3200.

The patient interface 3000 also comprises a seal-forming structure 3100 constructed and arranged to form a seal with a region of the patient's face surrounding an entrance to the patient's airways. The seal-forming structure 3100 has a hole therein such that the flow of air at said therapeutic pressure is delivered to at least an entrance to the patient's nares. In this example the patient interface 3000 comprises a seal-forming structure 3100 that seal around both the nose and mouth. This type of patient interface is commonly known as a full-face mask. In other examples, the seal-forming structure 3100 may seal about the patient's nares and leave the patient's mouth uncovered. The seal-forming structure 3100 is constructed and arranged to maintain said therapeutic pressure in the plenum chamber 3200 throughout the patient's respiratory cycle in use.

The patient interface 3000 further comprises a vent structure 3400. The vent structure 3400 allows a continuous flow of gases exhaled by the patient from an interior of the plenum chamber 3200 to ambient. The vent structure 3400 is sized and shaped to maintain the therapeutic pressure in the plenum chamber in use.

The patient interface 3000 also comprises a positioning and stabilising structure 3300 to provide a force to hold the seal-forming structure 3100 in a therapeutically effective position on the patient's head. The positioning and stabilising structure comprises a tie, which is constructed and arranged so that at least a portion overlies a region of the patient's head superior to an otobasion superior of the patient's head in use. In one example of the present technology, the positioning and stabilising structure 3300 comprises a frame 3500 to which the plenum chamber 3200 is connected. The frame 3500 is held in place by a number of strap portions of the positioning and stabilising structure 3300.

5.3.3.1 One-Piece Knitted Headgear Strap

In one example of the present technology, shown while donned by a patient in FIG. 7 and in isolation in FIGS. 8 and 9, the positioning and stabilising structure 3300 comprises an integrally formed headgear strap 3301. The headgear strap 3301 has a unitary construction. The headgear strap 3301 is formed as a single, one-piece, knitted strap, as opposed to a combination of multiple strap pieces formed separately and connected together or a one-piece strap cut from a sheet of material. Forming strap portions separately and attaching them together may be slower and/or more costly to manufacture. Cutting a headgear strap may result in significant wasted material. However, in some examples of the present technology, the positioning and stabilising structure 3300 may comprise multiple headgear strap portions that are formed separately and connected together, while including other features of the present technology that are described herein. As used herein, the term strap may be used to describe a structure which comprises a plurality of strap portions, each of which may also take the form and function of a strap in the sense of being a strip of material used for holding an article in place in cooperation with the other strap portions.

The headgear strap 3301 may be knitted as a single piece of material, using flat knitting. By flat knitting the headgear strap 3301, the entire headgear strap 3301 can be knitted in a single flat knitting process. Flat knitting allows for knit-to-shape capability providing a 3D shape without needing secondary processes (e.g., cutting and/or combining multiple components) for some components. In some examples of the present technology, the headgear strap 3301 does not comprise seams or joints. Seams and joints may create uncomfortable pressure on the skin of some users in some circumstances.

One advantage of flat knitting is that the headgear strap 3301 can be knitted into shape directly from fibres in the form of thread, yarn or the like, rather than cut from a sheet. Cutting a plurality of complex shapes from a sheet may leave large offcuts which become waste. Furthermore, when headgear straps are cut from laminated sheets, there may be less flexibility to cost-effectively customise the headgear fabric or colour. New sheets may need to be laminated in order to create new fabric and/or colour options.

Another advantage of the knitted headgear strap 3301 is that the headgear can be knitted to conform very closely to the shape of the patient's head, enhancing comfort and stability. In some examples of the present technology, the headgear strap 3301 may be knitted to conform to the shape of a particular patient's head based on a three-dimensional model of the particular patient's head created with imaging or scanning of the particular patient's head.

Some existing headgear has been produced by double needle crochet knitting. Headgear straps produced by this method may be limited to single, strap-like profiles, rather than complete headgear for a nasal mask or a full-face mask (e.g. patient interfaces having a four-point headgear connection), due to the complex shape of four-point connection headgear straps.

In some examples of the present technology, the headgear strap 3301 is formed using sophisticated knitting techniques to form knitting structures with very good ventilation, elasticity and/or aesthetic appeal. Such knitting structures may be similar to those found in a sports jersey.

In some examples of the present technology the headgear strap 3301 comprises a plurality of different colours and/or patterns. Flat knitting can be used to mix colours and patterns to provide a wide range of design variety without additional cosmetic cost.

In some examples of the present technology, the headgear strap 3301 comprises one or more regions of localised rigidity and/or elasticity. The regions of localised rigidity and/or elasticity may be formed in the headgear strap 3301 by a flat knitting process performed during knitting of the overall headgear strap 3301. Elastic properties can be tailored to meet the different requirements of each region of the headgear strap 3301.

In some examples of the present technology, the headgear strap 3301 is formed by flat knitting but comprises a non-flat shape even before being donned by a patient. The non-flat shape may be produced by knitting the headgear strap 3301 with different knitting densities in different regions. Different properties may be provided to different regions of the headgear strap 3301 to meet predetermined specifications. Providing such properties to the headgear strap 3301 during flat-knitting may result in the headgear strap 3301 comprising a non-flat shape, in some examples. In some forms of the present technology, the non-flat shape may provide the headgear strap 3301 with predetermined properties, such as predetermined elasticities in particular locations and/or directions, or specific force vectors applied by the headgear strap 3301 to the plenum chamber 3200 and/or seal-forming structure 3100 in use.

In some examples of the present technology, the headgear strap 3301 is customised and tailored to a specific patient's anatomy and/or preferences. Flat knitting advantageously provides the manufacturer with flexibility in using a range of yarn, applying different design patterns, applying different colours and surface geometry features. In some examples, the headgear strap 3301 is knitted by a programmable knitting machine. A headgear strap formed by flat knitting can also be highly comfortable. If a high gauge and fine yarn texture is used, the surface finish of the strap may be smooth and present a low risk of causing facial marking.

In some examples, the headgear strap 3301 may comprise one or more text, graphics, branding, logos or the like knitted into the headgear strap 3301 during a single knitting operation performed to form the headgear strap 3301.

In alternative examples, the positioning and stabilising structure 3300 may comprise one or more headgear straps. In some alternative examples, one or more headgear strap portions are formed by a circular knitting process.

In some examples, the headgear strap 3301 can withstand a maximum force of between 10N-100N, more preferably between 15-80N, 20-60N or 25-40N without damage. In some examples, the headgear strap 3301 may comprise one or more portions having a pique knitting structure formed with 100% nylon and may be configured to withstand a maximum load at wale of between 5-8N (in some examples between 6-7N), and a maximum load at course of between 2.5-5.5N (in some examples between 3.5N-4.5N). In some examples, the headgear strap 3301 may comprise one or more portions having a pique knitting structure formed with a combination of nylon and Spandex and may be configured to withstand a maximum load at wale of between 3-6N (in some examples between 4-5N), and a maximum load at course of between 2-4N (in some examples between 2.5-3.5N). In some examples, the headgear strap 3301 may comprise one or more portions having a single jersey knitting structure formed with a combination of nylon and Spandex and may be configured to withstand a maximum load at wale of between 2.5-5N (in some examples between 3-4N), and a maximum load at course of between 1-3N (in some examples between 1.5-2.5N).

In some examples, the headgear strap 3301 is structured to dry in only a short time after being washed or becoming wet from body moisture. The headgear strap 3301 may be highly breathable and may keep the patient's skin relatively dry. The headgear strap 3301 may be configured to cause little or substantially no facial marking. The headgear strap 3301 may be machine washable and hand washable.

The headgear strap 3301 shown in FIG. 8 is configured to create a four-point connection to a frame 3500 or plenum chamber 3200 of a patient interface 3000—more particularly having four strap portions, each of which connects to different points on the frame 3500 or plenum chamber 3200. In other examples of the technology, the headgear strap 3301 may be configured to make a two-point connection to a frame 3500 or plenum chamber 3200, for example when incorporated into a patient interface 3000 of the nasal pillows or nasal cradle type. The headgear strap 3301 may connect at either one or two points to a frame 3500 or plenum chamber 3200 of a patient interface 3000 having a full-face configuration (e.g. a configuration in which the seal-forming structure 3100 seals about an inferior periphery of the patient's nose and leaves most or all of the bridge of the patient's nose uncovered). In some examples the headgear strap 3301 may be configured as a backstrap for a positioning and stabilising structure 3300 for a conduit headgear system. In such an example, the headgear strap 3301 may, in use, overlay or lie inferior to the patient's occipital bone and connect between a pair of headgear conduit tubes that lie against the lateral sides of the patient's head.

5.3.3.2 Headgear Strap Portions

As shown in FIGS. 7-9, the positioning and stabilising structure 3300 may comprise multiple strap portions. A plurality of strap portions may be provided in a single headgear strap 3301, such as in the positioning and stabilising structure 3300 of FIGS. 7-9. The positioning and stabilising structure 3300 in this example of the present technology comprises a ring strap portion 3340. When donned, the ring strap portion 3340 encircles a posterior side of the patient's head, providing a strong anchor for other strap portions that connect to the plenum chamber 3200. The ring strap portion 3340 may also be known as a crown portion, a crown strap, a rear/posterior portion or a halo.

In this example of the present technology, the ring strap portion 3340 of the positioning and stabilising structure 3300 comprises a superior portion 3302 and an inferior portion 3304. The superior portion 3302 lies in use against the patient's head over the parietal bones of the patient's head. The inferior portion 3304 is configured to lie against the patient's head over or inferior to the occipital bone of the patient's head in use. As illustrated, the ring strap portion 3340 defines a loop.

The positioning and stabilising structure 3300 comprises a pair of upper strap portions 3310. Each of the upper strap portions 3310 is configured to connect between the ring strap portion 3340 and the plenum chamber 3200. In use, each of the upper strap portions 3310 is located alongside the patient's head, on a respective side, superior to an otobasion superior of the patient's head.

In the example shown in FIGS. 7-9, the positioning and stabilising structure 3300 also comprises a pair of lower strap portions 3320. Each of the lower strap portions 3320 is configured to connect between the ring strap portion 3340 and plenum chamber 3200. In use, each of the lower strap portions 3320 is located alongside the patient's head, on a respective side, inferior to an otobasion superior of the patient's head.

Each of the upper strap portions 3310 and the lower strap portions 3320 may connect to the plenum chamber 3200 either directly or via a frame 3500 of the positioning and stabilising structure 3300. In the example illustrated in FIG. 7, upper strap portions 3310 and lower strap portions 3320 connect to the plenum chamber 3200 via a frame 3350 to which the plenum chamber 3200 is connected.

One or more of the headgear strap portions of the positioning and stabilising structure 3330 (e.g. the upper strap portions 3310, lower strap portions 3320 and the overhead strap portions 3330 described below) may comprise a fastening portion 3360. The fastening portion 3360 may be structured and/or arranged to allow the strap to be looped back and fastened onto itself. In one example, the fastening portion 3360 may comprise hook-and-loop material. In another example, the fastening portion 3360 may comprise magnets configured to be attracted to each other when the strap is looped back onto itself.

In some examples of the technology the positioning and stabilising structure 3300 may comprise upper strap portions 3310 but may not comprise lower strap portions 3320. In some examples of the present technology, a patient interface 3000 may comprise a positioning and stabilising structure 3300 comprising upper strap portions 3310 connecting a rear portion of the positioning and stabilising structure 3300, such as a ring strap portion 3340, to a plenum chamber 3200 comprising nasal pillows or a cradle cushion seal-forming structure 3100.

In this example, the ring strap portion 3340 comprises a rigidised portion 3345. The rigidised portion 3345 comprises a higher rigidity in comparison to other portions of the ring strap portion 3340. The rigidised portion 3345 may not be completely rigid but may instead be "rigidised" in the sense that it is more rigid than some or all of the other parts of the ring strap portion 3340. The rigidised portion 3345 and other portions of the ring strap portion 3340 may all be flexible to an extent, but the rigidised portion 3345 may be stiffer. The rigidised portion 3345 may be less stretchable and/or less bendable than other portions of the ring strap portion 3340. The rigidised portion 3345 is, in this example, provided along a length of the loop defined by the ring strap portion 3345. The rigidised portion 3345 of the ring strap portion 3340 may reinforce the ring strap portion 3340. Reinforcing the ring strap portion 3340 may improve the stability of the patient interface 3000 in use, since a purpose of the ring strap portion 3340 is to provide an anchor for the other strap portions which connect to the plenum chamber 3200 while under tension to pull the plenum chamber 3200 into the patient's face. The rigidised portion 3345 may be substantially non-stretchable, although may still be bendable to conform to the curvature of the patient's head. The non-stretchable nature of the rigidised portion 3345 provides reinforcement to the ring strap portion 3340, providing a firmer anchor and resulting in a more stable positioning and stabilising structure 3300. The upper strap portions 3310 may be stretchable. In some examples of the present technology, the rigidised portion 3345 may be stretchable, but less so than other portions of the ring strap portion 3340. In some examples, the ring strap portion 3340 may comprise a first portion provided along a length of the loop defined by the ring strap portion 3345 and a second portion provided along the length of the loop. The second portion may comprise the rigidised portion 3345. The second portion may comprise a greater stiffness than the first portion. The second portion may be less bendable than the first portion. The second portion may be less stretchable than the first portion.

In this example of the technology, the rigidised portion 3345 is provided along substantially the entire length of the loop defined by the ring strap portion 3340. As illustrated, the ring strap portion 3340 comprises an inside periphery 3341 and an outside periphery 3342. In some examples, the ring strap portion 3340 is stiffer at or proximate the inside periphery 3341 than at or proximate the outside periphery 3342. In one example, the rigidised portion 3345 is provided to the ring strap portion 3340 proximate the inside periphery 3341 of the ring strap portion 3340. The rigidised portion 3345 may define the inside periphery 3341 of the ring strap portion 3340 or, alternatively, may be located close to an edge of the ring strap portion 3340 defining the inside periphery 3341. The rigidised portion 3345 may form substantially the entire inside periphery 3341 of the ring strap portion 3340. In other examples, the rigidised portion 3345 may be provided substantially centrally between the inside periphery 3341 of the ring strap portion 3340 and the outside periphery 3342 of the ring strap portion 3340.

Reinforcing the inside periphery 3341 around the ring strap portion 3340 may be advantageous because the outside periphery 3342 (the more anterior side) of the ring strap portion 3340 may then be able to be formed contiguously with any other strap portions connecting the ring strap portion 3340 with the plenum chamber 3200 of the patient interface 3000. Positioning the rigidised portion 3345 centrally between the inside periphery 3341 and the outside periphery 3342 may have an advantage in even distribution of pressure loading on the patient's skin. The inside periphery 3341 of the ring strap portion 3340 may also not need to deform as much as the outside periphery 3342 since it is the outside periphery 3342 from which further strap portions extend to connect to the plenum chamber 3200 in front of the patient's face.

The ring strap portion 3340 and/or any other strap portions of the positioning and stabilising structure 3300 may comprise rounded edges. A rounded edge may be less likely to cause skin marking and may be more comfortable on the patient's skin.

In some examples of the present technology, the strap portions of the positioning and stabilising structure 3300 may be formed by knitting. That is, one or more of the upper strap portions 3310, lower strap portions 3320 and the ring strap portion 3340 may comprise a knitted fabric structure. In some examples, one or more of these strap portions of the positioning and stabilising structure 3300 may be formed by flat knitting. For example, the ring strap portion 3340, upper strap portions 3310 and/or lower strap portions 3320 may comprise a single jersey knitted structure and may be formed from a combination of nylon and spandex. A single jersey knitted structure advantageously provides the necessary flexibility and elasticity for the strap portions without excessive thickness. Alternatively, the ring strap portion 3340 may comprise a double jersey loop formation. The rigidised portion 3345 of the ring strap portion 3340 may comprise a pique knitting structure and may be formed from nylon or a combination of nylon and spandex. It may be advantageous to use a pique knitting structure to form the rigidised portion 3345 since this type of structure is well-suited to create a ridge having a sufficiently high level of rigidity while also having a rounded edge.

The headgear straps of the positioning and stabilising structure 3300 may be stretchable. Advantageously, the upper strap portions 3310, lower strap portions 3320 and ring strap portion 3340 are stretchable. The stretchable nature of the ring strap portion 3340 of the positioning and stabilising structure 3300 enables the ring strap portion 3340 to conform and fit snugly to the posterior, lateral and superior surfaces of the patient's head in use. Stretchiness in the upper strap portions 3310 and lower strap portions 3320 enables these strap portions to extend in length slightly to provide some relief when the plenum chamber 3200 is pressurised. In some examples, the upper strap portions 3310 may need less elasticity than the lower strap portions 3320 because lower head circumference will keep on changing in the dynamic movement (bending head up and down). The portions of the headgear near the neck area (e.g., a portion lower strap portions 3320) can be provided with lower stretch but not necessary rigid, because the function is mainly to work as a pivot point. Rigidity may be needed near the cheek bone area (e.g., in a portion of the upper strap portions 3310) to ensure the headgear does not interfere with the eyes.

When the plenum chamber 3200 is under pressure in use, the volume of pressurised air inside the plenum chamber 3200 pushes the plenum chamber 3200 and frame 3500 in an anterior direction away from the patient's face. The force from this pressure must be countered by tension in the headgear straps in order to keep the plenum chamber 3200 and seal-forming structure 3100 in sealed contact with the patient's face. The ability of the upper strap portions 3310 and lower strap portion 3320 to extend in length by at least a small amount can make wearing the patient interface 3000 more comfortable when this occurs.

Advantageously, the upper strap portions 3310, lower strap portions 3320 and ring strap portion 3340 are all breathable due to the knitted structure with which they are formed. Breathability is advantageous as it can keep the headgear straps and the patient's skin dry while keeping the temperature of the patient's skin underneath the headgear straps manageable.

The rigidised portion 3345 may be a round, thickened portion of headgear strap material. The rigidised portion 3345 may comprise an increased material thickness relative to adjacent portions of the ring strap portion 3340. In some examples of the present technology a patient-contacting side of the ring strap portion 3340 is substantially flat and the increased material thickness is provided to a non-patient-contacting side of the ring strap portions 3340. Advantageously, achieving extra thickness by providing the extra material forming the rigidised portion 3345 on the non-patient-contacting side of the ring strap portion 3340 keeps the patient-contacting side of the ring strap portion 3340 substantially flat. A flat surface may advantageously be more comfortable against a patient's skin than a non-flat surface. Since, in the example shown in FIG. 7, the rigidised portion 3345 is provided to the inside periphery 3341 of the ring strap portion 3340, the inside periphery 3341 is thicker than the outside periphery 3342. In use, a posterior edge of the ring strap portion 3340 is thicker than anterior edges of the ring strap portion 3340. A thicker inside periphery 3341 in comparison to the outside periphery 3342 results in a stiffer inside edge of the ring strap portion 3340, providing reinforcement to the ring strap portion 3340.

The reinforcement of the reinforced portion 3345 may not be discernible on the patient-contacting side of the ring strap portion 3340. In use, the patient may not be able to see and/or feel any features of the reinforced portion 3345. In FIG. 10, the cross section at two locations of the ring strap portion 3340 is illustrated. As illustrated, extra thickness at the rigidised portion 3345 is provided to only one side of the ring strap portion 3340 (the non-patient-contacting side). The other side of the ring strap portion 3340 is substantially flat. Additionally, the rigidised portion 3345 is rounded, as is the inside edge of the ring strap portion 3340 (at the inside periphery 3341) and the outside edge of the ring strap portion 3340 (at the outside periphery 3342). Smooth/rounded edges may apply only a light pressure on the user's face, which may be particularly useful for maintaining comfort even if the patient overtightens the headgear straps.

In some examples of the present technology, the ring strap portion 3340 comprises a thickness in the rigidised portion 3345 within the range of 3-5 mm, such as within the range of 3.5-4.5 mm. The rigidised portion 3345 may comprise a thickness of 4 mm in some examples. The ring strap portion 3340 may comprise a thickness within the range of 1.5-3.5 mm, such as within the range of 2-3 mm, for example 2 mm, at regions of the ring strap portion 3340 other than the rigidised portion 3345. The upper strap portions 3310 and lower strap portions 3320 may also comprise a thickness within the range of 1.5-3.5 mm, such as within the range of 2-3 mm, for example 2 mm.

The rigidity of the rigidised portion 3345 may, in some examples, not be uniform along the length of the ring strap portion 3340. The rigidised portion 3345 may be less stretchable and/or flexible in some locations in comparison to other locations around the ring strap portion 3340. In some examples, the rigidised portion 3345 may be larger in particular locations (in comparison to other locations) such that it has an increased rigidity and/or stiffness at those particular locations. As illustrated in FIGS. 7-8, the rigidised portion 3345 is larger proximate the junctions of the upper strap portions 3310 and the ring strap portion 3340. In this example the rigidised portion 3345 is wider proximate the upper strap portions 3310 than at other locations along the ring strap portion 3340. In other examples of the present technology, the rigidised portion 3345 may be more rigid at particular locations due to an increased material thickness and/or the use of a different knitting structure (in examples in which the ring strap portion 3340 is formed by knitting).

The width and/or material thickness may vary along the length of the ring strap portion 3340 to provide stiffness in locations where stiffness/stability is required and to provide for flexibility and/or comfort where stiffness is less required. Extra stiffness may be particularly advantageous proximate the junction of the upper strap portions 3310 and the ring strap portion 3340 since, in use, the upper strap portions 3310 are under tension and there is a relatively large area of the strap material at the junction. Strengthening this junction may help provide a high level of stability to the patient interface 3000.

The superior portion 3302 of the ring strap portion 3340 may comprise one or more overhead strap portions 3330. As shown in FIGS. 8, 9 and 13, in one example the ring strap portion 3340 comprises a pair of overhead strap portions 3330. The overhead strap portions 3330 may be configured to adjust and connect to each other. In one example, the overhead strap portions 3330 are configured to adjustably connect to each other proximate the sagittal plane of the patient's head. An adjustable connection between the two overhead strap portions 3330 may advantageously enable the positioning and stabilising structure 3300 to fit to a range of patient head shapes and sizes. In other examples of the present technology, the positioning and stabilising structure 3330 may comprise a single overhead strap portion 3330. If only a single overhead strap portion 3330 is provided, it may be elastically extendable in length to fit a range of patient head sizes.

The two overhead strap portions 3330 may be adjustably connected together with a buckle 3335. The buckle 3335 may comprise a pair of slots, eyelet or other openings through which the overhead strap portions 3330 can pass, enabling each overhead strap portion 3330 to be passed through a portion of the buckle 3335 and secured back onto itself. The overhead strap portions 3330 may each comprise hook-and-loop fastening material enabling the end portion of each overhead strap portion 3330 to be fastened to an intermediate portion of the respective overhead strap portion 3330. In other examples of the present technology, each overhead strap portions 3330 may be fastened back onto itself with a clip, elastic band, magnet or other suitable fastening means. In alternative examples, two overhead strap portions are formed separately during manufacturing of the positioning and stabilising structure 3300 and then welded or sewn together to complete the loop formed by the ring strap portion 3340.

FIG. 16 shows a headgear strap 3301 of a positioning and stabilising structure 3300 according to another example of the present technology. This headgear strap 3301 may be integrally formed by knitting and may be formed in a single flat knitting process. The headgear strap 3301 of FIG. 16 may include any of the features and/or properties of the headgear straps 3301 described with reference to FIGS. 7-15.

The headgear strap 3301 shown in FIG. 16 comprises a pair of upper headgear strap portions 3310, each configured to connect to a plenum chamber 3200 of a patient interface 3000 in use. In this example, each of the upper headgear strap portions 3310 is configured to connect to a respective headgear conduit of the positioning and stabilising structure 3330 located on a respective lateral side of the patient's head in use. The headgear conduits may be each be configured to extend from a medial location on a superior portion of the patient's head laterally across the superior portion of the patient's head, inferiorly at the lateral sides of the patient's head and then anteriorly and medially to connect to the plenum chamber 3200 proximate an entrance to the patient's airways. Accordingly, the upper headgear strap portions 3310 are configured to connect to the plenum chamber 3200 via headgear conduits. The headgear strap 3301 also comprises a pair of lower headgear strap portions 3320, each configured to connect to the plenum chamber 3200. The lower headgear strap portions 3320 may connect directly to the plenum chamber 3200 or a frame 3500 of the positioning and stabilising structure.

FIG. 17 shows a patient interface 3000 comprising a positioning and stabilising structure 3300 having a headgear strap 3301, according to another example of the present technology, configured for use in a patient interface 3000 comprising conduit headgear. The headgear strap 3301 shown in FIG. 17 connects to headgear conduits 3900 in the same manner as the headgear strap shown in FIG. 16. As illustrated, the headgear conduits are joined at a junction 3903 at a superior portion of the patient's head. A connection port 3600 supplies a pressurised flow of breathable gas to the headgear conduits 3900. Each headgear conduit 3900 comprises a lateral portion 3901 alongside the patient's head which connects to a plenum chamber 3200 located at an entrance to the patient's airways in use via a connector 3800. More generally, each headgear conduit 3900 may receive the flow of air from a connection port 3600 on top of the patient's head and deliver the flow of air to the entrance of the patient's airways via the seal-forming structure 3100, each headgear conduit 3900 constructed and arranged to contact, in use, at least a region of the patient's head superior to an otobasion superior of the patient's head on a respective side of the patient's head.

As shown in FIG. 17, the positioning and stabilising structure 3300 comprises a pair of upper strap portions 3320 which connect between a neck strap portion 3334 and respective headgear conduits 3900. In this example the upper strap portions connect to eyelets on tabs 3902 of the headgear conduits 3900. The lower strap portions 3320 connect between the neck strap portion 3334 and the plenum chamber 3200, in this example via headgear clips 3322.

In the examples shown in FIGS. 16 and 17, the headgear strap 3301 does not comprise a ring strap portion or overhead strap portions since, in the positioning and stabilising structure 3300 for which the headgear strap 3301 is configured, the headgear conduits provide the functions of the ring strap portion and overhead strap portions of the examples shown in FIGS. 7-15. However, some examples of the present technology include a positioning and stabilising structure 3300 comprising headgear conduits as well as a headgear strap 3301 comprising a ring strap portion 3340 and/or overhead strap portions 3330.

The headgear strap 3301 shown in FIGS. 16 and 17 comprises a neck strap portion 3334. The neck strap portion 3334 connects each of the upper headgear straps 3310 and lower headgear straps 3320. The neck strap portion 3334 is configured to lie against a posterior surface of the patient's neck in use and/or a surface of the patient's head overlying an occipital bone of the patient's skull. The neck strap portion 3334 may be configured to overlay the occipital bone of the patient's head and/or lie against the patient's neck in use.

The neck strap portion 3334, upper headgear strap portions 3310 and lower headgear strap portions 3320 may be integrally formed. The headgear strap 3301 and its upper headgear strap portions 3310, lower headgear strap portions 3320 and neck strap portion 3334 may be formed by a single flat knitting process.

The headgear strap 3301 shown in FIG. 16 comprises a rigidised portion 3345. In this example the rigidised portion 3345 is provided to the neck strap portion 3334. The rigidised portion 3345 may be formed in any of the same ways as described above in relation to the rigidised portion 3345 of the positioning and stabilising structures 3300 shown in FIGS. 7-15, such as with an increased thickness and/or more rigid knitting structure. The rigidised portion 3345 in this example may be substantially non-stretchable.

The rigidised portion 3345 may reinforce the neck strap portion 3334. This reinforcement may provide a high level of stability to the patient interface 3000 in use, since a purpose of the neck strap portion 3334 is to provide an anchor for the other strap portions which connect to the plenum chamber 3200 while under tension to pull the plenum chamber 3200 towards the patient's face. The rigidised portion 3345 may be substantially non-stretchable or at least less stretchable than the other strap portions, although may still be bendable to conform to the curvature of the patient's head. The non-stretchable or low-stretch nature of the rigidised portion 3345 provides reinforcement to the neck strap portion 3334, providing a firmer anchor and resulting in a more stable positioning and stabilising structure 3300. The upper strap portions 3310 and lower strap portions 3320 may be stretchable.

The neck strap portion 3334 may comprise stretchable portions in addition to the rigidised portion 3345. In the example shown in FIG. 16, the neck strap portion 3334 comprises stretchable portions superior and inferior to the rigidised portion 3345. The neck strap portion 3334 in this example comprises a superior stretchable portion 3346 and an inferior stretchable portion 3347. The stretchable portions may be provided to superior and/or inferior edges of the neck strap portion 3334. In this example the superior stretchable portion 3346 is provided along a superior edge of the neck strap portion 3334 and the inferior stretchable portion 3347 is provided along an inferior edge of the neck strap portion 3334. Providing stretchable portions at the superior and inferior edges of the neck strap portion 3334 may be advantageous for patient comfort. The superior and inferior edges of the neck strap portion 3334, if made to be substantially rigid, could in this configuration concentrate force from headgear tension on the patient's skin. Providing stretchable portions at the superior and inferior edges may provide some relief, improving patient comfort. The stretchable portions may also enable the neck strap portion 3334 to conform to the curvature of the patient's neck.

5.3.3.3 Headgear Ventilation

In some forms of the present technology, the positioning and stabilising structure comprises headgear straps having one or more ventilation portions structured and/or arranged to provide increased breathability through the headgear straps. As shown in FIGS. 7-10, the positioning and stabilising structure 3300 comprises three ventilation portions 3350. In this example, each of the ventilation portions 3350 are provided in the ring strap portion 3340 and each provide a region of increased breathability through the ring strap portion 3340. The ring strap portion 3340 comprises a ventilation portion 3350 proximate each of the upper strap portions 3310 (e.g. at each junction between an upper strap portion 3310 and the ring strap portion 3340). Additionally, the ring strap portion 3340 comprises a single ventilation portion 3350 proximate the junction between each of the lower strap portions 3320 and the ring strap portion 3340.

In this example, the lower strap portions 3320 both extend from the ring strap portion 3340 at a similar location. In examples of the technology in which lower strap portions 3320 extend from more distinct locations around the ring strap portion 3340, two separate ventilation portions 3350 may be provided, one at each of the junctions between a lower strap portion 3320 and the ring strap portion 3340. The ventilation portions 3350 may be provided at locations where the headgear straps comprise a relatively large area/footprint on the patient's head. These regions may be most susceptible to increases in skin temperature and/or moisture buildup. The junctions between the ring strap portion 3340 and the upper strap portions 3310 and lower strap portions 3320 may cover a relatively large surface area on the patient's skin meaning extra breathability may be desirable at these locations to provide a high level of patient comfort. The ventilation portions 3350 may advantageously prevent buildup of moisture in the headgear material and/or on the patient's skin. The ventilation portions 3350 are areas of localised breathability. The knitted structure of the other headgear strap portions of the positioning and stabilising structure 3300 may also be highly breathable, but the ventilation portions 3350 may be particularly breathable due to the meshed knitting structure used to form the ventilation portion 3350. The ventilation portions 3350 also advantageously keep the patient's skin cool, at least under the ventilation portions 3350, by facilitating fresh air exchange through the material forming the headgear strap 3301.

The ventilation portions 3350 may comprise a knitted fabric structure. The knitted fabric structure may be formed during the same knitting process that is performed to form the ring strap portion 3340, rigidised portion 3345, upper strap portions 3310 and/or lower strap portions 3320. In one example, the ventilation portions 3350 comprise a pique mesh knitting structure. The ventilation portions 3350 may be stretchable. However, in some examples the ventilation portions 3350 may be less stretchable than other headgear strap portions. A relatively low elasticity in the ventilation portions 3350 may prevent the mesh structure from being stretched to such an extent that the openings forming the mesh structure are occluded by the fabric, which could reduce breathability. The ventilation portions 3350 may be formed from nylon or from a combination of nylon and spandex, as examples.

In some examples, as shown in FIGS. 7, 8 and 10, the rigidised portion 3345 of the ring strap portion 3340 surrounds the ventilation portions 3350. Advantageously, this may provide for additional stiffness at regions of the headgear strap portions that have a large surface area and may otherwise be overly flexible. Not every ventilation portion 3350 may be surrounded by rigidised portion 3345. In the example shown in FIGS. 7, 8 and 10, the ventilation portion 3350 proximate the patient's neck is not surrounded by a rigidised portion 3345. However, the ventilation portions 3350 proximate the upper strap portions 3310 surrounded by the rigidised portion 3345.

The ring strap portion 3340 comprises a pair of superior ventilation portions 3350, each being provided proximate a respective upper strap portion 3310. As described above, the rigidised portion 3345 surrounds each of the superior ventilation portions 3350. In this example, the rigidised portion 3345 comprises a higher material thickness on a posterior side of each of the superior ventilation portions 3350 than on an anterior side of each of the superior ventilation portions 3350. As described above, the rigidised portion 3345 may be formed to be stiffer proximate the inside periphery 3341 of the ring strap portion 3340.

The ring strap portion 3340 also comprises an inferior ventilation portion 3350 provided between the pair of lower strap portions 3320. As shown in FIGS. 8 and 9, the inferior ventilation portion 3350 comprises an inferior edge 3351 spaced from an inferior edge 3343 of the ring strap portion 3340. The inferior edge 3351 of the inferior ventilation portion 3350 and the inferior edge 3343 of the ring strap portion 3340 are both arcuate in this example of the technology.

The inferior edge 3351 of the ventilation portion 3350 comprises a greater curvature than the inferior edge 3343 of the ring strap portion 3340. This greater curvature of the inferior edge 3351 of the ventilation portion 3350 provides a maximum spacing between the inferior edge 3351 of the ventilation portion 3350 and the inferior edge 3343 of the ring strap portion 3340 at or proximate the sagittal plane of the patient's head in use. The ventilation portion 3350 and/or the ring strap portion 3340 in the vicinity of the ventilation portion 3350 may be in contact with or in close proximity to a patient's neck. Additionally, the mesh construction of the ventilation portion 3350 may be rougher than the non-meshed surface of the ring strap portion 3340. Accordingly, providing a spacing between the inferior edge 3351 of the ventilation portion 3350 and the inferior edge 3343 may reduce the amount of the meshed fabric in contact with the patient's skin. This may be particularly advantageous when the contact between the ring strap portion 3340 and the patient's skin occurs while the ring strap portion 3340 is under tension and for a prolonged period of time, as occurs during use of the patient interface 3000.

The headgear strap 3301 of the positioning and stabilising structure 3300 shown in FIG. 16 also comprises a ventilation portion 3350. The ventilation portion 3350 in this example is provided in the neck strap portion 3334. The ventilation portion 3350 may take the same form and comprise the same properties as described above in relation to the ventilation portions 3350 of the positioning and stabilising structures 3300 and headgear straps 3301 shown in FIGS. 7-15. In this example, the rigidised portion 3345 surrounds the ventilation portion 3350.

5.3.3.4 Fastening Portions

As discussed above, some or all of the headgear strap portions of the positioning and stabilising structure 3300 may comprise fastening portions 3360. As shown in FIGS. 7, 8 and 16, the upper strap portions 3310 and lower strap portions 3320 each comprise a fastening portion 3360 proximate the end of the respective strap portion. The fastening portions 3360 are each structured and/or arranged to allow the respective strap portion to be looped back and fastened onto itself.

In examples, the fastening portions 3360 may comprise hook-and-loop material and/or magnets. This allows each of the upper strap portions 3310 and lower strap portions 3320 to be connected to other components of the patient interface 3000, such as the frame 3500 or, in other examples, directly to the plenum chamber 3200. The upper strap portions 3310 and lower strap portions 3320 may connect directly to the frame 3500 through slots or other openings or may connect to headgear clips which then connect to the frame 3500. In one example, as shown in FIG. 7, the upper strap portions 3310 each connect to an upper strap connection point 3510 on the frame 3500. Each upper strap connection point 3510 comprises a slot through which the fastening portion 3360 of an upper strap portion 3310 can pass, enabling an end of the upper strap portion 3310 to be secured back onto an intermediate/middle portion of the upper strap portion 3310. In this example, the lower strap portions 3320 connect to headgear clips 3322. Each lower strap portion 3320 passes through a slot formed in a headgear clip 3322 and is then looped back and secured to itself. The headgear clip 3322 is then connected to the frame 3500. In this example, the headgear clips 3322 and frame 3500 each comprise magnets enabling the headgear clips 3322 to be quickly and release of the secured to predetermined parts of the frame 3500 under magnetic attraction. In the example shown in FIG. 16, the fastening portions 3360 of the upper headgear strap portions 3310 may loop through eyelets on headgear conduits of a positioning and stabilising structure 3300. The fastening portions 3360 of the lower headgear straps 3320 may loop thought slots on a plenum chamber 3200 of the patient interface 3000 or loop through headgear clips which connect to the plenum chamber 3200, in a similar manner to that shown in FIG. 7.

One or more of the strap portions of the positioning and stabilising structure 3300 may comprise at least one blind guide 3370. In examples of the present technology in which the headgear strap portions comprise a knitted fabric, the blind guides 3370 may also be formed by the knitted fabric. In some examples, a headgear strap is formed by flat knitting and a blind guide is also formed by flat knitting during the same process. The blind guide 3370 may provide a tactile indication of the location of a fastening portion 3360 on a strap. The blind guides 3370 may be features that the patient can feel on the surface of the headgear straps, configured to aid the user in manipulating the headgear straps (e.g. fitting and adjusting the straps), especially when the mask has been donned by the patient and the patient cannot see the headgear straps. The blind guides 3370 may be raised bumps, a raised profile or other tactile features to guide the user in securing the straps back onto themselves after looping the strap through slots or eyelets provided to the mask frame or headgear clips. In other examples of the present technology the blind guides 3370 may comprise recessed portions.

As shown in FIGS. 7, 8 and 16, each of the upper strap portions 3310 and the lower strap portions 3320 comprises a blind guide 3370 in the fastening portion 3360 of the respective strap. Each blind guide 3370 provides a tactile indication of the location of a fastening portion 3360 on a respective one of the upper strap portions 3310 and the lower strap portions 3320. In some examples, blind guides 3370 may be provided to overhead strap portions of the positioning and stabilising structure 3300 as well.

FIG. 11 shows an exploded view of a fastening portion 3360 of a strap of a positioning and stabilising structure 3300. In the illustrated example, the strap is an upper strap portion 3310 of the positioning and stabilising structure 3300 but the features of the fastening portion 3360 and blind guide 3370 may be applied to the lower strap portions 3320 or other straps/strap portions of the positioning and stabilising structures 3300 according to examples of the present technology. The upper strap portion 3310 comprises a non-patient-contacting surface on which the blind guide 3370 is provided. The blind guide 3370 may comprise a raised portion with respect to the non-patient-contacting surface of the upper strap portion 3310. The raised portion may surround at least part of the fastening portion 3360. As illustrated in FIGS. 10 and 11, the raised portion comprises an elongate raised profile on the non-patient-contacting surface of the strap. In this example, the elongate raised profile of the blind guide 3370 is provided at one or more edges of the fastening portion 3360. The elongate raised profile may be provided at edges of the fastening portion 3360 which in use are superior, posterior and inferior edges. The blind guide 3370 may be provided around a periphery of a fastening portion 3360, for example on one, two or more sides thereof.

In other examples of the present technology, a strap of a positioning and stabilising structure 3300 may comprise a recessed profile being recessed with respect to the non-patient-contacting surface. The recessed portion may surround at least part of a fastening portion 3360 on the strap. Any suitable features of shape and location of a raised blind guide described herein may be applied to a recessed blind guide according other examples of the present technology. Likewise, any of the illustrated examples of positioning and stabilising structures according to the present technology may comprise recessed blind guides instead of raised blind guides, in other examples of the technology. For example, a recessed blind guide may be formed by an elongate recessed profile and may surround three more sides of a fastening portion 3360. The recessed profile may be formed by a reduced thickness of the strap. The present technology includes blind guides formed by other features as well, such regions of higher rigidity, portions of a headgear strap having surface finishes/textures that are different from adjacent regions of the strap. The knitting pattern, knitting density and/or yarn material/thickness could be varied in order to provide a user with tactile indication of the location of the fastening portion on the strap.

In some examples of the present technology, the elongate raised profile of the blind guide 3370 is rounded. This may make the blind guide 3370 more comfortable for the patient to touch, more aesthetically pleasing and may make the positioning and stabilising structure 3300 more durable due to a smoother transition between the raised portion and the non-patient-contacting surface on which it is provided.

The raised portion of the blind guide 3370 may be formed by increased thickness of the strap in comparison to adjacent regions of the strap. The extra material forming the increased thickness may be provided to the non-patient-contacting surface.

The fastening portions 3360 of the straps may comprise a hook-and-loop fastening material (e.g. Velcro™). The fastening portion 3360 may comprise an end portion 3361 comprising one of a hook material and a loop material provided to the non-patient-contacting surface and an intermediate portion 3363 comprising the other of the hook material and the loop material provided to the non-patient-contacting surface. The intermediate portion 3363 may be provided adjacent the end portion 3361 of the strap. In the example shown in FIG. 11, the fastening portion 3360 comprises a hook portion 3362 and a loop portion 3364. The hook portion 3362 is provided to the end portion 3361 of the upper strap portion 3310. The loop portion 3364 is provided to the intermediate portion 3363 of the upper strap portion 3310. In other examples, the hook portion 3362 may be provided to the intermediate portion 3363 of the strap, and the loop portion 3364 may be provided to the end portion 3361 of the strap. The hook portion 3362 is able to be releasably attached to the loop portion 3364. This means that, once the upper strap portion 3310 is threaded through an opening in another component (e.g. a slot formed in the frame 3500), the end portion 3361 can be looped back towards the intermediate portion 3363 and the hook portion 3362 can be releasably attached to the loop portion 3364. The blind guide 3370 may surround only one of the end portion 3361 and intermediate portion 3363. In the example shown in FIG. 11, the blind guide 3370 is provided around only the intermediate portion and 3363 and loop portion 3364. As illustrated, the blind guide 3370 is provided around three sides of the loop portion 3364.

The intermediate portion 3363 may be longer than the end portion 3361. This may enable the end portion 3361 to be fastened to a range of locations along the intermediate portion 3363, increasing the amount of length adjustability of the strap. In some examples, the intermediate portion 3363 is several times longer than the end portion 3361.

The strap portion comprising the blind guide 3370 (e.g. the upper strap portions 3310, the lower strap portion 3320 or any other strap portion in other examples of the technology) and the blind guide 3370 itself may be formed together during a single knitting process. The blind guide 3370 may comprise a pique knitting structure. The strap may comprise a single jersey knitting structure. In alternative examples of the technology, the strap may comprise a double jersey loop formation. A strap and a blind guide 3370 may be integrally formed.

The hook portions 3362 and the loop portions 3364 may be formed separately and then assembled with the respective strap portions. They may be adhered to or sewn into the strap portions of the positioning and stabilising structure 3300. Alternatively, one or both of the hook portion 3362 and loop portion 3364 may be ultrasonically welded to the headgear strap. In other examples of the technology, one or both of the hook portion 3362 and loop portion 3364 are knitted. The hook portion 3362 and/or the loop portion 3364 may be formed during the same knitting process used to form the strap portion to which they are provided. The knitting process may comprise flat knitting. The hook portions 3362 and loop portions 3364 may be formed from nylon. This may reduce skin irritation through superior breathability, and may provide a soft loop that avoids abrasiveness against the patient's skin. The hook portion 3362 and loop portion 3364 may be die cut.

The upper strap portion 3310 and/or other strap portions may comprise a visual guide 3366 indicating the end portion of the strap. The visual guide 3366 may surround the hook portion 3362. The visual guide 3366 may not be raised above the surface of the strap portion and may be a visual guide in the form of coloured fabric. The visual guide 3366 may also, or alternatively, facilitate assembly of the hook portions 3362 to the strap portions to which they are to be fixed during manufacturing.

As illustrated in FIGS. 8 and 16, each of the upper strap portions 3310 and lower strap portion 3320 comprises a fastening portion 3360. Each of the fastening portions 3360 comprises a hook portion 3362 provided to an end portion 3361 of the respective strap portion and a loop portion 3364 provided to an intermediate portion 3363 of the respective strap portion. In other examples of the technology, only the upper strap portions 3310, only the lower strap portions 3320, or neither of the strap portions, have this configuration. In some examples, the knitting process used to form the headgear strap portions is configured to precisely provide a predetermined level of stiffness to the strap portions such that adjustability and the blind guides are not required. In some examples, this predetermined level of stiffness may be determined based on the specific shape and size of the patient's head as determined by a scan.

In some examples, the positioning and stabilising structure 3300 may not have lower strap portions 3320 and may only have upper strap portions 3310. Such an arrangement may be suited for a patient interface 3000 of an "under the nose" type (e.g. having a seal-forming structure 3100 in the form of nasal pillows or nasal cradle). In such an example, the upper strap portions 3310 may have the fastening portions 3360 and blind guides 3370 described above. A positioning and stabilising structure 3300 that has upper strap portions 3310 but not lower strap portions 3320 may have a ring strap portion 3340 having a superior portion 3302 and an inferior portion 3304. One or both of the superior portion 3302 and the inferior portion 3304 may be adjustable by the patient. In such an example, the superior portion 3302 and/or the inferior portion 3304 may be split into two strap portions connected by a buckle (or a similar component having to opening through which straps can be fed). Each of the two strap portions forming the superior portion 3302 and/or inferior portion 3304 may comprise features of the fastening portion 3360 and/or blind guides 3370 as described above with reference to FIG. 11.

The blind guides 3370 may be stretchable in some examples of the technology and non-stretchable in other examples. A strap portion to which the blind guide 3370 is provided may be stretchable as a whole in order to provide some extensibility under tension although in some examples only a select region of the strap portion may extend in length. If the region of a strap portion to which a blind guide 3370 is provided is stretchable, the blind guide 3370 may also be formed to be stretchable (e.g. by using a knitting process that one able to blind guide to elastically extend with the strap on which it is formed). In some examples, a blind guide 3370 may be provided to a part of strap that is not stretchable (for example if the strap has a stretchable portion elsewhere along its length). In such an example, the blind guide 3370 may not be stretchable.

As shown in FIG. 12, an end portion blind guide 3371 may be provided to the patient-contacting side of the headgear strap 3301 to provide a tactile indication of the end portion 3361 of the strap portion. In use, once the strap portion has been fed through a slot in the frame 3500, the surface on which the blind guide 3371 is formed will be looped over the patient-contacting side of the headgear strap 3301.

5.3.4 Vent

In one form, the patient interface 3000 includes a vent structure 3400 constructed and arranged to allow for the washout of exhaled gases, e.g. carbon dioxide.

In certain forms the vent structure 3400 is configured to allow a continuous vent flow from an interior of the plenum chamber 3200 to ambient whilst the pressure within the plenum chamber is positive with respect to ambient. The vent structure 3400 is configured such that the vent flow rate has a magnitude sufficient to reduce rebreathing of exhaled $CO_2$ by the patient while maintaining the therapeutic pressure in the plenum chamber in use.

One form of vent structure 3400 in accordance with the present technology comprises a plurality of holes, for example, about 20 to about 80 holes, or about 40 to about 60 holes, or about 45 to about 55 holes.

The vent structure 3400 may be located in the plenum chamber 3200. Alternatively, the vent structure 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 System Architecture

Examples of the system(s) outlined herein may include one or more computing devices with one or more processor(s) programmed or configured to perform the various functions described herein. While examples may describe certain information being stored and/or processing tasks being performed by a particular device, it will be appreciated that alternative embodiments are contemplated in which such information and/or processing tasks are shared.

FIG. 18 shows a schematic view of an exemplary system 100 that may be used to perform various aspects of the present technology as described herein. It will be appreciated that system 100 may receive data from, and send data to, external systems, and may control the operation of components outside of the system 100. The system 100 may generally include a customisation server 102 that manages the collection and processing of data relating to the design and production of a customised component for a patient interface 3000. The customisation server 102 has processing facilities represented by one or more processors 104, memory 106, and other components typically present in such computing devices. It should be appreciated that the server 102, processors 104, and memory 106 may take any suitable form known in the art, for example a "cloud-based" distributed server architecture or a dedicated server architecture. In the exemplary embodiment illustrated the memory 106 stores information accessible by processor 104, the information including instructions 108 that may be executed by the processor 104 and data 110 that may be retrieved, manipulated or stored by the processor 104. The memory 106 may be of any suitable means known in the art, capable of storing information in a manner accessible by the processor 104, including a computer-readable medium, or other medium that stores data that may be read with the aid of an electronic device.

The processor 104 may be any suitable device known to a person skilled in the art. Although the processor 104 and memory 106 are illustrated as being within a single unit, it should be appreciated that this is not intended to be limiting, and that the functionality of each as herein described may be performed by multiple processors and memories, that may or may not be remote from each other and other components of the system 100. The instructions 108 may include any set of instructions suitable for execution by the processor 104. For example, the instructions 108 may be stored as computer code on the computer-readable medium. The instructions may be stored in any suitable computer language or format. Data 110 may be retrieved, stored or modified by processor 104 in accordance with the instructions 110. The data 110 may also be formatted in any suitable computer readable format. The data 110 may also include a record 112 of control routines or algorithms for implementing aspects of the system 100.

Although the server 102 in FIG. 18 is shown only to include memory 106, the server 102 may further be capable of accessing other external memories, data stores, or databases (not shown). For example, information processed at the server 102 may be sent to an external data store (or database) to be stored, or may be accessed by the server 102 from the external data store (or database) for further processing. Additionally, the system 100 may include multiple such data stores and/or databases. In some cases, the data stores or databases may be separately accessible, such as each being accessible to a different server. In other cases, the data stores or databases described herein may not necessarily be separate, but may be stored together but as part of separate files, folders, columns of a table in a common file, etc.

The server 102 may communicate with an operator workstation 114 to provide an operator with access to various functions and information. Such communication may be performed via network 120. The network 120 may comprise various configurations and protocols including the Internet, intranets, virtual private networks, wide area networks, local networks, private networks using communication protocols proprietary to one or more companies, whether wired or wireless, or a combination thereof.

The server 102 performing one or more operations may include using artificial intelligence and/or machine learning algorithms. The server 102 may be configured to generate training datasets and/or employ trained datasets (by the server 102 or external to the server 102) to make certain decisions.

The exemplary system 100 includes one or more user devices 130 equipped to obtain data relating to shape and/or size of a user's head or features thereof, as will be described further below. By way of example, the user devices 130 may include a mobile computing device such as smart phone 130A or tablet computer 130B, or personal computing device such as a laptop or desktop computer 130C, each equipped with an image sensor such as a camera. While the present technology will be described herein as utilising image data obtained using a camera, alternative embodiments are contemplated in which other sensors are used to obtain the data relating to shape and/or size of a user's head or features thereof. For example, such sensors may include stereoscopic cameras for capturing three-dimensional images, or a light detector capable of detecting reflected light from a laser or strobing/structured light source.

The exemplary system 100 may include one or more manufacturing systems 140, configured to manufacture customised patient interfaces or components thereof. The manufacturing system 140 may include one or more manufacturing apparatus 142 configured to physically produce a component of a patient interface 3000. In some examples, the manufacturing apparatus 142 is a knitting machine, such as a flat knitting machine or a circular knitting machine. In other examples, the manufacturing apparatus 142 is an additive manufacturing apparatus (e.g. a 3D printer). In examples, the manufacturing system 140 may include multiple types of manufacturing apparatus 142 for manufacture of different components of a patient interface 3300. The manufacturing apparatus 142 may comprise one or more controllers 144 for control of the operative hardware 146 (e.g. knitting hardware or 3D printing hardware), and dedicated user interfaces for operator input/monitoring of the manufacturing apparatus 142. The manufacturing apparatus 142 may also communicate with other components of the manufacturing system, for example a manufacturing server 150 managing production of custom patient interfaces in communication with the customisation server 102, and/or a manufacturing operator workstation 152.

In some examples, one or more of the manufacturing apparatus 142 is a laser cutter configured to cut out one or more components of the patient interface and/or modify produced one or more components (e.g., a component produced by another manufacturing apparatus 142). The laser cutter may provide flexibility to provide complex shapes with precision, repeatability, speed and/or automation. The laser cutter may also allow for components generated in large numbers to be customized with speed by modifying a length and/or a shape of the component based on the analysis results of the patient.

In some examples, one or more of the manufacturing apparatuses may be provided at a manufacturing plant, clinician's office, and/or at a patient's home. In some examples, a component may be produced at one location by one or more of the manufacturing apparatuses and then further modified by one or more of the manufacturing apparatuses at another location. In some examples, the one or more manufacturing apparatuses disposed at different location may receive instructions from the same manufacturing server 150, the same customisation server 102, and/or the same manufacturing operator workstation 152. In some examples, the one or more manufacturing apparatuses disposed at different location may report results of producing and/or modifying a component to the manufacturing server 150, the customisation server 102, and/or the manufacturing operator workstation 152.

In some examples, one or more of the devices in the exemplary system 100 may include communication circuitry configured to communicate with one or more other devices in the system 100 directly and/or via the network 120.

5.1 Methods for Customised Manufacture of Patient Interface

As illustrated in the flow diagrams of FIGS. 19A-19E, one aspect of the present technology is a method 7000 of producing at least one customised component of a patient interface 3000 for treatment of sleep disordered breathing. The customised component may be, for example, a component of a positioning and stabilising structure 3300, a plenum chamber 3200 or a seal-forming structure 3100. The customised component may be customised to an individual patient in one or more ways, such as in shape, size or by another property.

Figure 19A:
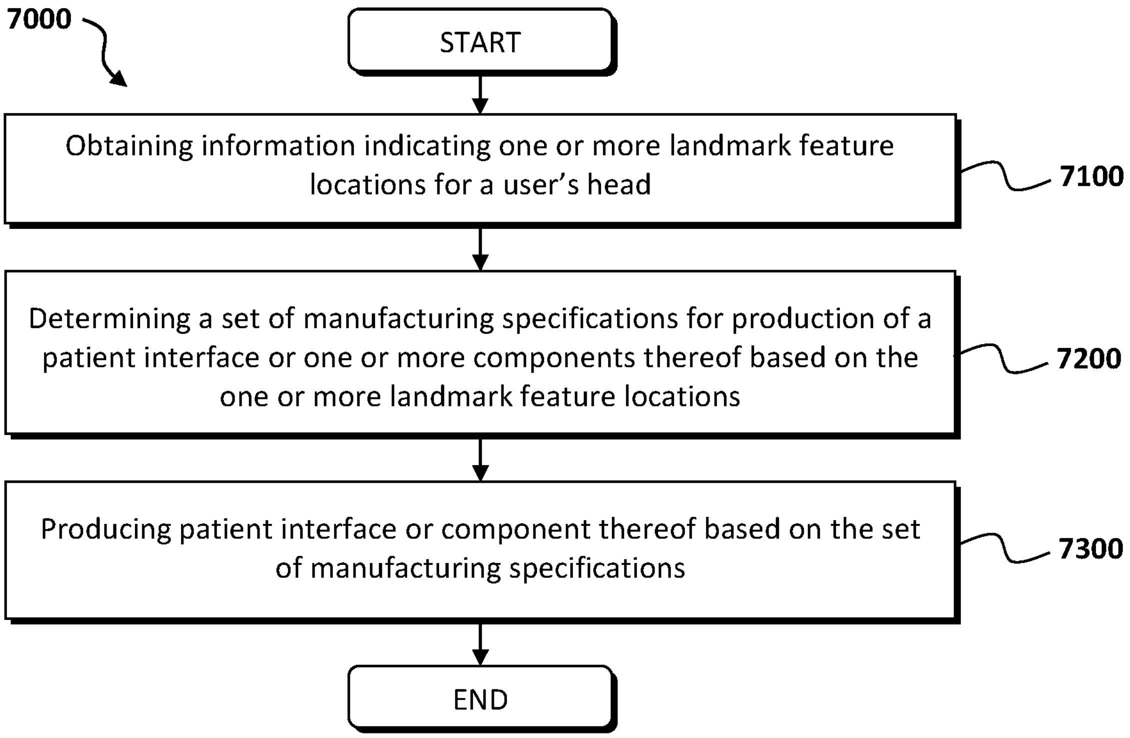

Referring to FIG. 19A, examples of the method 7000 may generally be characterized as including three phases: a user data capture phase 7100, a specification phase 7200, and a production phase 7300.

5.1.1.1 User Data Capture Phase

In order to produce a patient interface that provides effective treatment and is comfortable for the user to wear, it is desirable to customize the patient interface, or at least components thereof, to conform with the size and/or shape of the user's head (and more particularly facial features). In order to provide such customization, it is often necessary to collect information about the size and/or shape of the user's head—in a number of cases including the user's facial features.

In examples of the present technology, the user data capture phase 7100 includes obtaining information representative of one or more landmark feature locations for a user's head. As used herein, the term "landmark" shall refer to particular points, a region or a feature on a human head associated with elements of the head, including facial features. The location of a landmark may be defined, for example, relative to other landmarks or a fixed reference point. Examples of head landmarks may include, without limitation: a subnasale, a sellion, a tragion, a posterior-most point of the patient's head, a superior-most point of the patient's head, a lateral-most point of the orbital margin, an inferior-most point of the orbital margin, the Frankfort horizontal plane, and a coronal plane aligned with the tragion. Other examples of landmarks may be those features illustrated in any one of FIGS. 2C-2F.

5.1.1.1.1 Image Data Capture

Figure 19B:
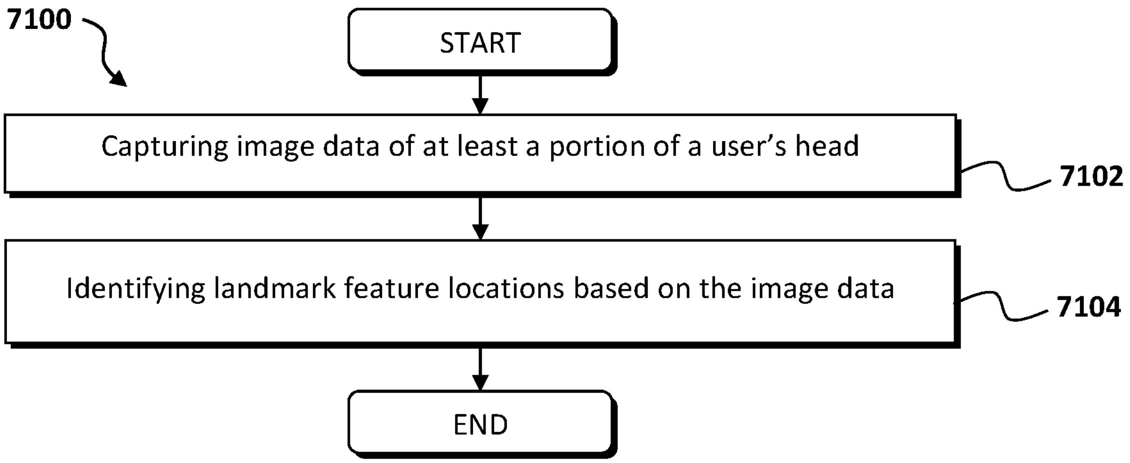

In examples, obtaining the relevant information in the user capture phase 7100 may include capturing image data of at least a portion of a user's head at 7102 of FIG. 19B, and identifying the landmark feature locations based on the image data at 7104. By way of example, the image data may be captured using a camera of the smart phone 130A, tablet 130B, or computer 130C.

U.S. Patent Publication No. 2018/0117272, U.S. Patent Publication No. 2019/0167934, U.S. Pat. Nos. 7,827,038, 8,254,637, and 10,157,477 describe exemplary methods and systems for capturing data (e.g., image data) of at least a portion of a user's head, determining patient features, and/or fitting features of a mask to a patient, the contents of which are incorporated herein by reference in their entirety. Other exemplary software tools for producing a three-dimensional model of a user's head, or portion thereof, may include: the "Capture" application available from Standard Cyborg, the "Scandy Pro" application available from Scandy, LLC; the "Beauty 3D" available from Guangzhou Zhimei Co., Ltd; the "Unre 3D FaceApp" available from UNRE AI LIMITED; and the "Bellus3D FaceApp" available from Bellus3D, Inc.

In alternative examples, the relevant information may be obtained by a user or clinician performing a series of measurements on the user's head, and a record of these measurements created and entered into the system 100—i.e. circumventing the requirement to capture image data.

5.1.1.1.2 Landmark Feature Identification

In examples, identifying landmark features of the user at 7104 may be based on two-dimensional image data. An exemplary method and system for determining landmark features of a user, and locations of same, based on two-dimensional image data is described in U.S. Patent Publication No. 2018/0117272.

Figure 19C:
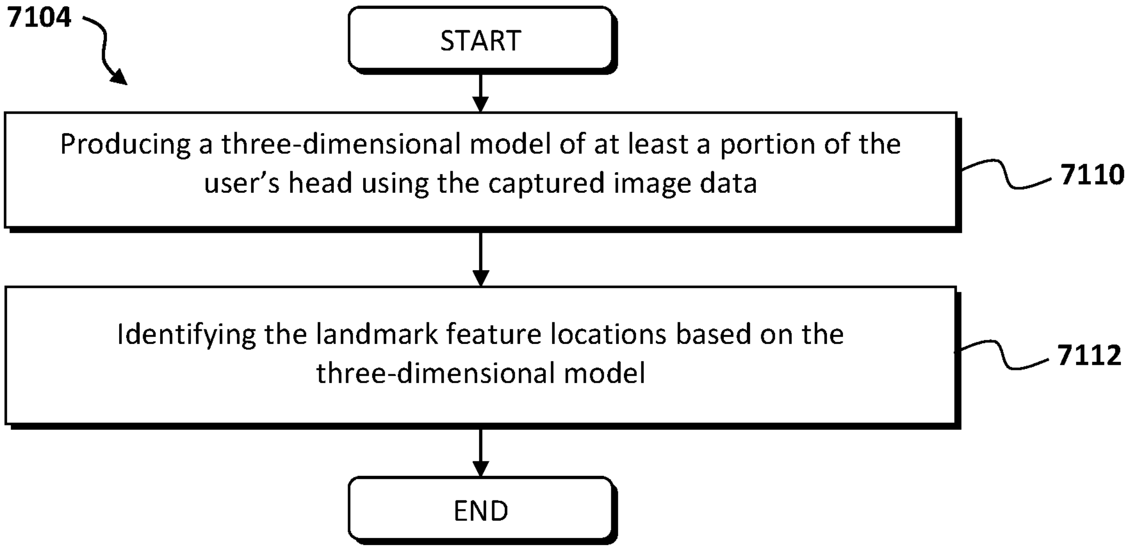
Figure 19D:
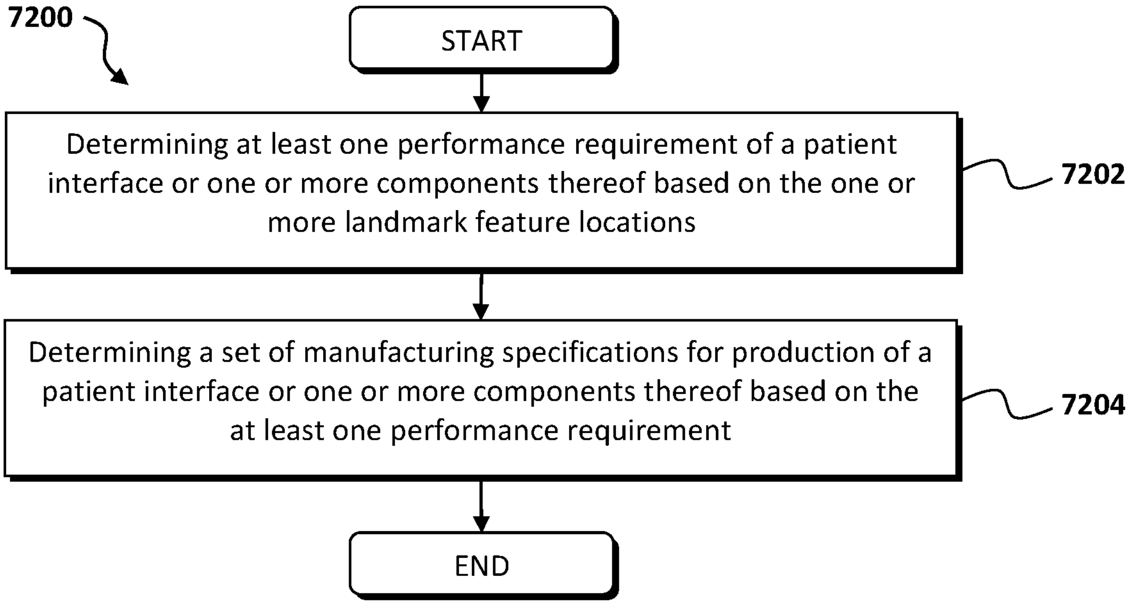

In examples, identifying landmark features based on the image data at 7104 may include producing a three-dimensional model of the user's face and/or head (at 7110 of FIG. 19C). The three-dimensional model may be analysed to identify landmark features of the user and determine locations of same at 7112. An exemplary method and system for identifying landmark features and locations of same from a three-dimensional model is described in U.S. Patent Publication No. 2019/0167934. As an example, the three-dimensional model may be generated based on data received from a 3D scanner, a stereo camera, and/or a plurality of images captured of the user's face and/or head from different positions and/or orientations of the capturing device and/or the patient.

In examples, local processing facilities at the point of capturing the image data (e.g. the smart phone 130A, tablet 130B, or computer 130C) may be used to identify the landmark features (including generation of the three-dimensional model in examples). In alternative examples, the image data may be communicated to remote processing facilities (e.g. customisation server 102) for further processing.

5.1.1.1.3 Relationships Between Landmark Features

In some forms of the present technology, the method 7000 may include identifying relationships between landmark features. Such relationships may provide information regarding anthropometric measurements of the user to inform customisation of the patient interface, or component thereof, for the user. By way of example, a relationship between landmark features may include distance (i.e. spacing between the features), and relative angle.

In examples, identifying a relationship between landmark features may include determining distance between two or more of a subnasale, a sellion, a tragion, a posterior-most point of the patient's head, a superior-most point of the patient's head, a lateral-most point of the orbital margin, an inferior-most point of the orbital margin, the Frankfort horizontal plane, and a coronal plane aligned with the tragion.

It will be appreciated that the landmark features (and their associated relationships) to be identified may be influenced by the design or configuration of the patient interface, or component thereof, to be manufactured—i.e. some landmark features will be relevant to certain designs or components, but not others. In examples, only select landmark features and their relationships may be assessed. In alternative examples, an entire set of landmark features from a list of possible landmark features that are capable of being identified may be assessed in order to allow use of the data set across a range of patient interfaces, or components thereof.

FIG. 20 shows a side view of a patient's head with a number of landmark feature spacings identified, described below. Each feature spacing is between a pair of landmark feature locations.

In examples a distance D1 between the subnasale and the coronal plane aligned with the tragion may be determined, the distance D1 being normal to said coronal plane. This landmark feature spacing may enable the spacing in the anterior-posterior axis between the patient's lip superior and the patient's ears to be accounted for in the design of a customised component for a patient interface 3000. In particular, this spacing may be useful in the design of a customised frame 3500 and/or a customised headgear strap 3301, for example.

In examples a distance D2 in the sagittal plane between the subnasale and the tragion may be determined. The distance D2 may be a direct distance in the sagittal plane including both the vertical component and a horizontal component (e.g. a diagonal distance in the sagittal plane between the subnasale and vertically superior tragion). Together with the horizontal distance D1 between the subnasale and the tragion, this distance D2 may enable the height of the ear with respect to the lower periphery of the patient's nose to be taken into account in the design of a customised component for a patient interface 3000. This spacing may be useful in the design of a customised frame 3500 and/or a customised headgear strap 3301, for example.

In examples a vertical distance D3 in the sagittal plane between the subnasale and the sellion may be determined. This distance D3 may enable the height of the patient's nose and/or the spacing between the lower periphery of the patient's nose and the patient's eyes to be accounted for in the design of customised component for a patient interface 3000. In particular, this spacing may be useful in determining the shape and/or size of a customised plenum chamber 3200 and/or a customised seal-forming structure 3100, for example.

In examples a distance D4 between the lateral-most point of the orbital margin and the coronal plane aligned with the tragion may be determined, the distance D4 being normal to said coronal plane. This spacing may enable the distance between the patient's ear and the patient's eye to be taken into account in the design of a customised component for a patient interface 3000. In particular this distance may be useful in determining the shape and/or size of a customised frame 3500 and/or a customised headgear strap 3301, for example.

In examples a vertical distance D5 between the subnasale and the superior-most point of the patient's head may be determined. This feature spacing may enable the height of the patient's head and the spacing between the lower periphery of the patient's nose and the top of the patient's head to be taken into account in the design of a customised component for a patient interface 3000. This feature spacing may be useful in determining the shape and/or size of a customised headgear strap 3301, for example.

In examples a vertical distance D6 between the superior-most point of the patient's head and the Frankfort horizontal plane may be determined. This feature spacing may enable the distance between top the patient's head and the patient's ear or lower orbital margin to be taken into account in the design of a customised component for a patient interface 3000. This distance may be useful in determining the shape and/or size of a customised headgear strap 3301, for example.

In examples a distance D7 between the rearmost point of the head and a coronal plane aligned with the tragion may be determined, the distance D7 being normal to said coronal plane. This feature spacing may enable the size of the patient's head and/or the distance between the patient's ear and the rear of the patient's head to be taken into account in the design of a customised component for a patient interface 3000. This distance may be useful in determining the shape and/or size of a customised headgear strap 3301, for example.

The preceding relationships are given by example only, and are not intended to be limiting to all forms of the present technology.

5.1.1.1.4 Physiological Data Capture

In some forms of the present technology, customisation of a component for use in respiratory therapy or treatment may be based at least in part on functional requirements which are not derived from information relating to landmark features.

In examples, such functional requirements may include a characteristic of a heat and moisture exchanger relating to absorption of heat and/or moisture from a volume of air of expired flow during patient exhalation, or vent performance. In examples, $CO_2$ saturation and/or moisture in exhaled breath may be used to determine functional requirements in this regard. Such physiological characteristics may be measured, for example, using standalone sensors, or sensors incorporated into existing equipment used by a user.

By way of example, a manufacturing specification for a heat and moisture exchanger may be determined based on moisture content to deliver improved comfort for a user—e.g. a lower than desirable moisture content may result in specification of a heat and moisture exchanger having a higher likelihood of capturing that water for use in humidification. Conversely, a heat and moisture exchanger having a lower likelihood of capturing water may be specified for a higher than desirable moisture content.

As a further example, desired venting characteristics may be determined based on $CO_2$ saturation and/or other factors such as physical nose size. For a mask, and more particularly a plenum chamber, venting characteristics may be influenced by geometry (e.g. physical deadspace) and/or the structure of the vent through which air flows. These may be specified accordingly.

5.1.1.2 Specification Phase

In the specification phase 7200, examples of the method 7000 include determining a set of manufacturing specifications for production of a patient interface, or one or more components thereof, based on the one or more landmark feature locations and/or relationships between same.

In examples, such specifications are determined based on one or more performance requirements of the component. Examples of such performance requirements may include one or more of: forces to be applied by or to the component, elasticity, dimensions (including size and relative angles of features of the component), tactile feel, breathability, heat dissipation, and/or positioning on the user's head. Such performance criteria may be influenced by one or more of: efficacy of delivery of the treatment (for example, sealing of the patient interface and/or reducing the likelihood of occlusion during use), user comfort (for example, the feel of the component to the touch, and relative positioning to avoid more sensitive areas of the user's head), and manufacturing considerations (for example, material costs and/or complexity of manufacture). It will be appreciated that the performance requirements for a component will be influenced by the one or more landmark feature locations and/or relationships between same, examples of which are described further below. In examples, the customised component specifications may be determined based in part on non-performance characteristics such as colour.

In examples, the performance requirements may be based on functional requirements which are not derived from the landmark feature locations and/or relationships between same, as described above.

The performance requirements and resulting manufacturing specifications will depend on the particular type or style of customised component to be produced. In examples, the customised component may include a headgear strap 3301 of a positioning and stabilising structure 3300 of the patient interface 3000. The headgear strap 3001 may be customised to a particular patient by being formed in a particular shape and/or size, based on the landmark feature locations and/or relationships, that results in a comfortable and stable fit for that particular patient. Exemplary headgear straps are described above with reference to FIGS. 7-17, and further considerations for determining manufacturing specifications for headgear straps are described below with reference to FIGS. 21-23. In another example, the customised component may include a customised frame 3500 of the patient interface 3000. The frame 3500 may be customised to a particular patient by being formed in a particular shape and/or size, based on the landmark feature locations and/or relationships, that results in a transfer of headgear forces to sealing forces in an optimal manner for that particular patient.

In examples, the performance requirements of one component of the patient interface may be influenced by properties or characteristics of another component. By way of example, for a customised headgear strap 3001 certain performance requirements may be determined in part by dimensions and/or configurations of a frame 3500 for use with that strap 3001. For example, positioning of headgear strap attachment points on the frame 3500 relative to one or more landmark feature locations or relationships is a factor requiring consideration when specifying characteristics of the headgear and/or its straps.

In examples, the manufacturing specifications may comprise material specifications. A particular material, or blend of materials, may be selected based on a performance requirement such as flexibility/rigidity, stretchability, or tactile feel. In some examples a material may be selected based on preferences of the patient for whom the customised component is being produced.

In examples, the manufacturing specifications may comprise construction technique specifications. For example, where the component is manufactured using mechanical manipulation of yarn—including interlooping (such as knitting, more particularly flat knitting or circular knitting), interweaving and/or intertwining (including braiding, knotting and crocheting)—manipulation techniques (for example, a knitting structure or stitch) may be selected based on performance requirements for the component. By way of example, a fine gauge high density knit structure may be used in some regions of a headgear strap to assist with achieving a specified strap tension to achieve a desired force at the patient's nose bridge. PCT Patent Application Publication No. WO2013026091A1 describes exemplary methods and systems for specification and manufacture of components of a patient interface having one or more portions constructed of a knitted fabric, the contents of which are incorporated herein by reference in their entirety.

In examples, determining a set of manufacturing specifications may comprise selecting a set of manufacturing specifications from a plurality of pre-existing sets of manufacturing specifications. In examples, determining a set of manufacturing specifications may comprise selecting a plurality of manufacturing specifications to form the set of manufacturing specifications from a plurality of pre-existing manufacturing specifications. Selection of pre-existing manufacturing specifications may be based on similarities between the one or more landmark feature locations and/or relationships determined for the user, and those associated with the pre-existing manufacturing specification.

In examples, a manufacturing specification may comprise a sensor to be incorporated into a component. In examples, the sensor may be produced by the manufacturing process used to produce the remainder of the component—for example a knitted or textile component may include formation of a textile sensor. In examples, the component may comprise a feature configured to receive and/or locate a sensor relative to the component—for example a pocket in which a sensor may be retained. In other examples, the component may comprise a sensor element configured to connect to a separate sensing device.

5.1.1.2.1 Examples of Specifications for Headgear

In one form of the present technology, the customised component comprises a headgear strap 3301 of a positioning and stabilising structure 3300 of the patient interface 3000.

In examples, determining the performance criteria of a headgear strap 3301 may include determining customised headgear strap dimensions. FIG. 2I shows a customised component in the form of a headgear strap 3301 according to one example of the present technology. The headgear strap 3301 forms part of a positioning and stabilising structure 3300 of a patient interface 3000 for treatment of the disordered breathing. The headgear strap 3301 is shown in a flattened state in FIG. 21. The headgear strap 3301 comprises a posterior strap portion 3305. The posterior strap portion 3305 is configured to lie against at least posterior surfaces of the patient's head in use. In some examples the posterior strap portion 3305 is configured to overlie or lie inferior to an occipital bone of the patient's skull.

In one form, determining customised headgear strap dimensions comprises determining at least one dimension of the posterior strap portion 3305 for the headgear strap 3301. The at least one dimension of the posterior strap portion 3305 may be a width of the posterior strap portion 3305, corresponding to the length of a posterior surface of the patient's head along which the posterior strap portion 3305 lies in use. Alternatively, or additionally, the at least one dimension of the posterior strap portion 3305 may be a height of the posterior portion, or a thickness.

The headgear strap 3301 shown in FIG. 21 also comprises a pair of upper strap portions 3310. Each upper strap portion 3310 is configured to lie on a respective side of the patient's head in use. In some forms, at least a portion of each upper strap portion 3310 may be located superior to an otobasion superior in use. Each upper strap portion 3310 may connect to another component of a positioning and stabilising structure 3300 of a patient interface 3000, such as a frame 3500 or a headgear conduit 3900. Alternatively, each upper strap portion 3310 may connect directly to a plenum chamber 3200 of a patient interface 3000.

In the example shown in FIG. 21, each upper strap portion 3310 extends from the posterior strap portion 3305 at an upper strap location 3310A. Additionally, each upper strap portion 3310 extends from the posterior strap portion 3305 in an upper strap direction 3310B. In FIG. 21, each upper strap location 3310A is indicated by a point in the general area of the posterior strap portion 3305 from which the upper strap portion 3310 extends. Similarly, each upper strap direction 3310B is indicated by a longitudinal axis along which the respective upper strap portion 3310 extends.

It should be appreciated that the headgear strap 3301 is shown in FIG. 21 in a flattened state and will in use have a three-dimensional shape matching the posterior curved surfaces of the patient's head. The upper strap directions 3310B are in this example substantially parallel to each other and substantially aligned with the length of the posterior strap portion 3305. In other examples the upper strap portions 3310 may not be parallel to each other or to the length of the posterior strap portion 3305.

In some examples, determining customised headgear strap dimensions comprises determining a length of each one of the pair of upper strap portions 3310. In some examples, determining customised headgear strap dimensions comprises determining the upper strap location 3310A on the posterior strap portion 3305 from which each upper strap portion 3310 extends. In some examples, determining customised headgear strap dimensions comprises determining the upper strap direction 3310B in which each upper strap portion 3310 extends from the posterior strap portion 3305.

By determining one or more of the size of a posterior strap portion 3305 and a length, location and direction for each upper strap portion 3310 of the headgear strap 3301, based on the head scan data received, the headgear strap 3301 can be customised to the specific patient to which the head scan data relates, such that the headgear strap 3301 fits the specific patient well, such as in a comfortable and stable manner.

FIG. 22 shows another customised component of a patient interface 3000 in the form of a headgear strap 3301 of a positioning and stabilising structure 3300. The headgear strap 3301 in this example also has a posterior strap portion 3305. The posterior strap portion 3305 may be configured to lie against posterior surfaces of the patient's head and/or neck. For example, the posterior strap portion 3305 may be configured to overlie or lie inferior to an occipital bone of the patient's skull. The headgear strap 3301 in this example comprises a pair of upper strap portions 3310 extending from the posterior strap portion 3305. The headgear strap shown in FIG. 22 may be a customised component produced by the method 7000. As described above, determining headgear strap dimensions may comprise determining at least one dimension of the posterior strap portion 3305, a length of each upper strap portion 3310, an upper strap location 3310A from which each upper strap portion 3310 extends, and/or an upper strap direction 3310B in which each upper strap portion 3310 extends.

As shown in FIG. 22, the headgear strap 3301 also comprises a pair of lower strap portions 3320. Each lower strap portion 3320 may be configured to lie on a respective side of the patient's head. In some examples, the lower strap portions 3320 are configured to lie at least partially inferior to the patient's ears. In some forms, at least a portion of each lower strap portion 3320 may be located inferior to an otobasion inferior in use. Each lower strap portion 3320 may connect to another component of a positioning and stabilising structure 3300 of a patient interface 3000, such as a frame 3500. Alternatively, each lower strap portion 3320 may connect directly to a plenum chamber 3200 of a patient interface 3000.

In the example shown in FIG. 22, each lower strap portion 3320 extends from the posterior strap portion 3305 at a lower strap location 3320A. Additionally, each lower strap portion 3320 extends from the posterior strap portion 3305 in a lower strap direction 3320B. In FIG. 22, each lower strap location 3320A is indicated by a point in the general area of the posterior strap portion 3305 from which the lower strap portion 3320 extends. Similarly, each lower strap direction 3320B is indicated by a longitudinal axis along which the respective lower strap portion 3320 extends.

It should be appreciated that the headgear strap 3301 is shown in FIG. 22 in a flattened state and will in use have a three-dimensional shape corresponding to curved surfaces of the patient's head. The lower strap directions 3320B are in this example angled with respect to each other. In other examples the lower strap directions 3320B may not be angled with respect to each other and may instead extend parallel with each other. In this example the upper strap directions 3310B are angled with respect to each other. In other examples the upper strap directions 3310B may be parallel.

Determining the length, location and direction of upper strap portions 3310 is described in relation to FIG. 2I. The same steps may be performed in the design of the headgear strap 3301 shown in FIG. 22. In addition, for the design of the headgear strap 3301 shown in FIG. 22, which has both upper strap portions 3310 and lower strap portions 3320, the step of determining customised headgear strap dimensions comprises determining a length of each one of the pair of lower strap portions 3320. In some examples, determining customised headgear strap dimensions comprises determining the lower strap location 3320A on the posterior strap portion 3305 from which each lower strap portion 3320 extends. In some examples, determining customised headgear strap dimensions comprises determining the lower strap direction 3320B in which each lower strap portion 3320 extends from the posterior strap portion 3305.

By determining one or more of the size of a posterior strap portion 3305 and a length, location and direction for each upper strap portion 3310 and lower strap portion 3320 of the headgear strap 3301, based on the head scan data received, the headgear strap 3301 can be customised to the specific patient to which the head scan data relates, such that the headgear strap 3301 fits the specific patient well, such as in a comfortable and stable manner.

FIG. 23 shows another customised component in the form of a headgear strap 3301. In this example the headgear strap 3301 comprises upper strap portions 3310, lower strap portions 3320 and a posterior portion 3305. The same methodology described above in relation to determining length, location and direction of each of the upper strap portions 3310 and lower strap portions 3320 may be performed during execution of the method 7000. One particular difference to the headgear straps 3301 shown in FIGS. 21 and 22 is that the headgear strap 3301 shown in FIG. 23 comprises a posterior portion 3305 in the form of a ring strap portion 3340. Features of a ring strap portion 3340 according to examples of the present technology are described above with reference to FIGS. 7 and 8, for example, and will not all be repeated here.

In some forms of the present technology, determining customised headgear strap dimensions comprises determining a length of a ring strap portion 3340 for the customised headgear strap. The ring strap portion 3340 may have a superior portion configured to overlay the parietal bones of the patient's head in use. Additionally, the ring strap portion 3340 may have an inferior portion configured to overlay or lie inferior to the occipital bone of the patient's head in use.

In some forms of the present technology, various features of the ring strap portion 3340 and headgear straps 3301 described in relation to FIGS. 7-17 are included in headgear straps 3301 produced by the method 7000, such as one or more of the rigidised portion 3345, superior stretchable portion 3346, inferior stretchable portion 3347, ventilation portions 3350, fastening portions 3360, blind guides 3370 and associated features.

An advantage of the use of the present technology to produce customised headgear straps 3301 is that the customised headgear straps 3301 may not require long fastening portions 3360. Since a headgear strap 3301 produced by method 7000 is customised to fit a specific patient, the patient may not need to adjust the headgear strap 3301 significantly. An intermediate portion 3363 of a fastening portion 3360 may not need to be particularly long, since there may only be a small range of adjustment required. In some examples the fastening portion 3360 may comprise a connection between an end portion 3361 of an upper or lower strap portion and an intermediate portion 3363 at a single point—for example a magnetic connection, or a mechanical connection such as a clip or a clasp. That is, there may be no need for adjustment in some scenarios if the headgear strap 3301 is customised within tight enough tolerances to suit a specific patient.

In examples, determining manufacturing specifications for a customised headgear strap 3301 may comprise determining a knitting structure for one or more portions of the headgear strap 3301. As described above with reference to FIGS. 7 and 8, the headgear strap 3301 may comprise different knitting structures in different regions. In examples, determining the manufacturing specifications may comprise determining a particular knitting structure required for one or more portions of the headgear strap to meet one or more performance requirements.

Also as described above, the upper strap portions 3310 and lower strap portions 3320 may be stretchable. Determining manufacturing specifications for a customised headgear strap 3301 may comprise determining a knitting structure for one or more stretchable portions of the headgear strap. The knitting structure may be determined based on the one or more landmark feature locations and/or relationships. In some examples, the knitting structure may be determined based on a length and/or a direction of a headgear strap portion (e.g. upper strap portion 3310 or lower strap portion 3320).

In some forms of the present technology, determining the manufacturing specifications may comprise determining the knitting structure such that, during use of the patient interface 3000, each of the stretchable portions of the headgear strap 3301, such as the upper strap portion 3310 and lower strap portion 3320, is tensioned with a respective predetermined tension. In some examples the method comprises determining a knitting structure such that when a patient dons the patient interface 3000, the headgear strap 3301 applies a predetermined force to a seal-forming structure 3100 of the patient interface. The predetermined force may be between about 3N and about 5N. In some examples the predetermined force may be about 4N.

In examples, the knitting structure may be determined such that, regardless of the length and/or direction of a particular strap portion of the headgear strap 3301, the tension in that strap portion when the patient interface 3000 is donned by the patient is a predetermined tension, which may for example be a tension balancing seal performance, stability and comfort. Determination of an appropriate knitting structure to achieve the predetermined tension may be based on characteristics of the user's head, such as the shape and/or size.

In some examples, different strap portions, such as the upper strap portions 3310 and lower strap portions 3320, may have different predetermined tensions in use. Determining the manufacturing specifications may include determining the knitting structure such that, when the patient interface 3000 is donned by the patient, each of the upper strap portions 3310 of the headgear strap 3301 is tensioned with a predetermined upper strap tension. Determining the manufacturing specifications may also comprise determining the knitting structure such that, when the patient interface 3000 is donned by the patient, each of the lower strap portions 3320 of the headgear strap 3301 is tensioned with a predetermined lower strap tension.

Determining the manufacturing specifications may comprise determining knitting structures to achieve a predetermined upper strap tension and lower strap tension based on the landmark feature locations and/or relationships. For example, some patient may require greater upper strap tensions and lesser lower strap tensions in comparison to other patients. An appropriate proportion of tensions in the upper strap portions 3310 and lower strap portions 3320 may be based on a particular patient's anatomy.

In some examples, the stretchability and/or rigidity needed for a headgear strap of a positioning and stabilising structure 3300 of the patient interface 3000 may depend on a cushion sealing characteristics. For example, the stretchability or rigidity of a headgear on sealing characteristic of a seal-forming structure may be different for different seal forming structures due to the positioning of the seal-forming structure on the patients face. The sealing required by certain seal-forming structures may need a positioning and stabilising structure 3300 that provides an angled stretch direction, while other certain seal-forming structures may need a flatter stretch direction.

Accordingly, the stretchability and/or rigidity of one or more straps of the headgear may be selected based on the type of the plenum chamber 3200 and/or the seal-forming structure 3100 the user is recommended by the system and/or selected by the user. In addition, the shape of the patient's face and/or head may be taken into account to determine the angle at which forces will be applied by the headgear to the seal-forming structure 3100 and whether the applied forces at the determined angles will provide sufficient force to provide the needed seal between the seal-forming structure 3100 and the patient's face when the plenum chamber is under pressure in use.

In addition to the other examples for providing a rigidised portion in the headgear, examples of the present technology may also provide a rigidised portion in the headgear as part of flat knitting and/or laser cutting. As part of the knitting, the rigidity may be customised by a themofusible material inlaid with a portion of the knit headgear, a rigidiser (e.g., a plastic rigidiser) inserted into a knitted channel in the headgear, and/or a rigid material (e.g., plastic) laminated with a knitted part of the headgear. In some examples, a determination may be made for a type of rigidiser to provide a patient with the knitted headgear. In some examples, the patient may be provided with a plurality of rigidisers that can be interchanged by the patient using an opening in the headgear strap. In other examples, producing the headgear may include inserting the rigidiser into the headgear as part of the knitting such that the rigidiser is fully enclosed by the knitting and not removable from the headgear by the patient.

As part of the laser cutting, the rigidity may be customised by a laser etching and/or heating technique to achieve rigid effect on the fabric surface. As an example, different rigidity may be provided in different portions of the headgear by laser cutting different features (e.g., different sized holes or lines having a different thickness) into the headgear. Portions of the headgear including larger holes may provide less rigidity and allow more stretching as compared to portions of the headgear including smaller holes or having no holes. In some examples, the different rigidity may be provided by partially cutting features into a surface of the headgear straps.

In some examples, the specification for the headgear may take into account that the stretch characteristic provided by the headgear are affected by plurality of factors. For examples, the stretch characteristic may be defined by knit structure (e.g., tubular, interlock, spacer, double jersey, or plain knit), material composition (e.g., Nylon, Polyethersulfone, Elastane, and/or Viscous Polybutylene Terephthalate, etc.), machine gauge (E14, 18, etc), and yarn denier. Selecting the specification for the headgear may include defining one or more of these factors for a patient based on the 3D model determined for the patient and/or the type of patient interface the patient will be using.

5.1.1.2.2 Examples of Specifications for Frames

In some examples of the present technology, the customised component comprises a frame 3500 of the patient interface. In such examples, determining customised component specifications at 7200 comprises determining customised frame dimensions. For example, in some examples the frame 3500 shown in FIG. 7 may be customised to a particular patient using the method 7000.

In examples determining customised frame dimensions may comprise determining a length of each one of a pair of upper arms of the frame 3500, each upper arm being configured to connect with a respective upper strap portion 3310 of a positioning and stabilising structure 3300. The upper strap portion 3310 may be a portion of a headgear strap 3301, for example. The headgear strap 3301 may also be a customised component. In some examples, determining customised frame dimensions comprises determining a direction at which each upper arm extends from a central portion of the frame 3500. A customised frame may advantageously be more likely than a one-size-fits-all frame to provide a stable and comfortable fit for a patient interface 3000.

In some examples, determining customised frame dimensions comprises determining a length of each one of a pair of lower arms of the frame 3500. Each lower arm may be configured to connect with a respective lower strap portion 3320 of the positioning and stabilising structure 3300. In some examples, the step of determining customised frame dimensions comprises determining a direction at which each lower arm extends from the central portion of the frame 3500.

In some examples, determining customised frame dimensions comprises determining a location from which each upper and lower arm of the frame 3500 extends from a central portion of the frame 3500.

In addition to headgear straps 3301 and frames 3500 as described above, additional components of patient interfaces may have specifications developed for manufacture of same. For example, the customised component may comprise a plenum chamber 3200 of the patient interface, and/or a seal-forming structure 3100 of the patient interface. By way of example, PCT Patent Application Publication No. WO2013026091A1 describes exemplary methods and systems for specification and manufacture of a knitted mask. As another example, United States Patent Application Publication No. 20170326320 describes a cushion having textile materials, the contents of which are incorporated herein by reference in their entirety.

It should also be appreciated that while examples have been discussed with reference to manufacture using knitting techniques, aspects of the present technology may utilise other manufacturing techniques—such as other methods of mechanical manipulation of yarn (including for the production of woven materials), forming of textiles, or additive manufacturing techniques—and the manufacturing specifications will be suited to the type of manufacture.

In some examples, any mask component, such as nasal cradle cushion, full face cushion, frame, chasses and/or tube may be customized by completely or partially including textile material based on analysis results of the patient. In some examples, the textile material be provided with a foam material. For a textile cushion, customized foam (e.g., polyurethane foam) may be included in the mask (e.g., an under cushion of an oral cushion and/or a nasal cushion may be formed from foam that is covered with the textile material). U.S. Patent Publication No. 2017/0326320 describes exemplary textile patient interfaces including foam, the contents of which are incorporated herein by reference in their entirety.

In some examples, a customized tooling for injection molding of the customized foam cushion may be 3D printed to reduce manufacturing cost. In this example, the foam may be molded into the 3D printed mold with the fabric in the mold instead of laminating the fabric at a later stage in the production process.

For a frame and/or chassis including a textile material, a laser cutter may be configured to trim the produced frame and/or chassis to a customized size and/or shape based on customized cushion geometry and/or the analysis results of the patient. In this example, the frame and/or chassis may be pre-manufactured in large quantity and customized to the desired size and/or shape by laser cutting to reduce the production time.

Identifying the landmark features and/or their location (e.g., at 7104 and/or 7112), identifying relationships between the landmark features, determining functional requirements (e.g., for a patient interface and/or one or more components thereof) (e.g., at 7202), and/or determining manufacturing specifications (e.g., at 7204) may include using artificial intelligence and/or machine learning algorithms. For example, a trained dataset may be used to identify the landmark features and/or their location. In some examples, the captured image data and/or the three dimensional models used to identify the landmark features may be used to train datasets. In another example, a trained data set may be used to identify manufacturing specifications based on the landmark features, their locations, and/or functional requirements.

5.1.1.3 Producing the Customised Component

Figure 19E:
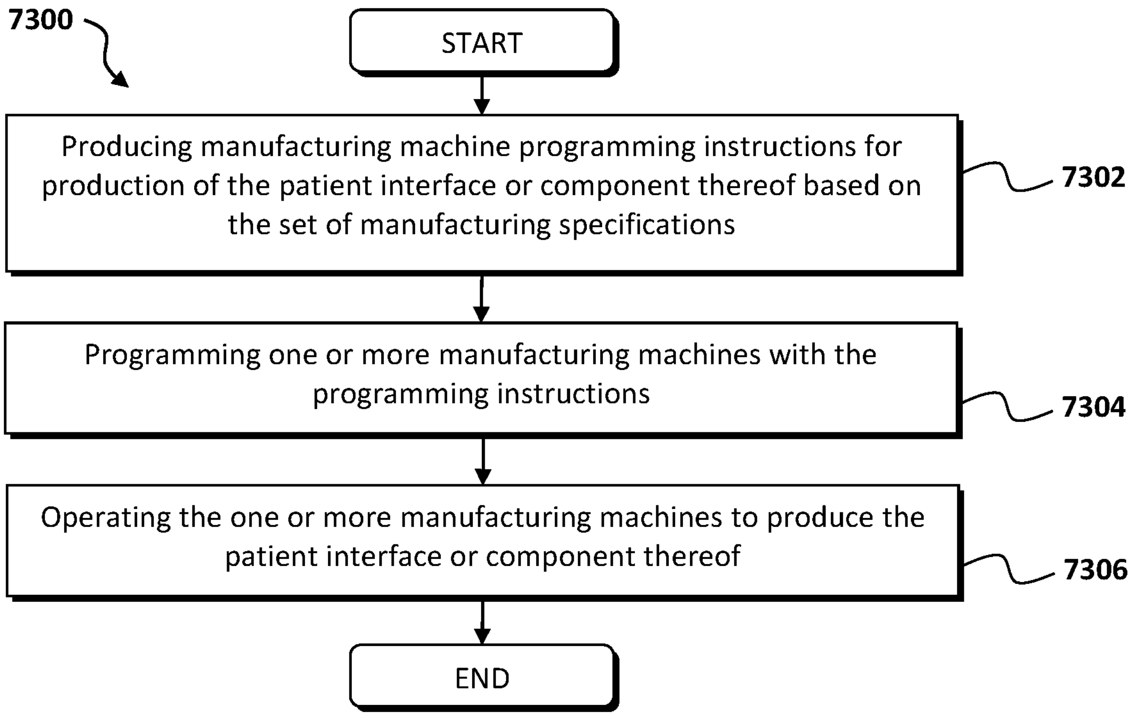

In examples, producing the patient interface or component thereof based on the set of manufacturing specifications at 7300 comprises producing manufacturing machine programming instructions for production of the patient interface or component thereof based on the set of manufacturing specifications at 7302 (see FIG. 19E). The manufacturing machines 142 are programmed with the manufacturing machine programming instructions at 7304, and are operated according to the manufacturing machine programming instructions to produce the patient interface or component thereof at 7306.

As described above, in some examples of the present technology the customised component to be produced is a headgear strap 3301. Producing a headgear strap 3301 at 7300 may comprise knitting the headgear strap 3301. The headgear straps 3301 shown in FIGS. 7, 8, 16 and 21-23 may be formed by knitting, in some examples. In some forms of the technology, the step 7300 of forming the headgear strap 3301 comprises knitting the headgear strap 3301 by flat knitting. In other forms of the present technology the method 7000 comprises knitting the headgear strap 3301 by circular knitting. Knitting may have an advantage in that minimal further processing (if any) of the headgear strap 3301 may be required prior to providing the headgear strap 3301 to the patient. PCT Patent Application Publication No. WO2013026091A1 further describes exemplary methods and systems for manufacture of a knitted patient interface or components thereof.

In some examples, producing the customised component at 7300 comprises additive manufacturing (for example, 3D printing) of the customised component. The manufacturing machines 142 may comprise a 3D printer to print the customised component, for example one or more of a frame 3500, plenum chamber 3200 or seal-forming structure 3100. The manufacturing machines 142 may comprise a laser cutter to cut-out and/or modify a customised component, for example one or more of a frame 3500, plenum chamber 3200 or seal-forming structure 3100.

5.1.1.3.1 Producing Manufacturing Machine Programming Instructions

In examples, the manufacturing machine programming instructions for production of the patient interface or component thereof may be generated automatically based on the set of manufacturing specifications. In examples, the manufacturing machine programming instructions may be generated from a model of the patient interface or component embodying the set of manufacturing specifications. Software tools are known for producing manufacturing machine programming instructions from two-dimensional and three-dimensional models, for example the STOLL-Autocreate™ tool from H. STOLL AG & Co. KG., and the SDS-ONE APEX™ series tool from SHIMA SEIKI MFG., LTD, for the production of knitting machine programming instructions.

In the example of a knitted product or component, the manufacturing specifications may specify parameters such as yarn type, stitch type and/or spacing to achieve certain performance requirements. Aspects of the programming instructions, such as the number of stitches required to achieve the specified dimensions, or structures required to transition between different regions, may be determined automatically.

Figure 19F:
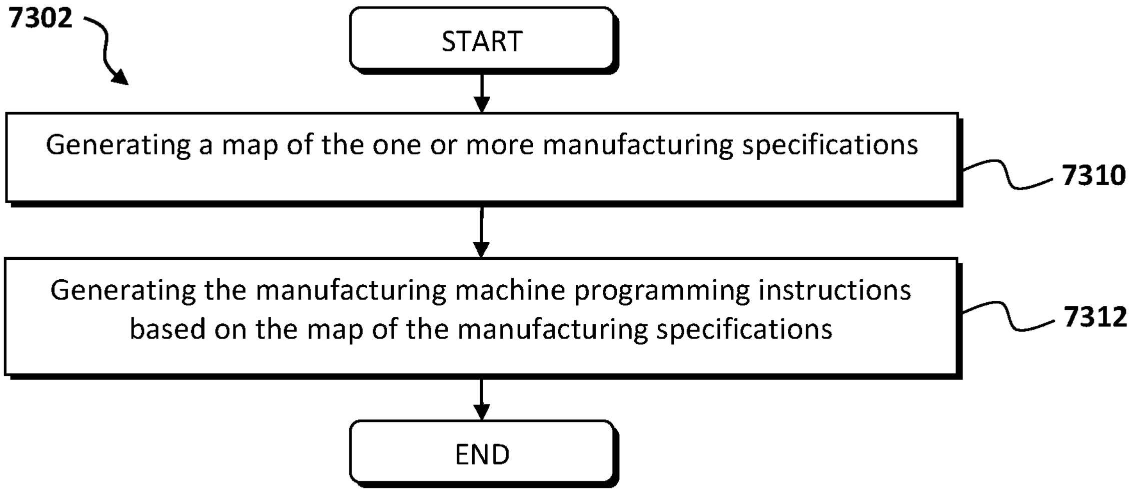

In examples, producing manufacturing machine programming instructions for production of the patient interface or component thereof based on the set of manufacturing specifications at 7302 comprises generating a map representing the one or more manufacturing specifications at 7310 (see FIG. 19F). In such examples, producing the manufacturing machine programming instructions at 7302 comprises generating the instructions based on the map representing the manufacturing specifications at 7312.

In an example, the map may comprise a two-dimensional model of the patient interface or component thereof, e.g. one or more two-dimensional images. In examples, details of the manufacturing specifications may be supplied by visually coding the model—i.e. certain manufacturing specifications may be obtained by visual recognition of characteristics of the map. In an example, the map may comprise a three-dimensional model of the patient interface or component thereof. In such an example, details of the manufacturing specifications may be encoded into the three-dimensional model.

In examples the map may be generated at a first processing facility, for example customisation server 102, and communicated to the appropriate manufacturer system 140 for generation of the manufacturing machine programming instructions. In other examples, the generation of the map and the manufacturing machine programming instructions may be performed at a single processing facility, for example by generating the map using a first software application, and generating the manufacturing machine programming instructions using a second software application.

In examples, the map may be converted into a model from which the manufacturing machine programming instructions may be generated. In an alternative example, the manufacturing specifications may be embodied in a map configured to be converted directly into the manufacturing machine programming instructions. In examples, the set of manufacturing specifications may be converted into the manufacturing machine programming instructions without an intermediary model or map being generated.

In examples, the set of manufacturing specifications may be used to modify a pre-existing template from which the manufacturing machine programming instructions are generated. Such templates may have predefined baseline rules associated with them, for example relating to manufacturing constraints, or universal performance requirements for a particular component design. In exemplary embodiments, such templates may include predefined regions of the component design, wherein the manufacturing specifications are used to modify parameters of each predefined region.

5.1.1.4 Distribution of Customised Component

In examples, following production of the customised patient interface or component thereof, an automated distribution system may be used to manage delivery to the user. In examples, the customised patient interface or component thereof may be delivered directly to the user from the facilities of the manufacturing system 140, or to a designated collection point or address.

In examples in which multiple components are to be produced, or at least supplied together with at least one customised component, an assembly phase may be performed. In examples, assembly may be performed by the vendor of the patient interface. Where the manufacturer of the customised component is a third party, the customised component may be delivered to a facility of the vendor for assembly with other components prior to delivery to the user.

5.1.1.5 Matching of User to Existing Products

According to an aspect of the present technology, user-specific data (e.g. measurements obtained from the user, or user profile information) may be used to select a patient interface component from a group of pre-existing component configurations having associated manufacturing specifications and programming instructions. For example, the selection may be based on a comparison between user-specific data and a data record relating to information associated with the pre-existing component configurations.

In examples, the pre-existing component configurations may be developed based on one or more sets of data representative of landmark features of heads representative of a user base. For example, a set of data may comprise a model of a human head having characteristics associated with profile categories such as gender, age, or build. Such models may be trained, for example using artificial intelligence and/or machine learning algorithms. Manufacturing specifications may be developed based on analysis of such representative models, and programming instructions generated from same.

5.1.1.6 Using Feedback to Modify Specification and/or Update Models

According to an aspect of the present technology, feedback from the user, clinician and/or manufacturing operator may be used to update parameters and/or models used to perform one or more of the above discussed operations (e.g., identifying the landmark features and/or their location, identifying relationships between landmark features, determining functional requirements, and/or determining manufacturing specifications). The feedback may be received via a user interface displayed on the RPT device, the user devices 130, the operator workstation 114, and/or the manufacturing operator workstation 152.

The user may provide feedback after receiving the customized patient interface. The user may input information indicating how well the patient interface fits when the patient interface is first used, after a predetermined period of time (e.g., after receiving or starting to use the patient interface), and/or after a predetermined amount of use. The user may be asked predefined questions about different aspects of the patient interface and/or asked to rate different features of the mask. The clinician may input feedback received from the user and/or feedback based on observing the user using the patient interface. The manufacturing operator may provide feedback based on the customized patient interfaces being produced by the manufacturing apparatus 142. For example, the manufacturing operator may inspect the manufactured patient interface and input defects in the patient interface caused by the manufacturing process.

The feedback from the user, clinician and/or manufacturing operator may be used to modify manufacturing specifications and/or update models used (e.g., by artificial intelligence and/or machine learning algorithms) to identify the landmark features and/or their location, to identify relationships between landmark features and/or to identify manufacturing specifications.

5.1.1.7 Example of Using Flat Knitting to Produce a Component of a Positioning and Stabilising Structure One or more operations described for using flat knitting to produce a component of a positioning and stabilising structure may be used in combination with one or more operations described with reference to other examples of the present technology (e.g., one or more operations described with reference to FIGS. 19A-19E). Producing the positioning and stabilising structure may include scanning a user's face and/or head, analysing the scanned data to identify positioning and stabilising structure (e.g., size, curvature and/or stretch characteristics) based on the results of the analysis, sending the design layout to a flat knit program to refine the knitting structure including the pattern, knitting one or more the positioning and stabilising structures, and shipping the positioning and stabilising structures to the end user for a first trial.

In some examples, scanning the user's face and/or head may include using a 3D scanning application, such as the 3D scanner application provided by ALL3DP, installed on a user's or a clinician's portable device (e.g., a user device 130). The 3D scanning application may provide an alternative to high-priced scanning hardware and/or software and provide a solution that is simple to use and portable.

In some examples, the positioning and stabilising structure or another component of the patient interface, may be produced with features allowing the end user and/or a clinician to further customize the patient interface. The positioning and stabilising structure may include features allowing a user to trim a strap of the patient interface to a preferred length at home. In a flat knit, the knitter can program one or more partition lines on the strap (e.g., using a bind-off and cast-on technique), allowing for the strap to be shortened to the position of the partition line without causing any fraying problem after the cut.

5.1.1.8 Example of Using Laser Cutting to Produce a Component of a Positioning and Stabilising Structure One or more operations described for using laser cutting technology to produce a component of a positioning and stabilising structure may be used in combination with one or more operations described with reference to other examples of the present technology (e.g., one or more operations described with reference to FIGS. 19A-19E). Producing the positioning and stabilising structure may include scanning a user's face and/or head (e.g., using a 3D scanning application), analysing the scanned data to identify positioning and stabilising structure (e.g., size, curvature and/or stretch characteristics) based on the results of the analysis, sending drawing outline to a laser cutting program, controlling a laser cutter to cut one or more the positioning and stabilising structures, and shipping the positioning and stabilising structures to the end user for a first trial.

Laser cutting the positioning and stabilising structure may include adding one or more perforated regions to guide a user in trimming one or more straps of the patient interface to a preferred length at home. In some examples, the positioning and stabilising structure may be etched by the laser cutter (e.g., to a predetermined depth of the strap) to provide indicators to a user of locations where straps may be cut to a preferred length.

Laser cutting may be include modifying the positioning and stabilising structure to increase elasticity of the positioning and stabilising structure by including additional cut-outs (e.g., holes) or etches in the straps. Laser cutting may be used to modify other components of the patient interface. For example, the mask frame and/or chassis may be cut to desired length and/or shape using laser cutting technology.

5.2 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller (e.g., provided on or coupled to the circuit board 4202), a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

5.2.1 RPT Device Mechanical & Pneumatic Components

An RPT device may comprise one or more of the following components in an integral unit. In an alternative form, one or more of the following components may be located as respective separate units.

5.2.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.2.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.2.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller.

In other forms, a pressure generator 4140 may be a piston-driven pump, a pressure regulator connected to a high pressure source (e.g. compressed air reservoir), or a bellows.

5.2.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.2.1.4.1 Flow Rate Sensor

A flow rate sensor in accordance with the present technology may be based on a differential pressure transducer, for example, an SDP600 Series differential pressure transducer from SENSIRION.

In one form, a signal representing a flow rate from the flow rate sensor is received by the central controller.

5.2.1.4.2 Pressure Sensor

A pressure sensor in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor is received by the central controller.

5.2.1.4.3 Motor Speed Transducer

In one form of the present technology a motor speed transducer is used to determine a rotational velocity of the motor 4144 and/or the blower 4142. A motor speed signal from the motor speed transducer may be provided to the therapy device controller. The motor speed transducer may, for example, be a speed sensor, such as a Hall effect sensor.

5.2.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.2.2 RPT Device Electrical Components 5.2.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.2.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller.

In one form, the input device 4220 may be constructed and arranged to allow a person to select a value and/or a menu option.

5.2.3 RPT Device Algorithms

As mentioned above, in some forms of the present technology, the central controller may be configured to implement one or more algorithms expressed as computer programs stored in a non-transitory computer readable storage medium, such as memory 4260. The algorithms are generally grouped into groups referred to as modules.

5.3 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.3.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.4 Humidifier 5.4.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.4.2 Humidifier Components 5.4.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.4.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.4.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.4.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.4.2.5 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.5 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6s, peak inspiratory flow rate Qpeak 0.4 L/s, exhalation time Te 2.4s, peak expiratory flow rate Qpeak −0.5 L/s. The total duration of the breath, Ttot, is about 4s. The person typically breathes at a rate of about 15 breaths per minute (BPM), with Ventilation Vent about 7.5 L/min. A typical duty cycle, the ratio of Ti to Ttot, is about 40%.

5.6 Glossary

For the purposes of the present technology disclosure, in certain forms of the present technology, one or more of the following definitions may apply. In other forms of the present technology, alternative definitions may apply.

5.6.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.6.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.6.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.6.2 Anatomy 5.6.2.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture. Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.6.2.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.6.2.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.6.3 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.6.4 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.6.4.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.6.4.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.6.4.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.6.4.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.7 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms “a”, “an”, and “the” include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms “comprises” and “comprising” should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms “first” and “second” may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.8 REFERENCE SIGNS LIST | |
|---|---|
| System | 100 |
| Customisation server | 102 |
| Processors | 104 |
| Memory | 106 |
| Processor-readable instructions | 108 |
| Data | 110 |
| Record | 112 |
| Operator workstation | 114 |
| Network | 120 |
| User device | 130 |
| Manufacturing system | 140 |
| Manufacturing apparatus | 142 |
| Controller | 144 |
| Operative hardware | 146 |
| Manufacturing server | 150 |

-continued

| 5.8 REFERENCE SIGNS LIST | |
|---|---|
| Manufacturing operator workstation | 152 |
| Patient | 1000 |
| Bed partner | 1100 |
| Patient interface | 3000 |
| Seal-forming structure | 3100 |
| Plenum chamber | 3200 |
| Chord | 3210 |
| Superior point | 3220 |
| Inferior point | 3230 |
| Positioning and stabilising structure | 3300 |
| Headgear strap | 3301 |
| Superior portion of the ring strap portion | 3302 |
| Inferior portion of the ring strap portion | 3304 |
| Posterior portion | 3305 |
| Upper strap portions | 3310 |
| Upper strap location | 3310A |
| Upper strap direction | 3310B |
| Lower strap portions | 3320 |
| Lower strap location | 3320A |
| Lower strap direction | 3320B |
| Headgear clip | 3322 |
| Overhead strap portion | 3330 |
| Neck strap portion | 3334 |
| Buckle | 3335 |
| Ring strap portion | 3340 |
| Inside periphery of the ring strap portion | 3341 |
| Outside periphery of the ring strap portion | 3342 |
| Inferior edge of the ring strap portion | 3343 |
| Rigidised portion | 3345 |
| Superior stretchable portion | 3346 |
| Inferior stretchable portion | 3347 |
| Ventilation portion | 3350 |
| Inferior edge of the ventilation portion | 3351 |
| Fastening portion | 3360 |
| End portion | 3361 |
| Hook portion | 3362 |
| Intermediate portion | 3363 |
| Loop portion | 3364 |
| Visual guide | 3366 |
| Blind guide | 3370 |
| End portion blind guide | 3371 |
| Vent structure | 3400 |
| Frame | 3500 |
| Upper strap connection point | 3510 |
| Connection port | 3600 |
| Forehead support | 3700 |
| Headgear conduits | 3900 |
| Lateral portion | 3901 |
| Junction | 3903 |
| RPT device | 4000 |
| External housing | 4010 |
| Upper portion | 4012 |
| Lower portion | 4014 |
| Panel | 4015 |
| Chassis | 4016 |
| Handle | 4018 |
| Pneumatic block | 4020 |
| Air filter | 4110 |
| Inlet air filter | 4112 |
| Outlet air filter | 4114 |
| Muffler | 4120 |
| Inlet muffler | 4122 |
| Outlet muffler | 4124 |
| Pressure generator | 4140 |
| Blower | 4142 |
| Motor | 4144 |
| Anti - spill back valve | 4160 |
| Air circuit | 4170 |
| Supplemental oxygen | 4180 |
| Electrical components | 4200 |
| Printed circuit board assembly (PCBA) | 4202 |
| Electrical power supply | 4210 |
| Input devices | 4220 |
| Transducers | 4270 |
| Humidifier | 5000 |
| Humidifier inlet | 5002 |
| Humidifier outlet | 5004 |

-continued

| 5.8 REFERENCE SIGNS LIST | |
|---|---|
| Humidifier base | 5006 |
| Humidifier reservoir | 5110 |
| Conductive portion | 5120 |
| Humidifier reservoir dock | 5130 |
| Locking lever | 5135 |
| Water level indicator | 5150 |
| Heating element | 5240 |
| Method | 7000 |
| User data capture phase | 7100 |
| Step | 7102 |
| Step | 7104 |
| Step | 7110 |
| Step | 7112 |
| Specification phase | 7200 |
| Step | 7202 |
| Step | 7204 |
| Production phase | 7300 |
| Step | 7302 |
| Step | 7304 |
| Step | 7306 |
| Step | 7310 |
| Step | 7312 |

The invention claimed is:

1. A processor-implemented method for producing a customised patient respiratory interface component comprising a headgear strap of a positioning and stabilising structure for a patient interface, the method comprising:

receiving, using communication circuitry, data representative of one or more landmark features of a head of a human and data representative of one or more functional requirements associated with the human;

identifying, using at least one processor, one or more landmark feature locations of the landmark features based on the data representative of one or more landmark features;

identifying, using the at least one processor, at least one relationship between two or more of the landmark feature locations, wherein identifying the at least one relationship between the two or more of the landmark feature locations comprises determining a distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion;

determining, using the at least one processor, a set of manufacturing specifications for production of the patient respiratory interface component based on the one or more landmark feature locations and based on the data representative of the one or more functional requirements, wherein the set of manufacturing specifications comprises headgear strap dimensions, wherein determining the set of manufacturing specifications is further based at least in part on the at least one relationship between the two or more of the landmark feature locations;

determining, as part of the set of manufacturing specifications for production of the patient respiratory interface component, at least one knitting structure specification to be used for at least one portion of a one-piece headgear strap; and causing one or more manufacturing machines to produce the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

2. The method of claim 1, further comprising the step of capturing at least a portion of the data representative of one or more landmark features with an image sensor.

3. The method of claim 1, wherein the data representative of one or more landmark features comprises two-dimensional image data.

4. The method of claim 1, wherein the data representative of one or more landmark features comprises three-dimensional image data.

5. The method of claim 1, wherein identifying the at least one relationship between the two or more of the landmark feature locations comprises determining a distance in the sagittal plane between the subnasale and the tragion.

6. The method of claim 1, wherein identifying the at least one relationship between the two or more of the landmark feature locations comprises determining a vertical distance in the sagittal plane between the subnasale and the sellion.

7. The method of claim 1, wherein identifying the at least one relationship between the two or more of the landmark feature locations comprises determining a distance between the subnasale and the coronal plane aligned with the tragion, the distance being normal to said coronal plane.

8. The method of claim 1, wherein identifying the at least one relationship between the two or more of the landmark feature locations comprises determining a distance between the lateral-most point of the orbital margin and the coronal plane aligned with the tragion, the distance being normal to said coronal plane.

9. The method of claim 1, wherein identifying the at least one relationship between the two or more of the landmark feature locations comprises determining a vertical distance between the subnasale and the superior-most point of the head.

10. The method of claim 1, wherein identifying the at least one relationship between the two or more of the landmark feature locations comprises determining a vertical distance between the superior-most point of the head and the Frankfort horizontal plane.

11. The method of claim 1, wherein identifying the at least one relationship between the two or more of the landmark feature locations comprises determining a distance between a rearmost point of the head and a coronal plane aligned with the tragion, the distance being normal to said coronal plane.

12. The method of claim 1, comprising the step of determining, using the at least one processor, at least one performance requirement for the patient respiratory interface component based on the one or more landmark feature locations.

13. The method of claim 12, wherein the at least one performance requirement comprises one or more of: a force to be applied by or to the component, elasticity, dimensions, tactile feel, breathability, and positioning on the head.

14. The method of claim 12, wherein the patient respiratory interface component comprises a plurality of regions, and at least one performance requirement is determined for each region.

15. The method of claim 12, wherein the at least one performance requirement is determined based at least in part on properties of another component of the patient interface intended for use with the customised patient respiratory interface component.

16. The method of claim 12, wherein determining the set of manufacturing specifications is based at least in part on the at least one performance requirement.

17. The method of claim 1, wherein the set of manufacturing specifications comprise at least one material specification.

18. The method of claim 1, wherein the set of manufacturing specifications comprise at least one construction technique specification.

19. The method of claim 1, wherein the set of manufacturing specifications comprise at least one dimension specification.

20. The method of claim 1, wherein determining the set of manufacturing specifications comprises selecting the set of manufacturing specifications from a plurality of pre-existing sets of manufacturing specifications.

21. The method of claim 20, wherein selecting the set of pre-existing manufacturing specifications is based on a comparison between the one or more landmark feature locations determined for the human, and one or more landmark feature locations associated with the set of pre-existing manufacturing specifications.

22. The method of claim 1, wherein determining the set of manufacturing specifications comprises selecting a plurality of manufacturing specifications to form the set of manufacturing specifications from a plurality of pre-existing manufacturing specifications.

23. The method of claim 1, further comprising producing, using the at least one processor, manufacturing machine programming instructions for production of the patient interface or component thereof based on the set of manufacturing specifications, wherein producing the patient respiratory interface component comprises programming the at least one manufacturing machine with the manufacturing machine programming instructions, and operating the at least one manufacturing machine according to the manufacturing machine programming instructions.

24. The method of claim 23, wherein producing the manufacturing machine programming instructions comprises generating a map representing the set of manufacturing specifications, and generating the manufacturing machine programming instructions based on the map.

25. The method of claim 24, wherein producing the manufacturing machine programming instructions comprises generating a model of the patient respiratory interface component based on the set of manufacturing specifications, and generating the manufacturing machine programming instructions based on the model.

26. The method of claim 1, wherein producing the patient respiratory interface component comprises mechanical manipulation of yarn to produce the component.

27. The method of claim 1, wherein the at least one knitting structure specification to be used is determined based on a length and/or a direction of the at least one portion of the one-piece headgear strap.

28. The method of claim 27, wherein causing one or more manufacturing machines to produce the patient respiratory interface component based on the set of manufacturing specifications further comprises at least one of flat knitting and circular knitting.

29. The method of claim 1, wherein the set of manufacturing specifications comprises at least one dimension of a posterior strap portion for the headgear strap, the posterior strap portion configured to lie against at least posterior surfaces of the head in use.

30. The method of claim 1, wherein the set of manufacturing specifications comprises a length of each one of a pair of upper strap portions for the headgear strap, each upper strap portion being configured to lie on a respective side of the head in use.

31. The method of claim 1, wherein the set of manufacturing specifications comprises an upper strap location on a posterior strap portion for the headgear strap from which each one of a pair of upper strap portions for the headgear strap extends.

32. The method of claim 1, wherein the set of manufacturing specifications comprises an upper strap direction in which one of a pair of upper strap portions for the headgear strap extends from a posterior strap portion for the headgear strap.

33. The method of claim 1, wherein the set of manufacturing specifications comprises a length of each one of a pair of lower strap portions for the headgear strap, each lower strap portion being configured to lie on a respective side of the head in use.

34. The method of claim 1, wherein the set of manufacturing specifications comprises a lower strap location on a posterior strap portion for the headgear strap from which each one of a pair of lower strap portions extends.

35. The method of claim 1, wherein the set of manufacturing specifications comprises a length of a ring strap portion for the headgear strap, the ring strap portion having a superior portion configured to overlay the parietal bones of the head in use and having an inferior portion configured to overlay or lie inferior to the occipital bone of the head in use.

36. The method of any one of claim 1, wherein the set of manufacturing specifications is determined such that when the patient interface is donned by the human in use, the headgear strap applies a predetermined force to a seal-forming structure of the patient interface.

37. The method of claim 36, wherein the predetermined force is between 3N and 5N.

38. The method of claim 37, wherein the predetermined force is 4N.

39. The method of claim 1, wherein the patient respiratory interface component comprises a frame of the patient interface.

40. The method of claim 39, wherein the set of manufacturing specifications comprises frame dimensions.

41. The method of claim 39, wherein the set of manufacturing specifications comprises a length of each one of a pair of upper arms of the frame, each upper arm being configured to connect with a respective upper strap portion of a positioning and stabilising structure in use.

42. The method of claim 39, wherein the set of manufacturing specifications comprises a direction at which each one of a pair of upper arms of the frame extends from a central portion of the frame.

43. The method of claim 39, wherein the set of manufacturing specifications comprises a length of each one of a pair of lower arms of the frame, each lower arm being configured to connect with a respective lower strap portion of a positioning and stabilising structure in use.

44. The method of claim 39, wherein the set of manufacturing specifications comprises a direction at which each one of a pair of lower arms of the frame extends from a central portion of the frame.

45. The method of claim 1, wherein the patient respiratory interface component comprises a plenum chamber of the patient interface.

46. The method of claim 1, wherein the patient respiratory interface component comprises a seal-forming structure of the patient interface.

47. The method of claim 1, wherein the set of manufacturing specifications identify specifications for a headgear strap of a positioning and stabilising structure for a patient interface and include the at least one knitting structure specification material composition, yarn denier, and/or machine gauge for producing the headgear strap, wherein the one or more of manufacturing specifications define a stretch characteristic of the positioning and stabilising structure.

48. The method of claim 1, wherein the determined at least one knitting structure specification is further based the headgear strap dimensions.

49. A system for producing a customised patient respiratory interface component comprising a headgear strap of a positioning and stabilising structure for a patient interface, the system comprising:

one or more processors for receiving data representative of one or more landmark features of a head of a human and data representative of one or more functional requirements associated with the human;

the one or more processors further configured to identify one or more landmark feature locations of the landmark features based on the data representative of one or more landmark features;

the one or more processors further configured to identify at least one relationship between two or more of the landmark feature locations, wherein identifying the at least one relationship between the two or more of the landmark feature locations comprises determining a distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion;

the one or more processors further configured to determine a set of manufacturing specifications for production of the patient respiratory interface component based on the one or more landmark feature locations and based on the data representative of the one or more functional requirements, wherein the set of manufacturing specifications comprises headgear strap dimensions, wherein determining the set of manufacturing specifications is further based at least in part on the at least one relationship between the two or more of the landmark feature locations;

the one or more processors further configured to determine, as part of the set of manufacturing specifications for production of the patient respiratory interface component, at least one knitting structure specification to be used for at least one portion of a one-piece headgear strap; and at least one manufacturing machine configured to produce the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

50. A processor-implemented method performed by a processing system including at least one processor and communication circuitry for production of a patient respiratory interface component comprising a headgear strap of a positioning and stabilising structure for a patient interface, the method comprising:

receiving, using the communication circuitry, data representative of one or more landmark features of a head of a human and data representative of one or more functional requirements associated with the human;

identifying, using the processing system, one or more landmark feature locations of the landmark features based on the data representative of one or more landmark features;

identifying, using the at least one processor, at least one relationship between two or more of the landmark feature locations, wherein identifying the at least one relationship between the two or more of the landmark feature locations comprises determining a distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion;

determining, using the processing system, a set of manufacturing specifications for production of the patient respiratory interface component based on the one or more landmark feature locations and based on the data representative of the one or more functional requirements, wherein the set of manufacturing specifications comprises headgear strap dimensions, wherein determining the set of manufacturing specifications is further based at least in part on the at least one relationship between the two or more of the landmark feature locations;

determining, as part of the set of manufacturing specifications for production of the patient respiratory interface component, at least one knitting structure specification to be used for at least one portion of a one-piece headgear strap; and communicating, using the communication circuitry, the set of manufacturing specifications to a manufacturing system comprising at least one manufacturing machine configured to produce the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

51. A system for producing a customised patient respiratory interface component comprising a headgear strap of a positioning and stabilising structure for a patient interface, the system comprising:

one or more processors for receiving data representative of one or more landmark features of a head of a human and data representative of one or more functional requirements associated with the human;

the one or more processors further configured to identify one or more landmark feature locations of the landmark features based on the data representative of one or more landmark features;

the one or more processors further configured to identify at least one relationship between two or more of the landmark feature locations, wherein identifying the at least one relationship between the two or more of the landmark feature locations comprises determining a distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion;

the one or more processors further configured to determine a set of manufacturing specifications for production of the patient respiratory interface component based on the one or more landmark feature locations and based on the data representative of the one or more functional requirements, wherein the set of manufacturing specifications comprises headgear strap dimensions, wherein determining the set of manufacturing specifications is further based at least in part on the at least one relationship between the two or more of the landmark feature locations;

the one or more processors further configured to determine, as part of the set of manufacturing specifications for production of the patient respiratory interface component, at least one knitting structure specification to be used for at least one portion of a one-piece headgear strap; and the one or more processors further configured to communicate the set of manufacturing specifications to a manufacturing system comprising at least one manufacturing machine configured to produce the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

52. A processor-implemented method performed by a processing system including at least one processor and communication circuitry for production of a patient respiratory interface component comprising a headgear strap of a positioning and stabilising structure for a patient interface, the method comprising:

receiving, using the communication circuitry, one or more landmark feature locations of landmark features of a head of a human and data representative of one or more functional requirements associated with the human, the one or more landmark feature locations identified from data representative of the one or more landmark features of the head;

identifying at least one relationship between two or more of the landmark feature locations, wherein identifying the at least one relationship between the two or more of the landmark feature locations comprises determining a distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion;

determining, using the processing system, a set of manufacturing specifications for production of the patient respiratory interface component based on the one or more landmark feature locations and based on the data representative of the one or more functional requirements, wherein the set of manufacturing specifications comprises headgear strap dimensions, wherein determining the set of manufacturing specifications is further based at least in part on the at least one relationship between the two or more of the landmark feature locations;

determining, as part of the set of manufacturing specifications for production of the patient respiratory interface component, at least one knitting structure specification to be used for at least one portion of a one-piece headgear strap; and communicating, using the communication circuitry, the set of manufacturing specifications to a manufacturing system comprising at least one manufacturing machine configured to produce the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

53. A system for producing a customised patient respiratory interface component comprising a headgear strap of a positioning and stabilising structure for a patient interface, the system comprising:

one or more processors for receiving one or more landmark feature locations of landmark features of a head of a human and data representative of one or more functional requirements associated with the human, the one or more landmark feature locations identified from data representative of the one or more landmark features of the head;

one or more processors for identifying, using the at least one processor, at least one relationship between two or more of the landmark feature locations, wherein identifying the at least one relationship between the two or more of the landmark feature locations comprises determining a distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion;

the one or more processors further configured to determine a set of manufacturing specifications for production of the patient respiratory interface component based on the one or more landmark feature locations and based on the data representative of the one or more functional requirements, wherein the set of manufacturing specifications comprises headgear strap dimensions, wherein determining the set of manufacturing specifications is further based at least in part on the at least one relationship between the two or more of the landmark feature locations;

the one or more processors further configured to determine, as part of the set of manufacturing specifications for production of the patient respiratory interface component, at least one knitting structure specification to be used for at least one portion of a one-piece headgear strap; and the one or more processors further configured to communicate the set of manufacturing specifications to a manufacturing system comprising at least one manufacturing machine configured to produce the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

54. A processor-implemented method for production of a patient respiratory interface component comprising a headgear strap of a positioning and stabilising structure for a patient interface, the method comprising:

receiving, using communication circuitry, a set of manufacturing specifications for production of the patient respiratory interface component, wherein the set of manufacturing specifications are determined based on one or more landmark feature locations identified from data representative of one or more landmark features of a head of a human and based on data representative of one or more functional requirements associated with the human, wherein the set of manufacturing specifications comprises headgear strap dimensions, wherein the set of manufacturing specifications are further determined based at least in part on at least one relationship between two or more of the landmark feature locations, wherein the at least one relationship is determined based on a distance between two or more of: a subnasale, a sellion, a tragion, a posterior-most point of the head, a superior-most point of the head, a lateral-most point of the orbital margin, an inferior-most point of the orbital margin, the frankfort horizontal plane, and a coronal plane aligned with the tragion;

receiving, as part of the set of manufacturing specifications for production of the patient respiratory interface component, at least one knitting structure specification to be used for at least one portion of a one-piece headgear strap; and causing one or more manufacturing machines to produce the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

55. A system for producing a customised patient respiratory interface component comprising a headgear strap of a positioning and stabilising structure for a patient interface, the system comprising:

one or more processors for receiving a set of manufacturing specifications for production of the patient respiratory interface component, wherein the set of manufacturing specifications are determined based on one or more landmark feature locations identified from data representative of one or more landmark features of a head of a human and based on data representative of one or more functional requirements associated with the human, wherein the set of manufacturing specifications comprises headgear strap dimensions, wherein the set of manufacturing specifications are further determined based at least in part on at least one relationship between two or more of the landmark feature locations, wherein the at least one relationship is determined based on a distance between two or more of: a subnasale, a sellion, a tragion, a posterior-most point of the head, a superior-most point of the head, a lateral-most point of the orbital margin, an inferior-most point of the orbital margin, the frankfort horizontal plane, and a coronal plane aligned with the tragion;

one or more processors for receiving, as part of the set of manufacturing specifications for production of the patient respiratory interface component, at least one knitting structure specification to be used for at least one portion of a one-piece headgear strap; and at least one manufacturing machine configured to produce the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

56. A processor-implemented method for production of a patient respiratory interface component comprising a headgear strap of a positioning and stabilising structure for a patient interface, the method comprising:

obtaining, based on data received from a device using communication circuitry, information representative of one or more landmark feature locations for a human's head;

obtaining, based on data received from a device using communication circuitry, information representative of at least one relationship between two or more of the landmark feature locations, wherein identifying the at least one relationship between the two or more of the landmark feature locations comprises determining a distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion;

determining, using at least one processor, a set of manufacturing specifications for production of the patient respiratory interface component based on the one or more landmark feature locations and based on data representative of one or more functional requirements associated with the human, wherein the set of manufacturing specifications comprises headgear strap dimensions, wherein determining the set of manufacturing specifications is further based at least in part on the at least one relationship between the two or more of the landmark feature locations;

determining, as part of the set of manufacturing specifications for production of the patient respiratory interface component, at least one knitting structure specification to be used for at least one portion of a one-piece headgear strap; and causing one or more manufacturing machines to produce the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

57. A system for producing a patient respiratory interface component comprising a headgear strap of a positioning and stabilising structure for a patient interface, the system comprising:

one or more processors for obtaining information representative of one or more landmark feature locations for a human head and one or more functional requirements associated with the human;

the one or more processors further configured to obtain information representative of at least one relationship between two or more of the landmark feature locations, wherein identifying the at least one relationship between the two or more of the landmark feature locations comprises determining a distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion;

the one or more processors further configured to determine a set of manufacturing specifications for production of the patient respiratory interface component based on the one or more landmark feature locations and based the one or more functional requirements associated with the human, wherein the set of manufacturing specifications comprises headgear strap dimensions, wherein determining the set of manufacturing specifications is further based at least in part on the at least one relationship between the two or more of the landmark feature locations;

the one or more processors further configured to determine, as part of the set of manufacturing specifications for production of the patient respiratory interface component, at least one knitting structure specification to be used for at least one portion of a one-piece headgear strap; and the one or more processors further configured to produce the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

58. Apparatus for producing a patient respiratory interface component comprising a headgear strap of a positioning and stabilising structure for a patient interface, the apparatus comprising:

means for obtaining information representative of one or more landmark feature locations for a human's head and one or more functional requirements associated with the human;

means for identifying, using the at least one processor, at least one relationship between two or more of the landmark feature locations, wherein identifying the at least one relationship between the two or more of the landmark feature locations comprises determining a distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion;

means for determining a set of manufacturing specifications for production of the patient respiratory interface component based on the one or more landmark feature locations and based on the one or more functional requirements, wherein the set of manufacturing specifications comprises headgear strap dimensions, wherein determining the set of manufacturing specifications is further based at least in part on the at least one relationship between the two or more of the landmark feature locations;

means for determining, as part of the set of manufacturing specifications for production of the patient respiratory interface component, at least one knitting structure specification to be used for at least one portion of a one-piece headgear strap; and means for producing the patient respiratory interface component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

59. A processor-implemented method for producing a customised component of an apparatus or device for treatment of a respiratory disorder, the customised component comprising a headgear strap of a positioning and stabilising structure for a patient interface, the method comprising:

receiving, using communication circuitry, data representative of one or more landmark features of a head of a human and data representative of one or more functional requirements which are not derived from the landmark feature locations;

data representative of at least one relationship between two or more of the landmark feature locations, wherein identifying the at least one relationship between the two or more of the landmark feature locations comprises determining a distance between two or more of: a subnasale, a sellion, a tragion, a posterior-most point of the head, a superior-most point of the head, a lateral-most point of the orbital margin, an inferior-most point of the orbital margin, the Frankfort horizontal plane, and a coronal plane aligned with the tragion;

determining, using at least one processor, a set of manufacturing specifications for production of the component based on the landmark features and the one or more functional requirements, wherein the set of manufacturing specifications comprises headgear strap dimensions, wherein determining the set of manufacturing specifications is further based at least in part on the at least one relationship between the two or more of the landmark feature locations;

determining, as part of the set of manufacturing specifications for production of the patient respiratory interface component, at least one knitting structure specification to be used for at least one portion of a one-piece headgear strap; and causing one or more manufacturing apparatuses to produce the component based on the set of manufacturing specifications, wherein the at least one knitting structure specification is selected from a plurality of knitting structure specifications comprising at least one of a tubular knit structure, an interlock knit structure, a spacer knit structure, a double jersey knit structure, a single jersey knit structure, a pique mesh knit structure, and a pique knit structure, wherein the at least one knitting structure specification is determined based at least in part on the at least one relationship between the two or more of the landmark feature locations.

60. The processor-implemented method of claim 59, wherein the producing the patient respiratory interface component comprises (a) mechanical manipulation of yarn to produce the component; (b) knitting the component; (c) flat knitting the component; (d) circular knitting the component; (e) forming the component from textiles; (e) additive manufacturing of the component; (f) three-dimensional printing of the component; and/or (g) laser cutting of the component.

61. The processor-implemented method of claim 59, wherein producing the component based on the set of manufacturing specifications comprises generating instructions for the one or more manufacturing apparatuses configured to produce the component and controlling the one or more manufacturing apparatuses to produce the component based on the generated instructions.

62. The processor-implemented method of claim 59, wherein the method is performed by a manufacturing system including the at least one processor and the communication circuitry.

* * * * *